US010781155B2

(12) United States Patent
Shimizu

(10) Patent No.: US 10,781,155 B2
(45) Date of Patent: *Sep. 22, 2020

(54) METHOD FOR PRODUCING ACETIC ACID

(71) Applicant: DAICEL CORPORATION, Osaka-shi, Osaka (JP)

(72) Inventor: Masahiko Shimizu, Himeji (JP)

(73) Assignee: DAICEL CORPORATION, Osaka-Shi (JP)

(*) Notice: Subject to any disclaimer, the term of this patent is extended or adjusted under 35 U.S.C. 154(b) by 207 days.

This patent is subject to a terminal disclaimer.

(21) Appl. No.: 16/071,337

(22) PCT Filed: Mar. 27, 2018

(86) PCT No.: PCT/JP2018/012439
§ 371 (c)(1),
(2) Date: Jul. 19, 2018

(87) PCT Pub. No.: WO2019/186697
PCT Pub. Date: Oct. 3, 2019

(65) Prior Publication Data
US 2020/0172461 A1 Jun. 4, 2020

(51) Int. Cl.
*C07C 51/12* (2006.01)
*C07C 51/44* (2006.01)
*C07C 53/08* (2006.01)

(52) U.S. Cl.
CPC ............. *C07C 51/12* (2013.01); *C07C 51/44* (2013.01); *C07C 53/08* (2013.01)

(58) Field of Classification Search
None
See application file for complete search history.

(56) References Cited

U.S. PATENT DOCUMENTS

| 5,880,311 A | 3/1999 | Uemura et al. |
| 10,246,399 B2 * | 4/2019 | Shimizu ................. C07C 51/47 |

(Continued)

FOREIGN PATENT DOCUMENTS

| JP | 8-231463 A | 9/1996 |
| JP | 2007-526310 A | 9/2007 |

(Continued)

OTHER PUBLICATIONS

Kalck ("Recent advances in the methanol carbonylation reaction into acetic acid" Coordination Chemistry reviews, 402, 2020, p. 213078) (Year: 2020).*

(Continued)

*Primary Examiner* — Amy C Bonaparte
(74) *Attorney, Agent, or Firm* — Birch, Stewart, Kolasch & Birch, LLP

(57) ABSTRACT

Provided are a method and an acetic acid production method, each of which can effectively restrain or prevent local corrosion of an inner wall of a process unit and/or line and can lower a formic acid concentration in an acetic acid product. The method produces acetic acid by a process including (1) a reaction step and (A) a separation step. In the reaction step (1), methanol is carbonylated with carbon monoxide in the presence of a catalytic system, acetic acid, methyl acetate, and water, where the catalytic system includes a metal catalyst and methyl iodide. In the separation step (A), the reaction mixture resulting from the reaction step is separated, using at least one selected from evaporators and distillation columns, into a stream containing the catalyst, an acetic acid stream rich in acetic acid, and a stream rich in lower-boiling components as compared with the acetic acid stream. In this method, an oxygen concentration is controlled by at least one of (a) controlling the oxygen concentration in a gaseous phase in the process to (Continued)

less than 7 percent by volume, and (b) controlling the oxygen concentration in a liquid phase in the process to less than $7 \times 10^{-5}$ g/g. In addition, a formic acid concentration in the liquid phase in the process is controlled to 500 ppm by mass or less. Thus, the formation of at least one of iodine and formic acid is restrained.

14 Claims, 4 Drawing Sheets

(56) References Cited

U.S. PATENT DOCUMENTS

| | | |
|---|---|---|
| 2005/0197508 A1 | 9/2005 | Scates et al. |
| 2008/0293966 A1 | 11/2008 | Scates et al. |
| 2008/0293967 A1 | 11/2008 | Scates et al. |
| 2009/0036710 A1 | 2/2009 | Miura et al. |
| 2013/0264186 A1 | 10/2013 | Shimizu et al. |
| 2017/0349521 A1* | 12/2017 | Shimizu .................. C01B 3/16 |
| 2019/0263744 A1* | 8/2019 | Shimizu ............... B01D 15/361 |

FOREIGN PATENT DOCUMENTS

| | | |
|---|---|---|
| JP | 2009-501129 A | 1/2009 |
| WO | WO 2012/086386 A1 | 6/2012 |
| WO | WO-2017057085 A1 * | 4/2017 ........... B01D 3/4294 |
| WO | WO-2018146895 A1 * | 8/2018 ............. C07C 51/12 |

OTHER PUBLICATIONS

International Search Report (PCT/ISA/210) issued in PCT/JP2018/012439, dated May 15, 2018.

Extended European Search Report, dated Jun. 13, 2019, for European Application No. 18742693.7.

* cited by examiner

[FIG. 1]
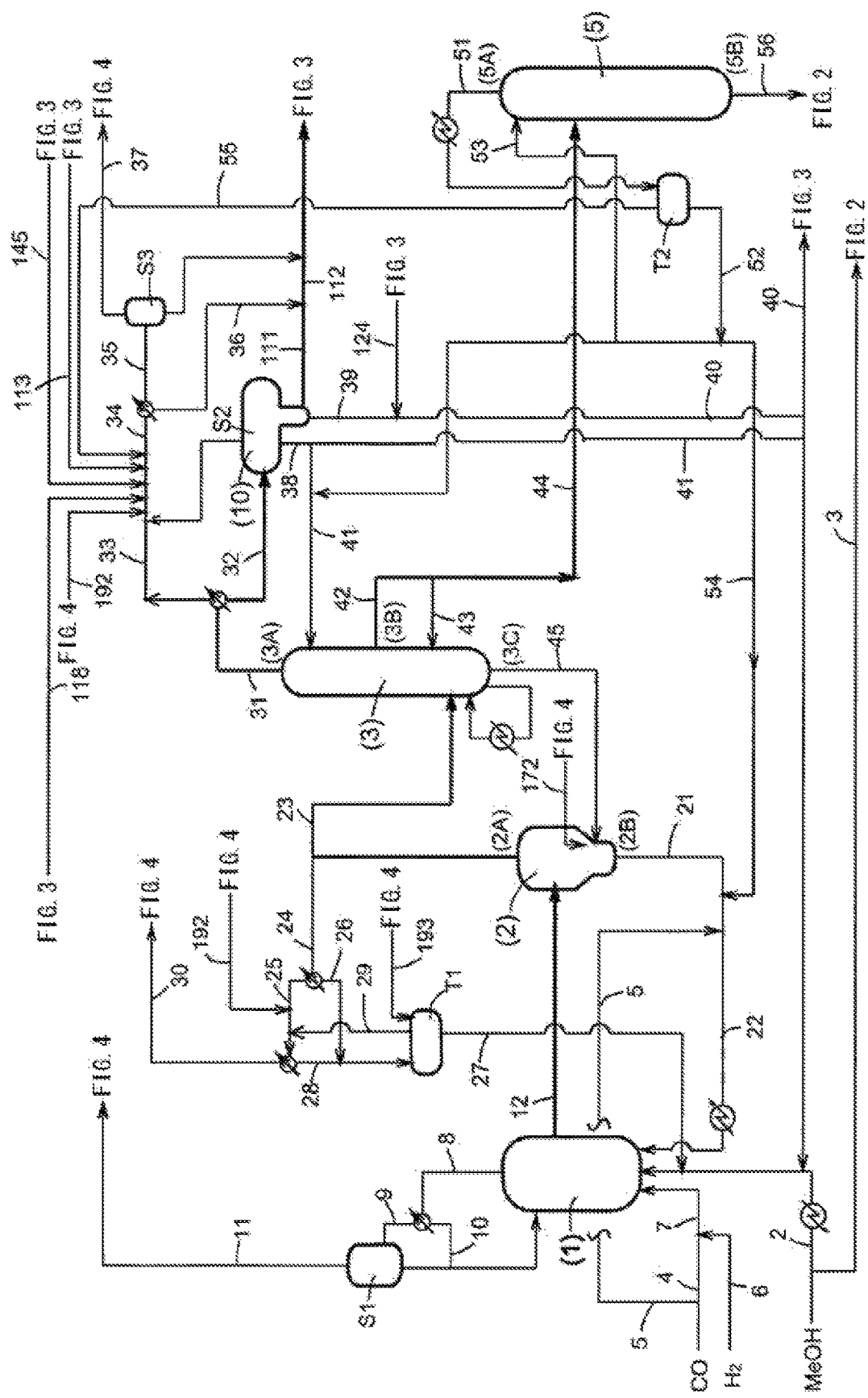

[FIG. 2]
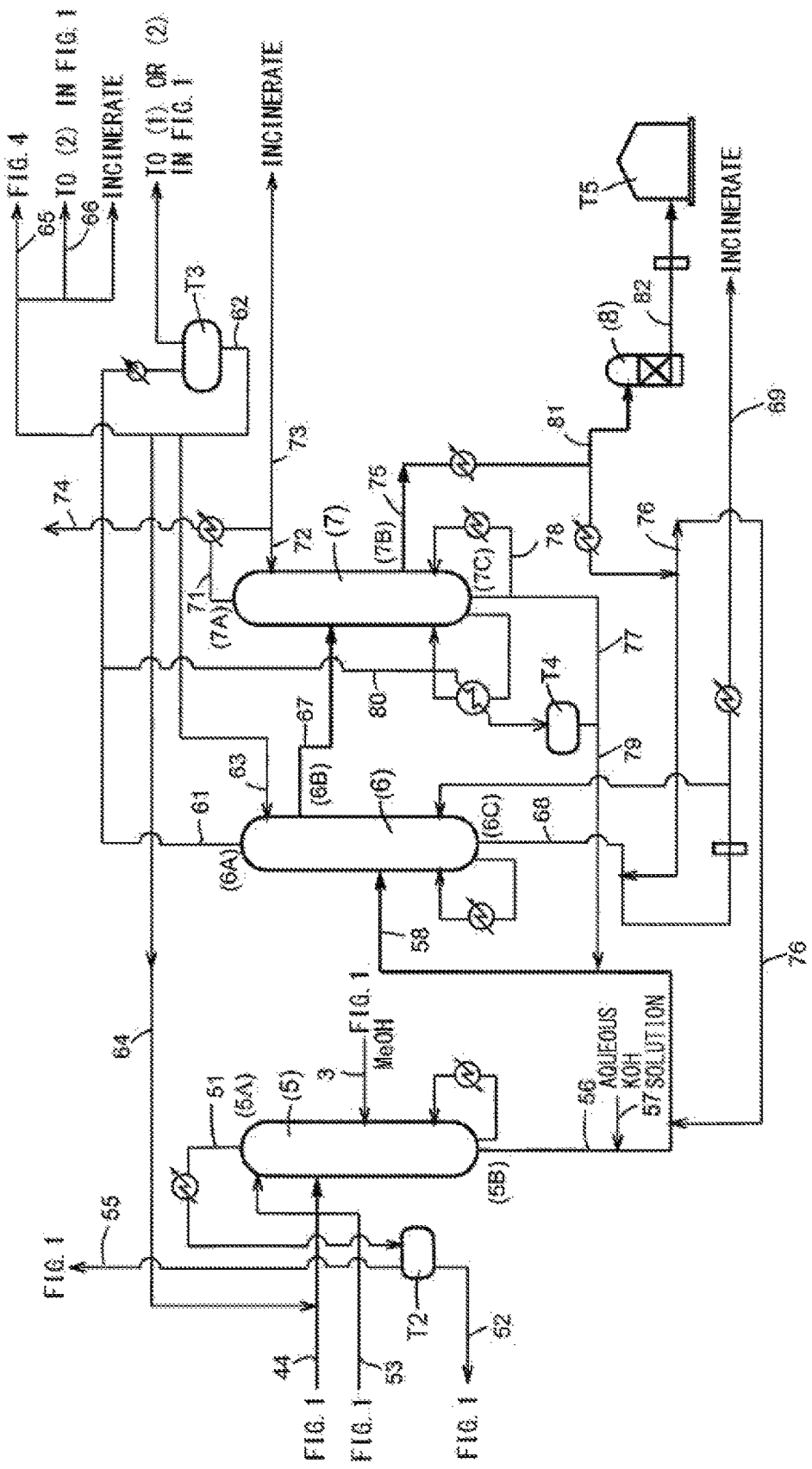

[FIG. 3]
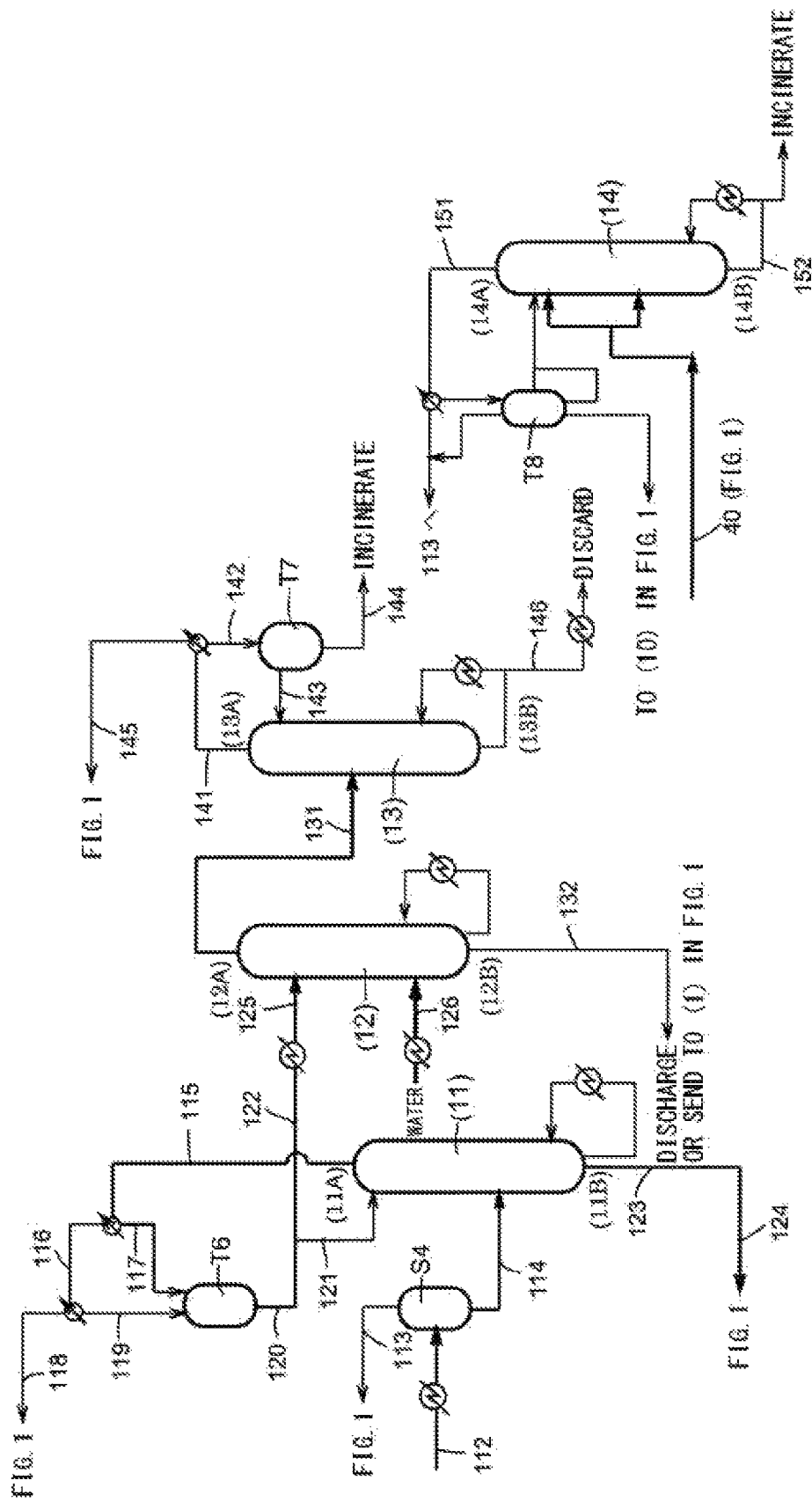

[FIG. 4]
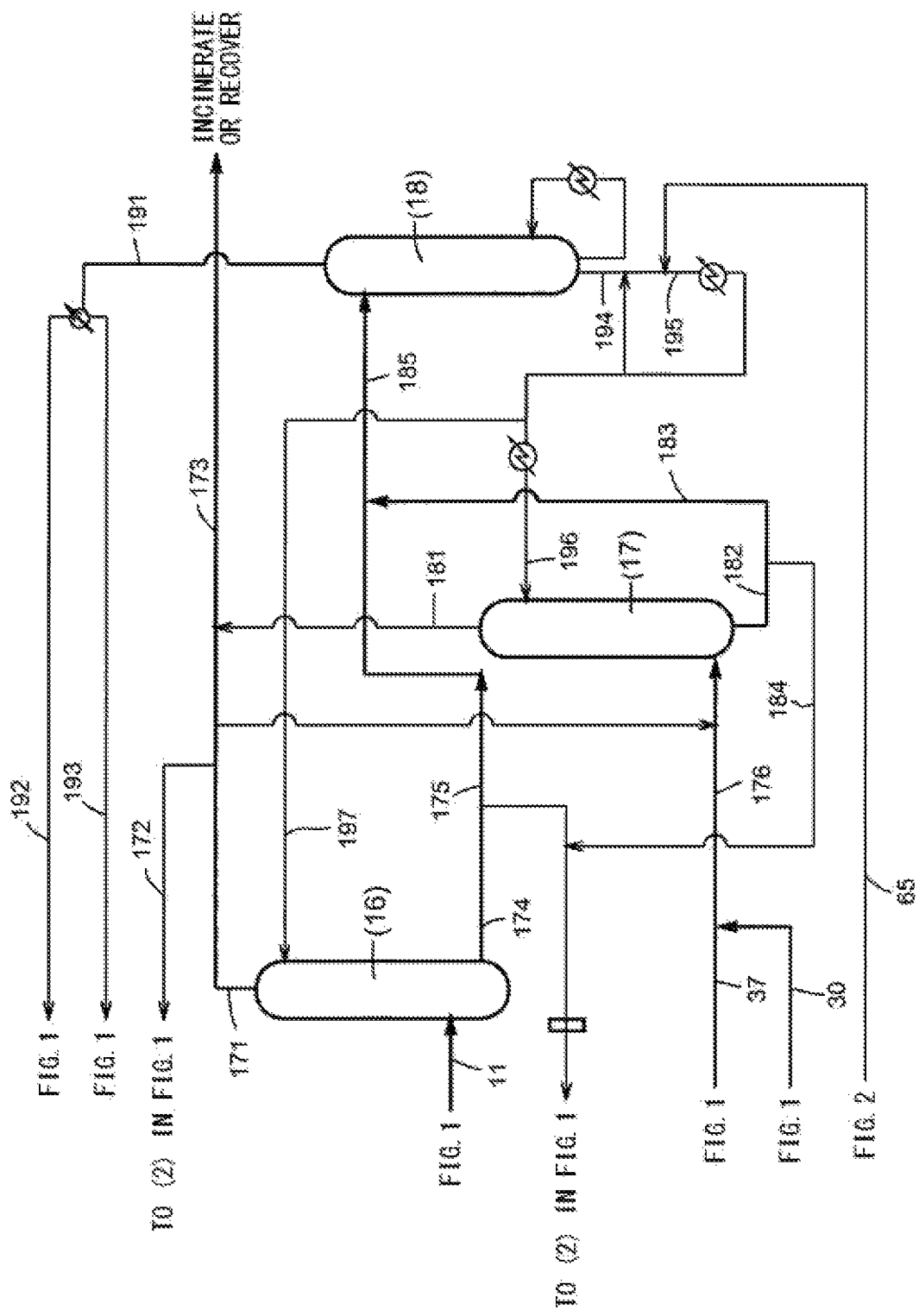

METHOD FOR PRODUCING ACETIC ACID

TECHNICAL FIELD

The present invention relates to methods for preventing or restraining the formation of iodine and other corrosive components, and formic acid; and methods for producing acetic acid by methanol carbonylation using the methods.

BACKGROUND ART

Acetic acid is produced industrially by carbonylation of methanol using a rhodium catalyst, at least one of a metal iodide and an iridium catalyst, and methyl iodide in the presence of water. In the methanol-carbonylation process, acetic acid is purified and productized using process units such as a reactor, an evaporator, a light ends column (splitter column), and a dehydration column. In the reactor, methanol is carbonylated in a carbon monoxide atmosphere. In the evaporator, the reaction mixture from the reactor is separated into a volatile phase and a less-volatile phase. In the light ends column, the volatile phase is distilled and separated into at least an overhead and an acetic acid stream. In the dehydration column, water is separated from the acetic acid stream. The light ends column and the dehydration column may be substituted with a single splitter-dehydrating column. Where necessary, acetic acid is productized through at least one of a heavy ends column and a product column, following the dehydration column, where the heavy ends column separates higher-boiling impurities from acetic acid.

Relating to the methanol-carbonylation process, Japanese Unexamined Patent Application Publication (Translation of PCT Application) No. 2007-526310 (PTL 1) discloses an improved method for the reduction and/or removal of permanganate-reducing compounds (PRC's), $C_{3-8}$ carboxylic acids, and $C_2$-$C_{12}$ alkyl iodide compounds. The method includes distilling a light phase (volatile phase) from the reaction mixture to yield a first overhead, distilling the first overhead to yield a second overhead containing methyl iodide, dimethyl ether, and the PRC's, extracting the second overhead with water two times to yield a second raffinate, and introducing at least part of the second raffinate into a reaction medium.

Unfortunately, corrosion may occur in process units and/or process lines in the methanol-carbonylation process. Specifically, an inner wall of a process unit and/or a process line is selectively corroded, which may result in pitting corrosion or spot corrosion that forms pits. In addition, the acetic acid product may be colored and have lower quality.

In the methanol-carbonylation process, it is known that hydrogen iodide corrodes the inner wall of a process unit and/or a process line. Japanese Unexamined Patent Application Publication (Translation of PCT Application) No. 2009-501129 (PTL 2) discloses a process for producing acetic acid. The method includes distilling an acetic acid stream containing acetic acid, hydrogen iodide, lower-boiling components, and higher-boiling components in a first distillation column to yield a first lower-boiling fraction, a first higher-boiling fraction, and a first side-cut stream including acetic acid; and distilling the first side-cut stream in a second distillation column to yield a second lower-boiling fraction, a second higher-boiling fraction, and a second side-cut stream containing acetic acid. In the method, water alone or in combination with at least one first component (A) selected from methanol and methyl acetate is fed to the first distillation column to convert hydrogen iodide into lower-boiling components such as methyl iodide and separate the resulting lower-boiling components.

Disadvantageously, even after separating hydrogen iodide by such a process, pitting corrosion or spot corrosion may still occur in the process unit and/or line.

In addition, formic acid may be by-produced in a reactor in the methanol-carbonylation process. Formic acid reduces the purity of the acetic acid product and is advantageously minimized. PTL 3 and PTL 4 disclose that formic acid results from the reaction between carbon monoxide and water; and that the formic acid concentration in the acetic acid product can be lowered by controlling the water concentration in a reaction medium at a low level. Disadvantageously, however, such a lowered water concentration in the reaction medium may often cause the catalyst to be unstable, and this lowers the reaction rate (productivity) of acetic acid.

CITATION LIST

Patent Literature

PTL 1: Japanese Unexamined Patent Application Publication (Translation of PCT Application) No. 2007-526310
PTL 2: Japanese Unexamined Patent Application Publication (Translation of PCT Application) No. 2009-501129
PTL 3: U.S. Published Application No. 2008/0293966
PTL 4: U.S. Published Application No. 2008/0293967

SUMMARY OF INVENTION

Technical Problem

Accordingly, the present invention has an object to provide a method and an acetic acid production method, each of which can effectively eliminate or minimize the local corrosion of an inner wall of a process unit and/or line and can lower the formic acid concentration in an acetic acid product.

The present invention has another object to provide a method and an acetic acid production method, each of which can effectively restrain the coloring of an acetic acid product. The present invention has yet another object to provide a method and an acetic acid production method, each of which can eliminate or minimize the coloring of an acetic acid product and can eliminate or minimize corrosion by hydrogen iodide. The present invention has still another object to provide a method and an acetic acid production method, each of which can effectively eliminate or minimize the corrosion of a process unit and/or line even when the unit and/or line is made of a low-grade metal material.

Solution to Problem

As a result of intensive investigations to search the mechanism of iodine and formic acid formation so as to achieve the objects, the inventors of the present invention found that, in a process for producing acetic acid by methanol carbonylation, oxygen is caused to enter a process stream by various factors such as components externally introduced into the process, and the introduced oxygen causes the formation of iodine and formic acid. Specifically, the inventors found that the oxygen oxidizes hydrogen iodide and/or methyl iodide to form by-product iodine, which corrodes a process unit and/or line; and that the control of the oxygen concentration in the process stream to a specific level or lower can effectively restrain iodine by-production and can eliminate or minimize local corrosion of the process unit and/or line. In addition, the inventors found that, in the presence of oxygen, methanol probably yields formaldehyde, and the formaldehyde probably yields formic acid. The present invention has been made on the basis of these findings.

Specifically, the present invention provides, in one aspect, a method for producing acetic acid by a process. The process includes (1) a reaction step, and (A) a separation step. The reaction step (1) is the step of carbonylating methanol with carbon monoxide in the presence of a catalytic system, acetic acid, methyl acetate, and water, where the catalytic system includes a metal catalyst and methyl iodide. The separation step (A) is the step of separating a reaction mixture resulting from the reaction step into a stream containing the catalyst, an acetic acid stream rich in acetic acid, and a stream rich in lower-boiling components as compared with the acetic acid stream, where the separation is performed using at least one selected from the group consisting of evaporators and distillation columns (one or more tanks and/or columns selected from the group consisting of evaporators (evaporation tanks) and distillation columns).

The separation step (A) may include (2) an evaporation step and (3) a lower-boiling component-removing step as follows:

(2) evaporating the reaction mixture resulting from the reaction step to form a volatile phase and the stream containing the catalyst; and (3) distilling the volatile phase to form the stream rich in lower-boiling components, and a first acetic acid stream rich in acetic acid.

The process may include (23) an evaporating-lower-boiling component-removing step instead of the steps (2) and (3). The evaporating-lower-boiling component-removing step (23) is the step of separating the reaction mixture resulting from the reaction step into the stream containing the catalyst, the stream rich in lower-boiling components, and a first acetic acid stream rich in acetic acid.

The lower-boiling component-removing step (3) may be a lower-boiling component-removing-dehydrating step. This step is a step that also has the function of an after-mentioned dehydrating step (5). Specifically, the step (3) may be a step that yields, as an acetic acid stream rich in acetic acid, an acetic acid stream which has a water concentration equivalent to that in an after-mentioned second acetic acid stream. Accordingly, the evaporating-lower-boiling component-removing step may be a step that also has the function of the dehydrating step (5) (evaporating-lower-boiling component-removing-dehydrating step). The acetic acid stream rich in acetic acid resulting from the lower-boiling component-removing-dehydrating step or from the evaporating-lower-boiling component-removing-dehydrating step corresponds to the second acetic acid stream resulting from the dehydrating step (5).

The acetic acid production method according to the present invention may include (4) a purification section to yield purified acetic acid from the acetic acid stream. The purification section (4) may include (5) a dehydrating step (preferably at least the dehydrating step (5) and (6) a higher-boiling component-removing step (6)), among steps (5) to (8) as follows:

(5) removing water from the acetic acid stream;
(6) removing higher-boiling components from the acetic acid stream;
(7) further rectifying (purifying by distillation) the acetic acid stream (rectifying step); and (8) separating iodine compounds from the acetic acid stream by ion exchange (ion exchange step).

The acetic acid production method according to the present invention may include (9) a separation section to separate at least acetaldehyde from the stream rich in lower-boiling components. The separation section (9) may include steps (10) to (13), among steps (10) to (14) as follows:

(10) condensing the stream rich in lower-boiling components to form an upper phase and a lower phase;
(11) forming a fifth overhead rich in acetaldehyde and methyl iodide from at least one of the upper phase and the lower phase;
(12) extracting acetaldehyde from the fifth overhead to yield an extract and a raffinate, where the extract is rich in acetaldehyde, and the raffinate is rich in methyl iodide;
(13) separating aldehyde from at least one of the extract and the raffinate; and
(14) separating an alkane or alkanes from at least one of the upper phase and the lower phase.

The acetic acid production method according to the present invention may include (15) an offgas treatment section to allow an absorbing solvent to absorb an offgas from the process. The offgas treatment section (15) may include at least one step selected from steps (16) and (17) among steps (16) to (18) as follows:

(16) allowing the absorbing solvent to absorb the offgas under a high pressure;
(17) allowing the absorbing solvent to absorb the offgas under a low pressure; and
(18) stripping a gaseous component or components absorbed in at least one of the absorbing step (16) and (17).

The acetic acid production method according to the present invention produces acetic acid while controlling an oxygen concentration by at least one procedure selected from:

(a) controlling the oxygen concentration in a gaseous phase in the process to less than 7 percent by volume; and
(b) controlling the oxygen concentration in a liquid phase in the process to less than $7 \times 10^{-5}$ g/g.

The gaseous phase in the process may contain at least one selected from methyl iodide and hydrogen iodide. The gaseous phase in the process may further contain at least one selected from the group consisting of acetic acid, methyl acetate, methanol, water, acetaldehyde, an acetaldehyde-derived by-product, and a dialkyl ether. The by-product may include at least one selected from the group consisting of alkyl iodides containing 2 or more carbon atoms, alkanals containing 4 or more carbon atoms, alkanecarboxylic acids containing 3 or more carbon atoms, alkanes, and ketones. The dialkyl ether may include dimethyl ether.

In the acetic acid production method according to the present invention, the oxygen concentration in at least one process stream (at least one process stream selected from the group consisting of process unit streams and process line streams) in the process may be controlled by at least one procedure selected from:

(a-1) controlling the oxygen concentration in the gaseous phase typically to 5 percent by volume or less; and
(b-1) controlling the oxygen concentration in the liquid phase typically to $2 \times 10^{-3}$ g/g or less.

Oxygen, if present in an excessively high concentration, may cause iodine to form in the process and to corrode a process unit and/or line. In addition, oxygen, if present in an excessively high concentration, may cause formaldehyde and formic acid to form in the process and to increase the formic acid concentration in the acetic acid product.

The proportion of oxygen to carbon monoxide may be 2 percent by volume or less (e.g., 1 percent by volume or less) in each of the gaseous phase and the liquid phase in at least one process stream selected from the group consisting of process unit streams and process line streams.

At least one oxygen-source component may be introduced into the process, so as to regulate at least one of the oxygen concentration in the gaseous phase and the oxygen concentration in the liquid phase, where the oxygen-source component is selected from the group consisting of oxygen-containing gases, oxygen-containing compounds, and oxygen generators. By introducing such an oxygen-source component, the oxygen concentration in the gaseous phase may be controlled to 1 ppt by volume or more (e.g., 100 ppt by volume or more), and/or the oxygen concentration in the liquid phase may be controlled to $0.1 \times 10^{-9}$ g/g or more (e.g., $0.1 \times 10^{-8}$ g/g or more), in at least one process stream selected from the group consisting of process unit streams and process line streams.

The oxygen concentration in at least one process stream selected from the gaseous phase and the liquid phase may be controlled to 0.25 mole or less per mole of the totality of hydrogen iodide and methyl iodide, so as to restrain iodine formation.

The acetic acid production method according to the present invention produces acetic acid while the formic acid concentration in the liquid phase in the process is controlled to 500 ppm by mass or less.

The gaseous phase and/or the liquid phase is preferably a gaseous phase and/or a liquid phase in, identically or differently, at least one step selected from the group consisting of the reaction step (1); the steps included in the separation step (A) (the evaporation step (2) and the lower-boiling component-removing step (3)); the steps included in the purification section (4) (the dehydrating step (5), the higher-boiling component-removing step (6), and the rectifying step (7)); the steps included in the separation section (9) (the liquid-liquid separation step (10), the first acetaldehyde separation step (11), the extraction step (12), the second acetaldehyde separation step (13), and the alkane separation step (14)); and the steps included in the offgas treatment section (15) (the high-pressure absorbing step (16), the low-pressure absorbing step (17), and the stripping step (desorption step) (18)). The gaseous phase and/or the liquid phase is more preferably a gaseous phase and/or a liquid phase in at least one step selected from the group consisting of the reaction step (1) (e.g., a liquid reaction mixture and/or a gaseous phase in the reactor), the evaporation step (2) (in particular, a volatile phase), the lower-boiling component-removing step (3) (in particular, an overhead from the splitter column), the liquid-liquid separation step (10) (in particular, an upper phase and/or a lower phase), the high-pressure absorbing step (16), and the low-pressure absorbing step (17). The gaseous phase and/or the liquid phase is more preferably a gaseous phase and/or a liquid phase in at least one step selected from the group consisting of the reaction step (1) (e.g., a liquid reaction mixture and/or a gaseous phase in the reactor), the evaporation step (2) (in particular, a volatile phase), and the lower-boiling component-removing step (3) (in particular, an overhead from the splitter column).

The present invention also provides, in another aspect, a method for restraining the formation of at least one of iodine and formic acid in a process. The method according to the present invention includes (1) a reaction step, and (A) a separation step. The reaction step (1) is the step of carbonylating methanol with carbon monoxide in the presence of a catalytic system, acetic acid, methyl acetate, and water, where the catalytic system includes a metal catalyst and methyl iodide. The separation step (A) is the step of separating a reaction mixture resulting from the reaction step into a stream containing the catalyst, an acetic acid stream rich in acetic acid, and a stream rich in lower-boiling components as compared with the acetic acid stream, where the separation is performed using at least one selected from the group consisting of evaporators and distillation columns (one or more tanks and/or columns selected from the group consisting of evaporators (evaporating tanks) and distillation columns).

To restrain the formation of at least one of iodine and formic acid, the method according to the present invention includes controlling an oxygen concentration by at least one procedure selected from procedures (a) and (b) as follows:
(a) controlling the oxygen concentration in a gaseous phase in the process to less than 7 percent by volume; and
(b) controlling the oxygen concentration in a liquid phase in the process to less than $7 \times 10^{-5}$ g/g.

Also to restrain the formation of at least one of iodine and formic acid, the method according to the present invention further includes controlling a formic acid concentration in the liquid phase in the process to 500 ppm by mass or less.

The term "gaseous phase" (or gaseous phase portion) in the process, which has the specific oxygen concentration, refers to a gaseous phase in at least one stage (process unit and/or line) among all gaseous phases in the process. A gas constituting the gaseous phase (or gaseous phase portion) is at least one offgas among all offgases in the process. The gas may be an "offgas" to be fed to the offgas treatment step, or may be an "offgas" from at least one of all process units and process lines in the process. The term "offgas" refers not only to a gas to be discharged from the process out of the system, but also to a gas in the process (e.g., gases in process units and in lines).

As used herein, the term "process unit" refers to a device or unit which performs a process unit operation such as reaction, evaporation, distillation, cooling and/or condensation, liquid-liquid separation, storage, or absorption. Of acetaldehyde and acetaldehyde-derived by-products, components that shorten a permanganate time in a permanganate time test (permanganate time) are also simply referred to as PRC's. Non-limiting examples of the components include aldehydes; and alkyl iodides containing 2 or more carbon atoms. Unless otherwise specified, an acetaldehyde-containing aqueous phase resulting from liquid-liquid (or biphasic) separation is synonymous with a lighter phase or an upper phase; and a methyl iodide-containing organic phase is synonymous with a heavier phase, a methyl iodide phase, or a lower phase. An aqueous phase resulting from extraction is synonymous with an extract, and an organic phase resulting from extraction is synonymous with a raffinate.

As used herein, a gaseous phase portion and a gaseous stream are also generically referred to as a "gaseous phase"; and a liquid phase portion and a liquid stream are also generically referred to as a "liquid phase". As used herein, the totality of a mixture constituting each of the gaseous phase and the liquid phase, including impurities, is 100%. If the mixture constituting the gaseous phase (gaseous mixture) contains a condensable component, the composition of the gaseous-phase mixture may fail to be measured accurately. This is because, even if the mixture is gaseous under process conditions (temperature and pressure), the condensable component in the mixture having a temperature lowered by sampling may be liquefied at room temperature and an atmospheric pressure (25° C., 1 atom≈0.1 MPa). To eliminate or minimize this disadvantage, the composition of the mixture constituting the gaseous phase (gaseous mixture) is expressed on the basis of the volume (percent by volume) or mass (percent by mass) of the gaseous-phase mixture at a temperature of 25° C. The composition of the mixture constituting the liquid phase (liquid mixture) is expressed on the basis of mass (such as percent by mass).

Advantageous Effects of Invention

With the present invention, the by-production of at least one of iodine and formic acid can be restrained by controlling (regulating) the oxygen concentration in a process stream to a specific level or less. The restrainment of iodine by-production can effectively restrain or prevent local corrosion of an inner wall of a process unit and/or line. This configuration can also lower the total iodine concentration in an acetic acid product and can effectively restrain coloring of the acetic acid product. In addition, the configuration can not only prevent or restrain the coloring of the acetic acid product, but also restrain the formation of hydrogen iodide from iodine, and can eliminate or minimize corrosion by hydrogen iodide. Accordingly, the corrosion of a process unit and/or line, even if being made of a low-grade metal material, can be effectively prevented or restrained. In addition, with the present invention, the formation of formic acid in the process stream can be restrained, and the formic acid concentration in the acetic acid product can be easily or simply lowered.

BRIEF DESCRIPTION OF DRAWINGS

FIG. 1 illustrates, as a flow chart, an exemplary process from a reaction step to a liquid-liquid separation step and a dehydrating step in a method according to an embodiment of the present invention and equipment for producing acetic acid;

FIG. 2 illustrates, as a flow chart, an acetic acid purification section including a dehydrating step;

FIG. 3 illustrates, as a flow chart, a separation section to separate at least acetaldehyde from a phase resulting from the liquid-liquid separation step; and FIG. 4 illustrates, as a flow chart, an offgas treatment section to treat an offgas from the process.

DESCRIPTION OF EMBODIMENTS

In a process for producing acetic acid by methanol carbonylation, oxygen enters a process stream due to various factors such as components introduced to the process from the outside. For example, carbon monoxide or methanol results from partial oxidation of a carbon source (a carbon compound or a hydrocarbon compound) with oxygen or air to give a syngas; and purifying the syngas, where non-limiting examples of the carbon source include fossil fuels such as coal and petroleum; and natural gases, and the syngas contains, for example, CO, $H_2$, $CO_2$, and a trace of $O_2$. Non-limiting examples of the technique of partial oxidation of the carbon source include steam methane reforming (SMR), autothermal reforming (ATR), and partial oxidation (PDX). Not only in the partial oxidation with oxygen, but also in the SMR, the carbon source or steam contains oxygen. Accordingly, a trace of oxygen enters the process by introduction (or feeding) of carbon monoxide and methanol as raw materials to a reactor, or by feeding or addition of methanol to a process unit (such as a dehydration column or a treatment tank) so as to convert hydrogen iodide into methyl iodide and thereby remove hydrogen iodide.

To adjust a water content in the process, water is fed to, or used in, the process. For example, water is fed to a reaction step; and water is used in extraction of a second overhead (typically in a water extracting device or an aqueous extraction-distillation column), where the second overhead results from distillation of a first overhead in an aldehyde-removing column, where the first overhead is from a light ends column (splitter column). In addition, an aqueous solution of an alkali metal hydroxide may be used in a process unit such as a dehydration column or a treatment tank, so as to remove hydrogen iodide. Such water (aqueous solution) contains a trace of oxygen dissolved therein, and oxygen enters the process stream upon the use of the water.

The acetic acid production process by carbonylation employs various apparatuses such as tanks, hold tanks, pumps, and gauging instruments (such as level gauges and pressure gauges) between a reactor to a product column. Nitrogen gas purge may be performed on a high-pressure seal portion or another portion in order to prevent the process stream (such as an acetic acid stream) from flowing back to the gauging instruments and liquefying, or in order to prevent carbon monoxide from leaking from an agitator shaft of the reactor. The nitrogen gas purge to the gauging instruments results in introduction of nitrogen gas into the process. In pressure sealing to a seal portion of the agitator shaft, a portion of nitrogen gas may leak in the reactor through the seal portion. Such nitrogen gas also contains a trace of oxygen.

The oxygen introduced to the process due to various factors as described above reacts with hydrogen iodide or methyl iodide present in the process to form free iodine $I_2$ by the oxidative reaction (such as $2HI+\frac{1}{2}O_2 \rightarrow I_2+H_2O$; $2CH_3I+\frac{1}{2}O_2 \rightarrow CH_3OCH_3+I_2$). The inventors have found that, when the formed iodine $I_2$ is attached or adheres to an inner wall of a process unit and/or line, the attached portion is selectively or locally corroded, which results in pitting corrosion or spot corrosion that forms pores or pits.

In an atmosphere having a water concentration of 5 percent by mass or less, hydrogen iodide (HI) usually behaves in the same manner as water and is enriched in top(s) of a light ends column for removing lower boiling components, a dehydration column, a heavy ends column for removing higher boiling components, and/or a product column. Whereas, iodine ($I_2$), which has a higher boiling point as compared with hydrogen iodide, is carried together with a higher boiling point fraction (heavier fraction) at the process unit (e.g., a side-cut stream from a light ends column for removing lower boiling components, a bottom stream from a dehydration column, and a side-cut stream from a product column) to finally enter the product acetic acid. Thus, the inventors have also found that the acetic acid product may have an increased iodine concentration or may be colored dark to reddish brown peculiar to iodine. The iodine-contaminated acetic acid product adversely affects a catalytic activity in producing an acetic acid derivative such as vinyl acetate. Accordingly, it is usually necessary to control the iodine concentration in the acetic acid product to a level as very low as 10 ppb by mass or less.

As described above, methanol or an alkali metal hydroxide (such as potassium hydroxide) may be added to a process unit such as a dehydration column to convert a trace of hydrogen iodide into methyl iodide or an alkali iodide (such as potassium iodide) which is then removed. Even in such a method, it is impossible to remove iodine once formed from hydrogen iodide and/or methyl iodide. In a stage downstream from the process unit such as a dehydration column, the hydrogen iodide concentration is lowered, but a process stream containing iodine, when exposed to a reducing atmosphere, gives hydrogen iodide by the inverse reaction. Thus, an inner wall of a process unit and/or line, when being made of a low-grade metal material (e.g., a low-grade stainless steel (SUS) material or a HASTELLOY C material), may be corroded not locally by iodine, but uniformly by hydrogen iodide HI.

Assume that the oxygen introduced into the process due to various factors as described above reacts with a methanol source (such as methanol, methyl acetate, or dimethyl ether) and/or methanol in the process. In this case, it is supposed that the oxygen forms formaldehyde by an oxidation reaction ($CH_3OH + \frac{1}{2}O_2 \rightarrow HCHO + H_2O$), and the formed formaldehyde, when further reacting with oxygen, forms formic acid by the progress of an oxidation reaction ($HCHO + \frac{1}{2}O_2 \rightarrow HCOOH$). With an increasing formic acid concentration in the acetic acid product, the acetic acid product has a lower acetic acid purity and lower quality.

To solve such problems, at least one of the oxygen concentration and the formic acid concentration in the process stream is controlled according to an embodiment of the present invention. The methanol carbonylation process (reaction system) is usually a pressurized system, and therefore the oxygen concentration in the process stream can be controlled (regulated) by controlling the oxygen concentrations in raw materials and feed lines. For example, the oxygen concentration in carbon monoxide can be controlled by appropriately operating a carbon monoxide production process. For example, the oxygen concentration in carbon monoxide may be controlled by regulating (or adjusting) at least one of the feed amount of oxygen and the feed amount of steam (water vapor) relative to a carbon monoxide raw material (such as coal or natural gas, heavy oil, or asphalt) to allow partial oxidation of the raw material with oxygen to proceed thoroughly. Alternatively, the oxygen concentration may be controlled by measuring the oxygen concentration in a purified carbon monoxide and; on the basis of the measured value, determining whether the carbon monoxide can be used, or feedback-controlling the carbon monoxide production process, or introducing an inert gas.

For methanol, the concentration of oxygen dissolved in methanol may be controlled by measuring the dissolved oxygen concentration in the methanol; and, on the basis of the measured value, determining whether the methanol is usable, or controlling the dissolved oxygen concentration in the methanol typically by heating. For water and/or an aqueous solution (aqueous alkaline solution (aqueous alkali metal hydroxide solution) or aqueous sodium hypophosphite solution) to be fed to the process (such as the reaction system), the concentration of dissolved oxygen may be controlled by measuring the concentration of oxygen dissolved in the water and/or the aqueous solution; and, on the basis of the measured value, determining whether the water and/or the aqueous solution is usable, or employing an aqueous solution having a dissolved oxygen concentration controlled typically by heating (e.g., water or an aqueous solution having an oxygen concentration lowered typically by boiling).

For a gas or a liquid to be fed to the process, the oxygen concentration in the process stream can be controlled or adjusted by measuring the oxygen concentration in the gas or liquid, and controlling the oxygen concentration on the basis of the measured value, by a procedure similar to that mentioned above.

The oxygen concentration in the process stream may also be controlled typically by minimizing the amount of purge nitrogen gas in the process stream; or by performing purging with carbon monoxide gas or another inert gas, instead of the nitrogen gas.

Non-limiting examples of an oxygen analyzer usable herein to determine the oxygen concentration in a gas or a gaseous phase include various oxygen analyzers such as an explosion-proof magneto-pneumatic oxygen analyzer MPA-51d/p (trade name, supplied by HORIBA, Ltd.), single channel zirconia oxygen analyzers ZR402G and ZR22G (trade names, supplied by Yokogawa Electric Corporation), and a laser gas analyzer SITRANS SL (trade name, supplied by Siemens AG) using near infrared laser.

Non-limiting examples of an oxygen analyzer (dissolved oxygen sensor) usable herein to determine the oxygen concentration in a liquid or a liquid phase include Models DO, OC, ODM, and OBM (supplied by DKK-TOA Corporation), a DO Meter (Dissolved Oxygen Meter) supplied by Iijima Electronics Corporation, an oxygen analyzer that can measure the concentration of oxygen dissolved in water and in a solvent (methanol) (supplied by Mettler-Toledo International Inc.), and a Model OX Oxygen Analyzer (supplied by Yokogawa Electric Corporation) that measures the concentration of oxygen in a gas.

The oxygen analyzer Model OC64 typically with 7561L supplied by DKK-TOA Corporation has a lower detection limit of oxygen in a liquid of 0.1 μg/L. For example, the lower measurement limit (detection limit) of the oxygen concentration is (0.1/1000000) g/1000 g=0.1 ppb in a liquid having a specific gravity of 1; and is 0.05 ppb in a liquid having a specific gravity of 2. The oxygen analyzer OX400 supplied by Yokogawa Electric Corporation has a lower measurement limit of the oxygen concentration in a gas of 0.01 ppm (10 ppb) by volume. For a sample (a gaseous phase or a liquid phase) having an oxygen concentration of less than the measurement limit, the oxygen concentration may be determined by a procedure as follows. Specifically, an oxygen-concentrated component (oxygen concentrate) is formed from the gaseous phase or the liquid phase using a common technique, the oxygen concentration in the oxygen concentrate is measured, and the measured value is converted to an oxygen concentration in the sample. Non-limiting examples of the common technique include selective adsorption of oxygen by an adsorbent; selective permeation of oxygen through a permselective membrane such as an oxygen-enriched membrane; distillation for separating into a lighter fraction and a heavier fraction; and extraction.

The oxygen concentrations in a gas (or a gaseous phase), and in a liquid (or a liquid phase) may be observed continuously by monitoring a value detected or measured with an oxygen analyzer (oxygen sensor) disposed in a process unit or a process line; or may be observed by periodically sampling and analyzing a sample from a process unit or a process line. The oxygen concentration may be controlled by comparing the value, which is detected or measured using the oxygen analyzer (oxygen sensor), with an upper reference value (upper threshold value), and, when the detected or measured value reaches the threshold value, automatically introducing a fluid (gas or liquid) having a low oxygen concentration to a process stream, or switching the introduction stream to a fluid having a low oxygen concentration. When the oxygen concentration is excessively low (when the oxygen concentration reaches a lower threshold value as a lower reference value), an oxygen source may be introduced to the process stream.

In a process under reduced pressure, the oxygen concentration in a process stream under reduced pressure may be controlled by controlling the pressure to a target pressure with introduction of an inert gas while maintaining an airtight condition for holding the operating pressure, then starting the operation, and measuring the oxygen concentration in a gas discharged from a vacuum pump.

The control of the oxygen concentration in the above manner can restrain the by-production of at least one of iodine and formic acid. This can provide useful process conditions that can approximately solve the disadvantages including local corrosion by iodine, increase of at least one of total iodine concentration and formic acid concentration in an acetic acid product, and coloring of the acetic acid product. The present invention is also very useful for controlling or regulating the iodine concentration and the formic acid concentration in the acetic acid product to very low levels respectively of 10 ppb by mass or less and 50 ppm by mass or less. High-grade corrosion-resistant metals such as zirconium are known to offer complete resistance to corrosion under wide-ranging conditions including reducing conditions and oxidizing conditions. Even such high-grade corrosion-resistant metals, however, may be corroded under strongly oxidizing conditions. Accordingly, a process unit and/or line, when being made of some materials, may be corroded in some oxygen concentrations, although the process unit and/or line may offer corrosion resistance at a somewhat high oxygen concentration. The present invention can also restrain corrosion of this kind.

As apparent from these, the present invention is applicable to any of process units (steps) and lines in a method (process) for producing acetic acid by methanol carbonylation. Specifically, the gaseous phase and the liquid phase in the process in the present invention are respectively a gaseous phase and a liquid phase in at least one process stream, among all streams in all the process units (steps) and process lines in the process for producing acetic acid by methanol carbonylation.

The present invention restrains the by-production of at least one of iodine and formic acid and is applicable to a process stream (such as a gaseous phase in the process) containing at least one selected from the group consisting of methyl iodide, hydrogen iodide, and formic acid. The process stream (such as a gaseous phase in the process) may contain at least one selected from the group consisting of acetic acid, methyl acetate, methanol, water, acetaldehyde, acetaldehyde-derived by-products, and dialkyl ethers, depending on the process unit and/or the process line, as described later. The by-products may include at least one selected from the group consisting of alkyl iodides containing 2 or more carbon atoms, alkanals containing 4 or more carbon atoms, alkanecarboxylic acids containing 3 or more carbon atoms, alkanes, and ketones. The dialkyl ethers may include dimethyl ether.

In a process for producing acetic acid (in at least one process stream selected from the group consisting of process unit streams and process line streams), the method according to the present invention controls at least one oxygen concentration selected from (a) an oxygen concentration in a gaseous phase in the process and (b) an oxygen concentration in a liquid phase in the process.

The oxygen concentration (a) in a gaseous phase in the process (a gaseous phase in least one stage of the process, particularly preferably all gaseous phases in the process) is controlled to less than 7 percent by volume. The oxygen concentration (a) may be 6.5 percent by volume or less (e.g., 6 percent by volume or less), and preferably 5.5 percent by volume or less, and may be controlled to generally 5 percent by volume or less (e.g., 3 percent by volume or less), preferably 1 percent by volume or less (e.g., 0.5 percent by volume or less), more preferably 0.1 percent by volume or less (e.g., 0.01 percent by volume or less), and particularly preferably 0.001 percent by volume (10 ppm by volume) or less (e.g., 0.0001 percent by volume (1 ppm by volume) or less).

The oxygen concentration in the gaseous phase is not limited in its lower limit and may be typically 1 ppt by volume or more (e.g., 100 ppt by volume or more), and preferably 1 ppb by volume or more (e.g., 100 ppb by volume or more), or may be zero (0), or equal to or less than the lower measurement limit.

The oxygen concentration (b) in a liquid phase in the process (a liquid phase in at least one stage of the process, particularly preferably all liquid phases in the process) is controlled to less than $7 \times 10^{-3}$ g/g, and may be controlled to $2 \times 10^{-3}$ g/g or less (e.g., $1 \times 10^{-3}$ g/g or less), preferably $0.5 \times 10^{-3}$ g/g or less (e.g., $0.1 \times 10^{-5}$ g/g or less), more preferably $0.05 \times 10^{-3}$ g/g or less (e.g., $0.01 \times 10^{-3}$ g/g or less), and particularly preferably $0.001 \times 10^{-3}$ g/g or less (e.g., $0.0001 \times 10^{-3}$ g/g or less).

The oxygen concentration in the liquid phase is also not limited in its lower limit and may be typically $0.1 \times 10^{-9}$ g/g or more, or may be zero (0), or equal to or less than the lower measurement limit. In a liquid phase such as a process liquid under pressure (under a load) or a process liquid at a high temperature, the oxygen concentration (or dissolved oxygen concentration) may fail to be measured accurately due typically to difficulty of sampling and vaporization of oxygen. In this case, the oxygen concentration may be determined as an estimated value (experimentally estimated value) by measuring the oxygen concentrations in the process liquid at different temperatures and/or different pressures, and estimating an oxygen concentration at an actual process temperature and pressure, or may be calculated using Aspen Plus (supplied by Aspen Technology, Inc.).

With an increasing oxygen concentration in a process stream (gaseous phase and/or liquid phase), at least one of iodine and formic acid more tends to be formed in the process stream. Accordingly, the process stage (step) including a gaseous phase and/or a liquid phase to be controlled on oxygen concentration by at least one of the procedure (a) and (b) is preferably a process stage (step) in which at least one of hydrogen iodide, methyl iodide, methanol, and formaldehyde is liable to be present. The gaseous phase and/or the liquid phase to be controlled is preferably a gaseous phase and/or a liquid phase in at least one step selected from the group consisting of: the reaction step (1); the steps included in the separation step (A) (the evaporation step (2) and the lower-boiling component-removing step (3)); the steps included in the purification section (4) (the dehydrating step (5), the higher-boiling component-removing step (6), and the rectifying step (7)); the lower-boiling component-removing-dehydrating step; the steps included in the separation section (9) (the liquid-liquid separation step (10), the first acetaldehyde separation step (11), the extraction step (12), the second acetaldehyde separation step (13), and the alkane separation step (14)); and the steps included in the offgas treatment section (15) (the high-pressure absorbing step (16), the low-pressure absorbing step (17), and the stripping step (18)). In particular, the gaseous phase and/or the liquid phase is more preferably a gaseous phase and/or a liquid phase in at least one step selected from the group consisting of the reaction step (1) (e.g., a liquid reaction mixture and/or a gaseous phase in the reactor); the evaporation step (2) (in particular, a volatile phase), the lower-boiling component-removing step (3) (in particular, an overhead from a splitter column), the lower-boiling component-removing-dehydrating step, the liquid-liquid separation step (10) (in particular, an upper phase and/or a lower phase), the high-pressure absorbing step (16), and the low-pressure absorbing step (17). The gaseous phase and/or the liquid phase is particularly preferably a gaseous phase and/or a liquid phase in at least one step selected from the group consisting of the reaction step (1) (e.g., a liquid reaction mixture and/or a gaseous phase in the reactor), the evaporation step (2) (in particular, a volatile phase), and the lower-boiling component-removing step (3) (in particular, an overhead from the splitter column). The gaseous phases and/or the liquid phases in these steps are preferred because at least one selected from hydrogen iodide, methyl iodide, methanol, and formaldehyde is more liable to be present in these steps.

Though a lower oxygen concentration is preferred, an excessively low oxygen concentration may cause the process unit and/or line to be corroded at a higher corrosion rate, due to an excessively strong reducing atmosphere. To eliminate or minimize this and to control the oxygen concentration in the process stream (gaseous phase and/or liquid phase), at least one oxygen source selected from the group consisting of oxygen-containing gases, oxygen-containing compounds, and oxygen generators may be introduced into the process, to thereby control the oxygen concentration in the gaseous phase and/or the liquid phase in the process stream.

A non-limiting example of the oxygen-containing gases is air; a non-limiting example of the oxygen-containing compounds is ozone; and non-limiting examples of the oxygen generators include peracetic acid and hydrogen peroxide. Each of different oxygen sources may be used alone or in combination.

The oxygen concentration in a process stream selected from a gaseous stream as a gaseous phase, and a liquid stream as a liquid phase may be typically about 0.25 mole or less (e.g., 0.2 mole or less), preferably about 0.1 mole or less (e.g., 0.05 mole or less), more preferably about 0.01 mole or less (e.g., $1\times10^{-3}$ mole or less), particularly preferably about $1\times10^{-4}$ mole or less (e.g., $1\times10^{-5}$ mole or less), and especially preferably $1\times10^{-6}$ mole or less (e.g., $1\times10^{-7}$ mole or less), per mole of the totality of hydrogen iodide and methyl iodide.

The proportion (ratio; $O_2/CO$) of oxygen to carbon monoxide in a gaseous phase and/or a liquid phase (e.g., in a gaseous phase) in at least one process stream selected from the group consisting of process unit streams and process line streams may be 7 percent by volume or less (e.g., 5 percent by volume or less), typically 2 percent by volume or less (e.g., 1 percent by volume or less), preferably 0.5 percent by volume or less (e.g., 0.1 percent by volume or less), more preferably 0.01 percent by volume or less (e.g., 0.001 percent by volume or less), and particularly preferably 0.0001 percent by volume or less (e.g., 0.00001 percent by volume or less).

The oxygen concentration in a liquid phase in a process stream is often low, and this may cause a large variation of the proportion ($O_2/CO$) of oxygen to carbon monoxide. The mass proportion ($O_2/CO$) of oxygen in the liquid phase, per 100 parts by mass of carbon monoxide, may be typically 1000 parts by mass or less (10 times or less) (e.g., 500 parts by mass or less), 250 parts by mass or less (e.g., 100 parts by mass or less), preferably 75 parts by mass or less (e.g., 50 parts by mass or less), and more preferably 20 parts by mass or less (e.g., 10 parts by mass or less); and may be 5 parts by mass or less (e.g., 1 part by mass or less), preferably 0.1 part by mass or less (e.g., 0.01 part by mass or less), more preferably 0.001 part by mass or less (e.g., 0.0001 part by mass or less), and particularly preferably 0.00005 part by mass or less (e.g., 0.00001 part by mass or less).

The percent by volume and the part by mass of each of the components may be calculated or converted mutually using an average molecular weight (weighted average molecular weight), as described later.

In addition, the method according to the present invention controls the formic acid concentration to 500 ppm by mass or less in a liquid phase in the acetic acid production process (in at least one process stream selected from the group consisting of process unit streams and process line streams). The formic acid concentration in a liquid phase in the process (a liquid phase in at least one stage of the process, and particularly preferably all liquid phases in the process) may be controlled to preferably 400 ppm by mass or less, more preferably 300 ppm by mass or less, furthermore preferably 200 ppm by mass or less, particularly preferably 100 ppm by mass or less, more preferably 50 ppm by mass or less, and still more preferably 30 ppm by mass or less.

The formic acid concentration in the liquid phase is not limited in its lower limit and may be typically 0.1 ppm by mass or more (e.g., 1 ppm by mass or more), preferably 3 ppm by mass or more (e.g., 5 ppm by mass or more), more preferably 10 ppm by mass or more, furthermore preferably 15 ppm by mass or more, and particularly preferably 20 ppm by mass or more, or may be zero (0), or equal to or less than the lower measurement limit.

With an increasing formic acid concentration in the liquid phase, formic acid is more liable to enter the acetic acid product. To eliminate or minimize this, a process stage (step) including a liquid phase to be controlled on formic acid concentration is preferably a process stage in which at least one of methanol and formaldehyde tends to be present. Specifically, the liquid phase is preferably a gaseous phase and/or a liquid phase in at least one step selected from the group consisting of: the reaction step (1); the steps included in the separation step (A) (the evaporation step (2) and the lower-boiling component-removing step (3)); the steps included in the purification section (4) (the dehydrating step (5), the higher-boiling component-removing step (6), and the rectifying step (7)); the steps included in the separation section (9) (the liquid-liquid separation step (10), the first acetaldehyde separation step (11), the extraction step (12), the second acetaldehyde separation step (13), and the alkane separation step (14)); and the steps included in the offgas treatment section (15) (the high-pressure absorbing step (16), the low-pressure absorbing step (17), and the stripping step (18)). In particular, the liquid phase is more preferably a gaseous phase and/or a liquid phase in at least one step selected from the group consisting of: the reaction step (1) (e.g., a liquid reaction mixture), the evaporation step (2) (in particular, a volatile phase), the lower-boiling component-removing step (3) (in particular, an overhead from the splitter column), the liquid-liquid separation step (10) (in particular, an upper phase and/or a lower phase), the high-pressure absorbing step (16), and the low-pressure absorbing step (17); and is furthermore preferably a gaseous phase and/or a liquid phase in at least one step selected from the group consisting of: the reaction step (1) (e.g., a liquid reaction mixture); the evaporation step (2) (in particular, a volatile phase); and the lower-boiling component-removing step (3) (in particular, an overhead from the splitter column).

The liquid phases in these steps are preferred because methanol and/or formaldehyde is still more liable to be present in these steps.

The process stage including the gaseous phase and/or the liquid phase to be controlled on oxygen concentration by at least one of the procedures (a) and (b) may be identical to or different from the process stage including the liquid phase to be controlled on formic acid concentration.

The present invention will be illustrated in further detail with reference to the attached drawings according to necessity. Each step, as well as a main device or unit for use in the corresponding step, may be indicated by the same reference sign.

A process illustrated in FIGS. 1 to 4 for continuously producing acetic acid includes (1) a reaction step (reaction system); and (A) a separation step. The reaction step (1) is the step of carbonylating methanol. The separation step (A) is the step of separating a reaction mixture resulting from the reaction step into a catalyst-containing stream, an acetic acid stream rich in acetic acid, and a stream rich in lower-boiling components as compared with the acetic acid stream, using at least one selected from the group consisting of evaporators and distillation columns. Specifically, the separation step (A) includes (2) an evaporation step (flash evaporation step or flash step); and (3) a lower-boiling component-removing step (first distillation step). The evaporation step (2) is the step of separating, through evaporation, the reaction mixture resulting from the reaction step into a volatile phase (2A) and a stream containing the catalyst (less-volatile phase) (2B). The lower-boiling component-removing step (3) is the step of distilling and separating the volatile phase (2A) into a first overhead (3A), an acetic acid stream rich in acetic acid (first acetic acid stream, crude acetic acid stream) (3B), and a bottom stream (higher-boiling component) (3C), where the first overhead (3A) is a stream rich in a lower-boiling component (e.g., at least one lower-boiling component selected from methyl iodide and acetaldehyde). The process further includes (4) a purification section or a group of purification steps (steps (5) to (8)); (9) a separation section or a group of separation steps (steps (10) to (14)); and (15) an offgas treatment section or a group of offgas treatment steps (steps (16) to (18)). The purification section (4) is a section of yielding a purified acetic acid from the acetic acid stream (3B). The separation section is a section of separating at least acetaldehyde from the first overhead (3A). The offgas treatment section (15) is a section of absorptively treating an offgas from the process with an absorbing solvent and separating the offgas into a stream rich in carbon monoxide, and a stream rich in acetic acid, methyl iodide, and methyl acetate.

In an embodiment, the lower-boiling component-removing step (3) in the method according to the present invention may be a step also having the function or functions of the dehydrating step (5) in the purification section (4) as described later, namely, the step (3) may be one step having functions of the two steps in combination (lower-boiling component-removing-dehydrating step). In an embodiment, the method according to the present invention may include, as the separation step (A), a single evaporating-lower-boiling component-removing step which is one step combining the evaporation step (2) and the lower-boiling component-removing step (3). Accordingly, the evaporating-lower-boiling component-removing step may be an evaporating-lower-boiling component-removing-dehydrating step which is a step also having the function or functions of the dehydrating step (5). Namely, the evaporating-lower-boiling component-removing step is the step of separating the reaction mixture resulting from the reaction step into the stream containing the catalyst, the stream rich in lower-boiling components, and the first acetic acid stream rich in acetic acid. The lower-boiling component-removing-dehydrating step is the step of distilling and separating the volatile phase resulting from the evaporation step into the stream rich in lower-boiling components, and the acetic acid stream rich in acetic acid. The acetic acid stream rich in acetic acid resulting from any of the lower-boiling component-removing-dehydrating step and the evaporating-lower-boiling component-removing-dehydrating step corresponds to a second acetic acid stream resulting from the dehydrating step (5). Accordingly, the acetic acid stream rich in acetic acid resulting from the separation step (A) may be a first acetic acid stream or a second acetic acid stream.

The reaction step (1), the evaporation step (2), and the lower-boiling component-removing step (3) are performed respectively in a reactor, an evaporator (flasher or catalyst-separating column), and a light ends column (first distillation column or splitter column). Accordingly, the acetic acid production equipment illustrated in FIGS. 1 to 4 includes the reactor, the evaporator, and the light ends column. When the process includes an evaporating-lower-boiling component-removing step, both the evaporation step (2) and the lower-boiling component-removing step (3) are performed in one tank or column (evaporating-light ends tank (or column)). When the lower-boiling component-removing step (3) is a lower-boiling component-removing-dehydrating step, both the lower-boiling component-removal and dehydration are performed in one column (splitter-dehydrating column), where the dehydration corresponds to the dehydrating step (5).

The process in the present invention may further include at least one section selected from the group consisting of the sections (4), (9), and (15), in addition to the steps (1) and (A). For example, the offgas treatment section (15) is not indispensable. In the offgas treatment section (15), the treatment may not necessarily be performed on offgases from all units or lines, but may be performed on an offgas from at least one process unit or line. The "gaseous phase" having the specific oxygen concentration in the process refers to a gaseous phase in at least one process stage (process unit and/or line), among all gaseous phases in the process. A gas constituting the gaseous phase is an offgas from the process, regardless of whether the gas is discharged out of the system. The gas (offgas) may be an "offgas" to be subjected to the offgas treatment step, or may be an "offgas" from at least one of all process units and process lines in the process. The steps will be individually illustrated in detail below.

(1) Reaction Step

In the reaction step (1), methanol and carbon monoxide are continuously fed respectively through a feed line 2 and a feed line 4 to a reactor (1) in the presence of a reaction medium containing a carbonylation catalytic system and water, to carbonylate methanol and to thereby form acetic acid. The carbon monoxide through the line 4 is mixed with hydrogen fed through a line 6, and fed as a gaseous mixture 7 to the reactor (1), where the hydrogen is fed so as to allow the catalyst to have higher activity. Methanol is not only fed to the reactor (1), but also added (fed) via a line 3 to a distillation column (5) in the dehydrating step (5). Carbon monoxide fed through a line 5 is mixed with a less-volatile phase (bottom catalyst liquid) in a recycle line 21 from an evaporator (2) in order to restrain precipitation of the catalyst. The mixed catalyst liquid is recycled via a line 22 to the reactor (1).

In addition, a portion 41 of an upper phase 38 and a portion (or a first portion) 40 of a lower phase 39 may also be recycled to the reactor (1), where the upper phase 38 and the lower phase 39 are liquid-liquid separated in a decanter S2 in the liquid-liquid separation step (10). The portion 41 is a portion of the upper phase, which is rich in acetic acid, methyl iodide, methyl acetate, and water. The portion 40 is a portion of the lower phase, which is rich in methyl iodide and methyl acetate. Another portion (or a second portion) 40 of the lower phase 39 may be subjected to the aftermentioned alkane separation step (14) (step of separating alkanes by distillation). A portion 54 of a condensate of a second overhead 51 from the distillation column (5) in the second distillation step (5) may also be mixed with the less-volatile phase (2B) (line 21) and recycled to the reactor (1), where the portion 54 is a portion of the condensate, which is rich in acetic acid.

As the methanol, fresh methanol may be fed directly or indirectly to the reactor (1), or methanol or a methanol derivative withdrawn from any of downstream steps may be recycled and fed to the reactor. Such material methanol is preferably methanol from which oxygen has been removed. The carbon monoxide may be used as a pure gas, or a gas diluted with an inert gas (such as nitrogen, helium, or carbon dioxide). Where necessary, an effluent gaseous component containing carbon monoxide resulting from any of downstream steps may be recycled to the reactor. Such carbon monoxide or effluent gaseous component for use herein is also carbon monoxide or an effluent gas from which oxygen has been removed.

In the following tables, $O_2$ represents oxygen, $H_2$ represents hydrogen, CO represents carbon monoxide, $CO_2$ represents carbon dioxide, $CH_4$ represents methane, $N_2$ represents nitrogen, AD represents acetaldehyde, MeOH represents methanol, MeI represents methyl iodide, MA represents methyl acetate, $H_2O$ represents water, AcOH represents acetic acid, HI represents hydrogen iodide, LiI represents lithium iodide, FrOH represents formic acid, PrOH represents propionic acid, DME represents dimethyl ether, AcA represents acetic anhydride, $(CH_3)_2C=O$ represents acetone, EtOH represents ethanol, EA represents ethyl acetate, EtI represents ethyl iodide, TOI represents total iodine compounds, and HexI represents hexyl iodide (hereinafter the same). The concentration of HI represents a concentration in terms of iodide ion. Metals are represented by atomic symbols.

For reference, an average molecular weight of a stream may be described in some of the tables. The average molecular weight is a weighted average value calculated on the basis of the molecular weight and proportion of each component contained in the stream. Assume that a gaseous-phase mixture has an average molecular weight (weighted average molecular weight) "A" and contains any component having a molecular weight "B". In this case, the percent by volume or percent by mass of the component can be calculated on the basis of the percent by mass or percent by volume of the component. Taking an oxygen concentration as an example, when a gaseous-phase mixture has an average molecular weight (weighted average molecular weight) A of 62.2, and oxygen is present in a measured percent by volume "D" of 7.0 percent by volume, the percent by mass "C" of oxygen can be calculated on the basis of oxygen molecular weight "B" of 32, according typically to the following equation: $(C(\times 100) \times A)/B = D(\times 100)$, as follows: $(C \times 62.2)/32 = 7$. Thus, the percent by mass "C" of oxygen is calculated as 3.6 percent by mass. The percent by mass and percent by volume of each component in the gaseous-phase mixture can be calculated according to the equation in the above manner. Accordingly, the following tables give component concentrations in percent by mass alone.

Assume that a sample (gaseous phase and liquid phase) contain a gaseous component, other than oxygen, having a concentration of less than the detection limit. In this case, the concentration of the gaseous component in the sample may be determined by forming a concentrate by a procedure similar to that for the oxygen concentration, measuring the concentration of the gaseous component in the concentrate, and converting the measured value into the concentration of the gaseous component in the sample.

Also assume that a sample (gaseous phase and liquid phase) contains any component having a concentration of less than the detection limit (e.g., less than 0.1 ppb for a metal component; and less than 1 ppm for an organic substance). In this case, the concentration of the component may be determined by forming a concentrate in which the component is enriched (concentrated), measuring the concentration of the component in the concentrate, and converting the measured value into the concentration of the component in the sample. Assume that a sample contains a component whose concentration is unmeasurable. In this case, the concentration of the component may be estimated according to distillation calculation and entrainment by evaporation. For example, with respect to amounts of entrainment in adjacent plates in an evaporation operation or an operation of a distillation column, the concentration in a higher plate corresponds to about 1 to about 20 percent by mass of the concentration in a lower plate; and the concentration of a metal in a liquid in a higher plate corresponds to about 1 to about 20 percent by mass of the concentration of the metal in a liquid in an adjacent lower plate. The concentration of the metal may be calculated on the basis of such estimated value.

An inert gas may be introduced into the process. For example, an inert gas (such as nitrogen gas ($N_2$)) may be fed to a process unit (such as a distillation column) to regulate the inside pressure of the unit; and/or purge with an inert gas (such as nitrogen gas) to a measuring instrument (such as a pressure gauge, a thermometer, or a level gauge) may be performed so as to eliminate or minimize contamination of the measuring instrument with an organic vapor. Another inert gas (such as carbon monoxide gas CO) may be introduced instead of the nitrogen gas. A component such as water, an alkali metal compound, or a methanol source may be introduced to a process unit and line. In any of such cases, the concentration of a feed component (for example, the composition of a gas (e.g., an inert gas such as nitrogen gas or carbon monoxide gas)) in the following tables drastically increases or varies depending on the feed component (such as an inert gas) and the amount thereof, where the tables present a composition in the process unit and line.

For example, the material methanol (line 2) may have a composition (in percent by mass) typically as follows:

TABLE 1

|  | Range | Preferred range | More preferred range |
|---|---|---|---|
| O$_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| H$_2$ | 0% to 1% (e.g., 1 ppt to 0.1%) | 10 ppt to 0.01% | 100 ppt to 0.001% |
| CO | 0% to 1% (e.g., 1 ppt to 0.1%) | 10 ppt to 0.01% | 100 ppt to 0.001% |
| CO$_2$ | 0% to 1% (e.g., 1 ppt to 0.1%) | 10 ppt to 0.01% | 100 ppt to 0.001% |
| CH$_4$ | 0% to 1% (e.g., 1 ppt to 0.1%) | 10 ppt to 0.01% | 100 ppt to 0.001% |
| N$_2$ | 0% to 1% (e.g., 1 ppt to 0.1%) | 10 ppt to 0.01% | 100 ppt to 0.001% |
| AD | 0% to 1% (e.g., 1 ppb to 0.1%) | 10 ppb to 0.01% | 100 ppb to 0.001% |
| MeOH | 95% to 100% | 98% to 99.999% | 99% to 99.99% |
| MeI | 0% to 1% (e.g., 1 ppt to 0.1%) | 10 ppt to 0.01% | 100 ppt to 0.001% |
| MA | 0% to 1% (e.g., 1 ppb to 0.1%) | 10 ppb to 0.01% | 100 ppb to 0.001% |
| H$_2$O | 1 ppm to 0.1% | 10 ppm to 0.05% | 100 ppm to 0.01% |
| AcOH | 0% to 1% (e.g., 1 ppb to 0.1%) | 10 ppb to 0.01% | 100 ppb to 0.001% |
| HI | 0% to 1% (e.g., 0.1 ppb to 0.5%) | 1 ppb to 0.1% | 10 ppb to 100 ppm |
| FrOH | 0% to 1% (e.g., 1 ppm to 0.1%) | 5 to 100 ppm | 10 to 30 ppm |
| PrOH | 0% to 1% (e.g., 0.1 ppm to 0.1%) | 1 to 100 ppm | 10 to 30 ppm |
| DME | 0% to 1% (e.g., 1 ppb to 100 ppm) | 10 ppb to 30 ppm | 100 ppb to 5 ppm |
| AcA | 0% to 1% (e.g., 1 ppb to 0.1%) | 10 ppb to 100 ppm | 100 ppb to 50 ppm |
| (CH$_3$)$_2$C=O | 0% to 1% (e.g., 1 ppb to 100 ppm) | 10 ppb to 50 ppm | 100 ppb to 30 ppm |
| EtOH | 0% to 1% (e.g., 1 ppb to 100 ppm) | 10 ppb to 50 ppm | 100 ppb to 10 ppm |
| EA | 0% to 1% (e.g., 1 ppb to 100 ppm) | 10 ppb to 50 ppm | 100 ppb to 10 ppm |
| EtI | 0% to 1% (e.g., 1 ppb to 100 ppm) | 10 ppb to 50 ppm | 100 ppb to 10 ppm |
| Li | 0% to 0.1% (e.g., 0.01 ppt to 100 ppb) | 1 ppt to 10 ppb | 10 ppt to 1 ppb |
| Rh | 0% to 0.1% (e.g., 0.01 ppt to 100 ppb) | 1 ppt to 10 ppb | 10 ppt to 1 ppb |
| Fe | 0% to 0.1% (e.g., 1 ppt to 1 ppm) | 10 ppt to 0.5 ppm | 100 ppt to 0.1 ppm |
| Ni | 0% to 0.1% (e.g., 1 ppt to 1 ppm) | 10 ppt to 0.5 ppm | 100 ppt to 0.1 ppm |
| Cr | 0% to 0.1% (e.g., 1 ppt to 1 ppm) | 10 ppt to 0.5 ppm | 100 ppt to 0.1 ppm |
| Mo | 0% to 0.1% (e.g., 1 ppt to 1 ppm) | 10 ppt to 0.5 ppm | 100 ppt to 0.1 ppm |
| Zn | 0% to 0.1% (e.g., 1 ppt to 1 ppm) | 10 ppt to 0.5 ppm | 100 ppt to 0.1 ppm |
| Cu | 0% to 0.1% (e.g., 1 ppt to 1 ppm) | 10 ppt to 0.5 ppm | 100 ppt to 0.1 ppm |

The material carbon monoxide (lines 4 and 5) may have a composition (in percent by mass) typically as follows:

TABLE 2

|  | Range | Preferred range | More preferred range |
|---|---|---|---|
| O$_2$ | 10% or less (e.g., 0.1 ppb to 10%), e.g., 0.2 ppb to 3.6% (e.g., 1 ppb to 2%), or less than 7% (e.g., 0.1 ppb to 5%), e.g., 1 ppb to 3% (e.g., 10 ppb to 1%) | 2 ppb to 1% (e.g., 10 ppb to 0.1%), or 20 ppb to 5000 ppm | 50 ppb to 500 ppm (e.g., 100 ppb to 100 ppm), or 50 ppb to 1000 ppm |
| H$_2$ | 0% to 1% (e.g., 1 ppt to 0.1%) | 10 ppt to 0.01% | 100 ppt to 0.001% |
| CO | 95% to 100% | 98% to 99.999% | 99% to 99.99% |
| CO$_2$ | 0% to 1% (e.g., 1 ppt to 0.1%) | 10 ppt to 0.01% | 100 ppt to 0.001% |
| CH$_4$ | 0% to 1% (e.g., 1 ppt to 0.1%) | 10 ppt to 0.01% | 100 ppt to 0.001% |
| N$_2$ | 0% to 1% (e.g., 1 ppt to 0.1%) | 10 ppt to 0.01% | 100 ppt to 0.001% |
| AD | 0% to 1% (e.g., 1 ppb to 0.1%) | 10 ppb to 0.01% | 100 ppb to 0.1 ppm |
| MeOH | 0% to 1% (e.g., 1 ppb to 0.1%) | 10 ppb to 0.01% | 100 ppb to 0.1 ppm |
| MeI | 0% to 1% (e.g., 1 ppt to 0.1 %) | 10 ppt to 0.01% | 100 ppt to 0.1 ppm |
| MA | 0% to 1% (e.g., 1 ppb to 0.1%) | 10 ppb to 0.01% | 100 ppb to 0.1 ppm |
| H$_2$O | 0% to 1% (e.g., 1 ppm to 0.1%) | 10 ppm to 0.05% | 20 ppm to 0.01% |
| AcOH | 0% to 1% (e.g., 1 ppb to 0.1%) | 10 ppb to 0.01% | 100 ppb to 0.1 ppm |
| FrOH | 0% to 1% (e.g., 1 ppm to 0.1%) | 5 to 100 ppm | 10 to 50 ppm |
| PrOH | 0% to 1% (e.g., 1 ppb to 0.1%) | 1 to 100 ppm | 10 to 50 ppm |
| DME | 0% to 0.1% (e.g., 1 ppb to 100 ppm) | 10 ppb to 30 ppm | 100 ppb to 0.1 ppm |
| (CH$_3$)$_2$C=O | 0% to 1% (e.g., 1 ppb to 100 ppm) | 10 ppb to 50 ppm | 100 ppb to 0.1 ppm |
| EtOH | 0% to 1% (e.g., 1 ppb to 100 ppm) | 10 ppb to 50 ppm | 100 ppb to 0.1 ppm |
| EA | 0% to 1% (e.g., 1 ppb to 100 ppm) | 10 ppb to 50 ppm | 100 ppb to 0.1 ppm |
| EtI | 0% to 1% (e.g., 1 ppb to 100 ppm) | 10 ppb to 50 ppm | 100 ppb to 0.1 ppm |

The composition of the gaseous mixture (line 7) may typically be approximately identical to or similar to the composition of the material carbon monoxide (lines 4 and 5). A component proportion (content of each component) in the composition of the gaseous mixture (line 7) may be determined by weighted-averaging the corresponding component proportion of the material carbon monoxide (lines 4 and 5) and the component proportion of hydrogen (line 6).

The carbonylation catalytic system generally includes a metal catalyst, a catalyst stabilizer or reaction accelerator, and/or, a promoter (co-catalyst). Non-limiting examples of the metal catalyst include cobalt catalysts, rhodium catalysts, and iridium catalyst. The catalytic system may include each of different metal catalysts alone or in combination. The metal catalyst is preferably selected from rhodium catalysts and iridium catalysts, and particularly preferably selected from rhodium catalysts.

The metal catalyst may be used in the form typically of an elementary metal; as well as a metal oxide (including a composite metal oxide), a metal hydroxide, a metal iodide, a metal carboxylate (such as an acetate), a metal inorganic acid salt (such as a sulfate, a nitrate, or a phosphate), or a metal complex. The metal catalyst is preferably used in such a form as to be soluble in a liquid phase (reaction liquid or reaction medium), such as the form of a complex. Preferred, but non-limiting examples of the rhodium catalysts include rhodium-iodine complexes such as $RhI_3$, $[RhI_2(CO)_4]^-$, and $[Rh(CO)_2I_2]^-$; and rhodium-carbonyl complexes.

Non-limiting examples of the catalyst stabilizer or reaction accelerator include ionic metal iodides capable of forming an iodine ion in the reaction liquid, such as alkali metal iodides (e.g., lithium iodide, sodium iodide, and potassium iodide); of which lithium iodide is preferred. In addition to lithium iodide and analogous compounds, non-limiting examples of the catalyst stabilizer or reaction accelerator also include metal compounds (such as metal iodides and metal complexes) of transition metals (including metals or corrosion-derived metals present in the reaction system, as indicated in the following tables). Non-limiting examples of the transition metals include, of the periodic table, Group 6 elements such as molybdenum, chromium, and tungsten; Group 7 elements such as manganese, and rhenium; Group 8 elements such as iron, ruthenium, and osmium; Group 9 elements such as cobalt, rhodium, and iridium; Group 10 elements such as nickel; Group 11 elements such as copper; Group 12 elements such as cadmium and zinc; and Group 13 elements such as gallium and indium. The catalytic system may include each of different catalyst stabilizers or reaction accelerators alone or in combination, according to the type of the metal catalyst. An iridium catalytic system does not necessarily require an alkali metal iodide. The metal component in the catalyst stabilizer or reaction accelerator is preferably selected from ruthenium, indium, and osmium. A non-limiting example of the promoter for use herein is methyl iodide.

The carbonylation catalytic system preferably includes a rhodium catalyst and methyl iodide as a promoter, and more preferably includes a rhodium catalyst, a metal iodide (such as lithium iodide) as a catalyst stabilizer, and methyl iodide as a promoter. To the reactor, water and a catalyst mixture (catalyst liquid) containing the carbonylation catalytic system may be fed. It is preferred that oxygen has been removed from the catalyst mixture and water typically by heating or boiling.

The carbon monoxide partial pressure in the reactor may be typically about 2 to about 30 atmospheres, and preferably about 4 to about 15 atmospheres. The carbonylation gives hydrogen as a result of the reaction between carbon monoxide and water. The hydrogen increases the catalytic activity. Thus, hydrogen may be fed to the reactor according to necessity. Hydrogen may also be fed to the reactor by recycling gaseous components (including hydrogen, carbon monoxide, and other gases) discharged from the downstream step(s), where necessary after purifying the gaseous components. As such hydrogen, hydrogen having a lower oxygen concentration is preferably used. The hydrogen partial pressure in the reaction system may be typically about 0.5 to about 250 kPa (e.g., about 1 to about 200 kPa), preferably about 5 to about 150 kPa, and more preferably about 10 to about 100 kPa (e.g., about 10 to about 50 kPa), in terms of absolute pressure.

The carbonylation may be performed at a temperature of typically about 150° C. to about 250° C., preferably about 160° C. to about 230° C., and more preferably about 170° C. to about 220° C. and at a pressure (total reaction pressure), including the partial pressures of by-products, typically about 15 to about 40 atmospheres. The space time yield of acetic acid in the reaction system may be typically about 5 to about 50 mol/Lh, preferably about 8 to about 40 mol/Lh, and more preferably about 10 to about 30 mol/Lh.

In the reactor, the methanol carbonylation proceeds with an equilibrium between a liquid phase reaction system and a gaseous phase system. The liquid phase reaction system includes the reaction component(s) and the metal catalyst component. The gaseous phase system includes, for example, carbon monoxide; reaction by-products such as hydrogen, methane, and carbon dioxide; vaporized lower-boiling components such as methyl iodide, a product acetic acid, and methyl acetate.

The metal catalyst in the liquid phase may be present in a concentration of typically about 100 to about 5000 ppm by mass, preferably about 200 to about 3000 ppm by mass, more preferably about 300 to about 2000 ppm by mass, and particularly preferably about 500 to about 1500 ppm by mass, of the totality of the liquid phase in the reactor. The catalyst stabilizer or reaction accelerator may be present in the liquid phase in a concentration of typically about 1 to about 25 percent by mass, preferably about 2 to about 22 percent by mass, and more preferably about 3 to about 20 percent by mass, of the totality of the liquid phase in the reactor. The iodide ion in the reaction system may be present in a concentration of typically 0.05 to 2.5 mol/L, and preferably 0.25 to 1.5 mol/L. The methyl iodide is present in a concentration of typically about 1 to about 30 percent by mass, preferably about 5 to about 25 percent by mass, and more preferably about 6 to about 20 percent by mass (e.g., about 8 to about 18 percent by mass), of the totality of the liquid phase in the reactor.

The reaction mixture (crude reaction liquid or reaction medium) generally contains the product acetic acid; methyl acetate, which results from the reaction between the product acetic acid and the material methanol; and water. The acetic acid also serves as a solvent. The reaction mixture generally further contains unreacted material methanol. The methyl acetate in the reaction mixture may be present in a proportion of about 0.1 to about 30 percent by mass, preferably about 0.3 to about 20 percent by mass, and more preferably about 0.5 to about 10 percent by mass (e.g., about 0.5 to about 6 percent by mass), of the totality of the reaction mixture. The water concentration in the reaction mixture may be low; is typically about 0.1 to about 15 percent by mass, preferably about 0.5 to about 10 percent by mass, and more preferably about 0.8 to about 5 percent by mass (e.g., about 1 to about 3 percent by mass); and may be about 1 to about 10 percent by mass (e.g., about 2 to about 5 percent by mass), of the totality of the reaction mixture.

The reaction mixture also contains various by-products such as acetaldehyde, and by-products derived from acetaldehyde. According to the present invention, acetaldehyde can be effectively removed by the separation section (9), and this can lower the acetaldehyde concentration in the reactor and can significantly restrain the formation of acetaldehyde-derived by-products, even in a continuous reaction. The reaction mixture in the reactor may have an acetaldehyde concentration of typically about 1500 ppm by mass or less, typically about 10 to about 1000 ppm by mass, preferably about 50 to about 500 ppm by mass, and more preferably about 100 to about 400 ppm by mass.

Non-limiting examples of the acetaldehyde-derived by-products (derivatives from acetaldehyde), which may be by-produced in the reaction, include aldehydes such as butyraldehyde, crotonaldehyde, 2-ethylcrotonaldehyde, and 2-ethylbutyraldehyde; ketones such as acetone and methyl ethyl ketone; aldol condensation products of them; and $C_2$-$C_{12}$ alkyl iodides such as ethyl iodide, propyl iodide, butyl iodide, pentyl iodide, and hexyl iodide. Examples of such by-products also include linear or branched carboxylic acids including formic acid, and carboxylic acids containing 3 or more carbon atoms, exemplified by $C_3$-$C_{12}$ alkanecarboxylic acids such as propionic acid, butanoic acid, pentanoic acid, hexanoic acid, heptanoic acid, and octanoic acid, as well as higher fatty acids containing 9 or more carbon atoms; alkyl alcohols including $C_3$-$C_{12}$ alkyl alcohols such as ethanol, butyl alcohol, 2-ethylbutyl alcohol, hexyl alcohol, heptyl alcohol, and octyl alcohol, as well as alkyl alcohols containing 9 or more carbon atoms; hydrocarbons containing 2 or more carbon atoms, such as $C_2$-$C_{12}$ alkanes. Examples of the by-products, which may be formed in the liquid phase system, also include ethyl acetate and other esters between methanol or any of the alkyl alcohols with acetic acid or any of the carboxylic acids; and dimethyl ether and other dialkyl ethers. The concentration of these by-products in the entire process including the liquid phase system may be about 0.1 ppb by mass to about 100 ppm by mass (e.g., about 0.5 ppb by mass to about 50 ppm by mass), and preferably about 1 ppb by mass to about 10 ppm by mass (e.g., about 2 ppb by mass to about 1 ppm by mass). Thus, the concentration of these by-products may be omitted from the description or indication in the steps mentioned later.

The concentration of hexyl iodide and other alkyl iodides containing 2 or more carbon atoms may be typically about 0.1 ppb by mass to about 1 ppm by mass (e.g., about 0.5 to about 500 ppb by mass), and preferably about 1 ppb by mass to about 100 ppb by mass. The concentration of propionic acid and other alkanecarboxylic acids may be typically about 0.1 to about 500 ppm by mass (e.g., about 1 to about 500 ppm by mass), and preferably about 3 to about 100 ppm by mass.

The concentration of dimethyl ether (DME) may be 0.5 percent by mass or less (e.g., about 0.1 to about 1000 ppm by mass), preferably about 1 to about 500 ppm by mass (e.g., about 2 to about 300 ppm by mass), and more preferably about 3 to about 200 ppm by mass (e.g., about 5 to about 100 ppm by mass).

In addition, 3-hydroxyalkanals (such as 3-hydroxybutanal) may also be by-produced. The content of the 3-hydroxyalkanals in the reaction mixture may be 100 ppm by mass or less (e.g., about 0.1 ppb by mass to about 100 ppm by mass), and preferably about 0.5 ppb by mass to about 50 ppm by mass. These by-products are often by-produced in a concentration proportional to the second to third power of the acetaldehyde concentration.

Acetaldehyde and the acetaldehyde-derived by-products (such as aldehydes, ketones, and aldol condensation products) belong to permanganate reducing compounds (PRC's). Thus, it is preferred to separate and remove acetaldehyde, which is a main by-product, from the reaction mixture and to recover useful components (such as methyl iodide) from the process stream(s) for effective utilization. Although the $C_2$-$C_{12}$ alkyl iodides, such as methyl iodide, also belong to the PRC's, methyl iodide is excluded from the PRC's in this description.

The reaction mixture also contains metals resulting from corrosion, such as iron, nickel, chromium, molybdenum, cobalt, and zirconium. The reaction mixture may have a content of each of the corrosion-derived metals of about 2000 ppm by mass or less (e.g., about 1 to about 1000 ppm by mass). The reaction mixture may have a total content of the corrosion-derived metals of about 10000 ppm by mass or less (e.g., about 5 to about 5000 ppm by mass). A liquid stream downstream from the reaction mixture may contain such corrosion-derived metals in a content approximately identical to or similar to the above content. Thus, the concentrations of the corrosion-derived metals in the liquid stream are omitted from the description or indication of the steps.

As described above, the reaction mixture contains acetic acid; lighter (lower-boiling) components or impurities each having a lower boiling point as compared with acetic acid, such as methyl iodide, methyl acetate, water, and acetaldehyde; and heavier (higher-boiling) components or impurities each having a higher boiling point as compared with acetic acid, which are exemplified by metal catalyst components such as a rhodium catalyst; lithium iodide as a catalyst stabilizer; and propionic acid and other $C_3$-$C_{12}$ alkanecarboxylic acids. In the acetic acid production process, a purified acetic acid is produced by removing impurities from the reaction mixture.

Since the methanol carbonylation is an exothermic reaction system with heat output, the reaction temperature may be controlled typically by recycling the condensate after cooling or heat removal, and/or by using a heat-removing unit or cooling unit (such as a jacket). To remove a part of the reaction heat, it is acceptable that a vapor component (vent gas) from the reactor is cooled typically using a condenser or a thermal converter, and separated into a liquid component and a gaseous component, and at least one of the liquid component and the gaseous component is recycled to the reactor.

A gaseous phase (line 8) from the reactor (1) is cooled and condensed in a condenser to form a condensate 10 and a non-condensable gas 9, where the non-condensable gas 9 contains a relatively large amount of carbon monoxide. The condensate 10 is returned to the reactor (1). The non-condensable gas 9 is introduced into a gas-liquid separation pot or buffer tank S1. A non-condensable gas (an offgas rich in carbon monoxide and methyl iodide) 11 from the tank is treated in the offgas treatment section (15) (typically in a high-pressure absorber (16)). Specifically, at least a portion of the non-condensable gas (offgas) 11, which generally contains carbon monoxide, is treated in the offgas treatment section (15). Another portion of the non-condensable gas (offgas) can be introduced via a line 172 to the evaporator (2) (introduced into a liquid phase or volatile phase (gas) in the flasher) to stabilize the catalyst in the evaporator (2) (to eliminate or minimize the precipitation of the metal catalyst (such as a rhodium catalyst)).

A mixture of the gaseous phase (gaseous phase portion or gaseous stream) (line 8) from the reactor may have a composition typically as follows.

Assume that a gaseous-phase mixture has an average molecular weight (weighted average molecular weight) "A" and contains a component having a molecular weight "B". In this case, the percent by volume or percent by mass of the component can be calculated on the basis of the percent by mass or percent by volume of the component. Taking an oxygen concentration as an example, assume that the gaseous-phase mixture has an average molecular weight "A" of 62.2, and oxygen is present in a measured percent by volume "D" of 7.0 percent by volume. In this case, the percent by mass "C" of oxygen can be calculated on the basis of the oxygen molecular weight "B" of 32, typically according to the following equation: $(C(\times 100) \times A)/B = D(\times 100)$ as $(C \times 62.2)/32 = 7$, from which the oxygen percent by mass "C" is calculated as 3.6 percent by mass. Thus, the percent by mass and percent by volume of each component in the gaseous-phase mixture can be calculated according to the equation. Accordingly, the tables indicate component concentrations in percent by mass alone.

TABLE 3

| Average molecular weight: 62.62 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 5% (e.g., 0.01% to 5%) | 20 ppb to 2% (e.g., 30 ppb to 1%) | 100 ppb to 0.1% (e.g., 1 to 100 ppm) |
| CO | 0.1% to 70% (e.g., 1% to 50%) | 3% to 30% | 7% to 20% |
| $CO_2$ | 0% to 5% (e.g., 0.01% to 5%) | 0.05% to 2% | 0.1% to 1% |
| $CH_4$ | 0% to 5% (e.g., 0.01% to 5%) | 0.05% to 3% | 0.1% to 2% |
| $N_2$ | 0% to 5% (e.g., 0.01% to 5%) | 0.05% to 3% | 0.1% to 2% |
| AD | 0.001% to 5% | 0.01% to 2% | 0.02% to 1% |
| MeOH | 0.1 ppm to 1% | 1 ppm to 0.5% | 10 ppm to 0.1% |
| MeI | 1% to 95% (e.g., 5% to 90%) | 10% to 80% | 20% to 70% |
| MA | 0.1% to 15% | 0.5% to 10% | 1% to 7% |
| $H_2O$ | 0.1% to 15% | 0.5% to 10% | 1% to 7% |
| AcOH | 1% to 50% | 2% to 40% | 5% to 30% |
| FrOH | 0% to 1% (e.g., 0.01 ppm to 1%) | 0.1 ppm to 0.5% | 1 ppm to 0.1% |
| PrOH | 0% to 1% (e.g., 0.01 ppm to 1%) | 0.01 ppm to 0.5% | 0.1 ppm to 0.1% |
| DME | 0% to 1% (e.g., 0.1 ppm to 1%) | 1 ppm to 0.5% | 10 ppm to 0.2% |
| $(CH_3)_2C=O$ | 0% to 1% (e.g., 0.1 ppm to 1%) | 1 ppm to 0.5% | 10 ppm to 0.2% |
| EtOH | 0% to 1% (e.g., 0.1 ppm to 1%) | 1 ppm to 0.5% | 10 ppm to 0.2% |
| EA | 0% to 1% (e.g., 0.1 ppm to 1%) | 1 ppm to 0.5% | 10 ppm to 0.2% |
| EtI | 0% to 1% (e.g., 0.1 ppm to 1%) | 1 ppm to 0.5% | 10 ppm to 0.2% |
| LiI | 0% to 0.1% (e.g., 1 ppt to 100 ppm) | 10 ppt to 10 ppm | 100 ppt to 1 ppm |
| Rh | 0% to 0.1% (e.g., 1 ppt to 100 ppm) | 10 ppt to 10 ppm | 100 ppt to 1 ppm |
| Fe | 0% to 0.1% (e.g., 1 ppt to 100 ppm) | 10 ppt to 10 ppm | 100 ppt to 1 ppm |
| Ni | 0% to 0.1% (e.g., 1 ppt to 10 ppm) | 10 ppt to 1 ppm | 100 ppt to 0.1 ppm |
| Cr | 0% to 0.1% (e.g., 1 ppt to 10 ppm) | 10 ppt to 1 ppm | 100 ppt to 0.1 ppm |
| Mo | 0% to 0.1% (e.g., 1 ppt to 10 ppm) | 10 ppt to 1 ppm | 100 ppt to 0.1 ppm |
| Zn | 0% to 0.1% (e.g., 1 ppt to 10 ppm) | 10 ppt to 1 ppm | 100 ppt to 0.1 ppm |
| Cu | 0% to 0.1% (e.g., 1 ppt to 10 ppm) | 10 ppt to 1 ppm | 100 ppt to 0.1 ppm |

The condensate 10 from the condenser may have a composition typically as follows.

TABLE 4

| Average molecular weight: 88.44 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.01 ppm to 1%) | 0.1 ppm to 0.1% | 1 ppm to 0.01% |
| CO | 0% to 2% (e.g., 1 ppm to 2%) | 10 ppm to 1% | 100 ppm to 0.5% |
| $CO_2$ | 0% to 1% (e.g., 0.1 ppm to 1%) | 1 ppm to 0.5% | 10 ppm to 0.2% |
| $CH_4$ | 0% to 1% (e.g., 0.1 ppm to 0.1%) | 1 ppm to 0.05% | 10 ppm to 0.01% |
| $N_2$ | 0% to 1% (e.g., 0.1 ppm to 0.1%) | 1 ppm to 0.05% | 10 ppm to 0.01% |
| AD | 0% to 1% (e.g., 1 ppm to 1%) | 10 ppm to 0.5% | 50 ppm to 0.2% |
| MeOH | 0% to 1% (e.g., 1 ppm to 1%) | 10 ppm to 0.5% | 50 ppm to 0.2% |
| MeI | 1% to 95% | 5% to 90% | 10% to 80% |
| MA | 0.1% to 20% | 0.5% to 10% | 1% to 5% |
| $H_2O$ | 0.1% to 20% | 0.5% to 10% | 1% to 7% |
| AcOH | 1% to 50% | 3% to 40% | 5% to 30% |
| FrOH | 0% to 1% (e.g., 1 ppm to 1%) | 5 ppm to 0.1% | 10 ppm to 0.01% |
| PrOH | 0% to 1% (e.g., 0.1 ppm to 1%) | 0.5 ppm to 0.1% | 1 ppm to 0.01% |
| DME | 0% to 2% (e.g., 1 ppm to 2%) | 5 ppm to 0.5% | 10 ppm to 0.1% |
| $(CH_3)_2C{=}O$ | 0% to 2% (e.g., 1 ppm to 2%) | 5 ppm to 0.5% | 10 ppm to 0.1% |
| EtOH | 0% to 2% (e.g., 1 ppm to 2%) | 5 ppm to 0.5% | 10 ppm to 0.1% |
| EA | 0% to 2% (e.g., 1 ppm to 2%) | 5 ppm to 0.5% | 10 ppm to 0.1% |
| EtI | 0% to 2% (e.g., 1 ppm to 2%) | 5 ppm to 0.5% | 10 ppm to 0.1% |
| LiI | 0% to 0.1% (e.g., 1 ppt to 100 ppm) | 10 ppt to 10 ppm | 100 ppt to 1 ppm |
| Rh | 0% to 0.1% (e.g., 1 ppt to 100 ppm) | 10 ppt to 10 ppm | 100 ppt to 1 ppm |
| Fe | 0% to 0.1% (e.g., 1 ppt to 100 ppm) | 10 ppt to 10 ppm | 100 ppt to 1 ppm |
| Ni | 0% to 0.1% (e.g., 1 ppt to 10 ppm) | 10 ppt to 1 ppm | 100 ppt to 0.1 ppm |
| Cr | 0% to 0.1% (e.g., 1 ppt to 10 ppm) | 10 ppt to 1 ppm | 100 ppt to 0.1 ppm |
| Mo | 0% to 0.1% (e.g., 1 ppt to 10 ppm) | 10 ppt to 1 ppm | 100 ppt to 0.1 ppm |
| Zn | 0% to 0.1% (e.g., 1 ppt to 10 ppm) | 10 ppt to 1 ppm | 100 ppt to 0.1 ppm |
| Cu | 0% to 0.1% (e.g., 1 ppt to 10 ppm) | 10 ppt to 1 ppm | 100 ppt to 0.1 ppm |

The non-condensable gas 9 from the condenser may have a composition typically as follows.

The non-condensable gas (offgas) 11 from the tank S1 may have a composition approximately identical to or similar to the composition of the non-condensable gas 9 from the condenser.

TABLE 5

| Average molecular weight: 29.86 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 10% (e.g., 0.1 ppm to 10%) | 1 ppm to 5% | 10 ppm to 2% |
| CO | 1% to 99% | 5% to 90% | 10% to 85% |

TABLE 5-continued

| Average molecular weight: 29.86 | Range | Preferred range | More preferred range |
|---|---|---|---|
| $CO_2$ | 0.01% to 5% | 0.1% to 3% | 0.2% to 2% |
| $CH_4$ | 0.1% to 15% | 0.5% to 10% | 1% to 6% |
| $N_2$ | 0.1% to 20% | 0.5% to 15% | 1% to 10% |
| AD | 0% to 1% (e.g., 0.001% to 1%) | 0.01% to 0.5% | 0.02% to 0.2% |
| MeOH | 0% to 1% (e.g., 1 ppm to 1%) | 5 ppm to 0.5% | 10 ppm to 0.1% |
| MeI | 1% to 90% (e.g., 5% to 80%) | 10% to 70% | 20% to 50% |
| MA | 0% to 5% (e.g., 0.001% to 5%) | 0.01% to 1% | 0.05% to 0.5% |
| $H_2O$ | 0% to 5% (e.g., 0.001% to 5%) | 0.01% to 1% | 0.05% to 0.5% |
| AcOH | 0% to 5% (e.g., 0.001% to 5%) | 0.01% to 1% | 0.05% to 0.5% |
| FrOH | 0% to 1% (e.g., 0.1 ppm to 0.5%) | 1 ppm to 0.2% | 10 ppm to 0.1% |
| PrOH | 0% to 1% (e.g., 0.1 ppm to 0.5%) | 0.5 ppm to 0.2% | 1 ppm to 0.1% |
| DME | 0% to 1% (e.g., 0.1 ppm to 0.5%) | 1 ppm to 0.2% | 10 ppm to 0.1% |
| $(CH_3)_2C{=}O$ | 0% to 1% (e.g., 0.1 ppm to 1%) | 1 ppm to 0.1% | 5 ppm to 0.05% |
| EtOH | 0% to 1% (e.g., 0.1 ppm to 1%) | 1 ppm to 0.1% | 5 ppm to 0.05% |
| EA | 0% to 1% (e.g., 0.1 ppm to 1%) | 1 ppm to 0.1% | 5 ppm to 0.05% |
| EtI | 0% to 1% (e.g., 0.1 ppm to 1%) | 1 ppm to 0.1% | 5 ppm to 0.05% |
| LiI | 0% to 0.1% (e.g., 1 ppt to 10 ppm) | 10 ppt to 1 ppm | 100 ppt to 0.1 ppm |
| Rh | 0% to 0.1% (e.g., 1 ppt to 10 ppm) | 10 ppt to 1 ppm | 100 ppt to 0.1 ppm |
| Fe | 0% to 0.1% (e.g., 1 ppt to 10 ppm) | 10 ppt to 1 ppm | 100 ppt to 0.1 ppm |
| Ni | 0% to 0.1% (e.g., 1 ppt to 1 ppm) | 10 ppt to 0.1 ppm | 100 ppt to 0.01 ppm |
| Cr | 0% to 0.1% (e.g., 1 ppt to 1 ppm) | 10 ppt to 0.1 ppm | 100 ppt to 0.01 ppm |
| Mo | 0% to 0.1% (e.g., 1 ppt to 1 ppm) | 10 ppt to 0.1 ppm | 100 ppt to 0.01 ppm |
| Zn | 0% to 0.1% (e.g., 1 ppt to 1 ppm) | 10 ppt to 0.1 ppm | 100 ppt to 0.01 ppm |
| Cu | 0% to 0.1% (e.g., 1 ppt to 1 ppm) | 10 ppt to 0.1 ppm | 100 ppt to 0.01 ppm |

The reaction mixture 12 from the reactor (1) is introduced or fed via a line 12 to the evaporator (2) for flash evaporation, and is separated into a volatile phase (2A) and a less-volatile phase (2B). The volatile phase (2A) includes product acetic acid as well as other components such as methyl iodide, acetaldehyde, methyl acetate, and water. The less-volatile phase (2B) includes the rhodium catalyst and lithium iodide.

The reaction mixture 12 may have a composition typically as follows.

TABLE 6

| Average molecular weight: 65.23 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.1 ppm to 1%) | 1 ppm to 0.5% (e.g., 10 ppm to 0.2%) | 100 ppm to 0.1% |
| CO | 0.1 ppm to 5% (e.g., 1 ppm to 2%) | 10 ppm to 1% | 100 ppm to 0.5% |
| $CO_2$ | 0% to 1% (e.g., 0.1 ppm to 1%) | 1 ppm to 0.5% (e.g., 10 ppm to 0.2%) | 100 ppm to 0.1% |
| $CH_4$ | 0% to 1% (e.g., 0.1 ppm to 1%) | 1 ppm to 0.5% (e.g., 10 ppm to 0.2%) | 100 ppm to 0.1% |
| $N_2$ | 0% to 1% (e.g., 0.1 ppm to 1%) | 1 ppm to 0.5% (e.g., 10 ppm to 0.2%) | 100 ppm to 0.1% |
| AD | 0% to 1% (e.g., 0.1 ppm to 1%) | 1 ppm to 0.5% (e.g., 10 ppm to 0.2%) | 100 ppm to 0.1% |
| MeOH | 0% to 1% (e.g., 0.1 ppm to 1%) | 1 ppm to 0.5% (e.g., 10 ppm to 0.2%) | 10 ppm to 0.25% (e.g., 50 ppm to 0.2%), e.g., 100 ppm to 0.1% |
| MeI | 1% to 20% (e.g., 2% to 17%) | 4% to 15% | 5% to 13% |
| MA | 0.5% to 7% (e.g., 1% to 4%) | 1.5% to 5% (e.g., 1.5% to 3%) | 1.7% to 4% (e.g., 1.8% to 2.5%) |
| $H_2O$ | 0.1% to 12% (e.g., 0.5% to 5%) | 0.8% to 3% | 1% to 2.5% |
| AcOH | 30% to 95% (e.g., 40% to 90%) | 50% to 85% | 60% to 80% |
| HI | 0% to 1% (e.g., 0.001% to 1%), e.g., 0.002% to 0.8% (e.g., 0.01% to 0.7%) | 0.003% to 0.5% (e.g., 0.02% to 0.5%) | 0.005% to 0.3% (e.g., 0.05% to 0.3%), e.g., 0.05% to 0.2% |

TABLE 6-continued

| Average molecular weight: 65.23 | Range | Preferred range | More preferred range |
|---|---|---|---|
| FrOH | 0% to 1% (e.g., 1 ppm to 0.1%) | 5 to 500 ppm | 10 to 200 ppm |
| PrOH | 0% to 1% (e.g., 1 ppm to 0.2%) | 5 ppm to 0.1% (e.g., 10 to 500 ppm) | 30 to 300 ppm |
| DME | 0% to 1% (e.g., 0.1 ppm to 0.5%) | 1 ppm to 0.3% (e.g., 5 ppm to 0.1%) | 10 to 500 ppm (e.g., 10 to 300 ppm), e.g., 10 to 100 ppm |
| $(CH_3)_2C=O$ | 0% to 1% (e.g., 1 ppm to 0.1%) | 10 to 300 ppm | 20 to 100 ppm |
| EtOH | 0% to 1% (e.g., 1 ppm to 0.1%) | 10 to 300 ppm | 20 to 100 ppm |
| EA | 0% to 1% (e.g., 1 ppm to 0.1%) | 10 to 300 ppm | 20 to 100 ppm |
| EtI | 0% to 1% (e.g., 1 ppm to 0.1%) | 10 to 300 ppm | 20 to 100 ppm |
| LiI | 0.1% to 25% (e.g., 1% to 20%) | 5% to 23% (e.g., 5% to 17%) | 7% to 20% (e.g., 8% to 15%) |
| Rh | 100 ppm to 0.5% | 200 ppm to 0.2% | 500 to 1500 ppm |
| Fe | 0% to 1% (e.g., 10 ppm to 1%) | 100 ppm to 0.7% | 500 ppm to 0.5% |
| Ni | 0% to 1% (e.g., 1 ppm to 0.5%) | 10 ppm to 0.2% | 100 ppm to 0.1% |
| Cr | 0% to 1% (e.g., 1 ppm to 0.5%) | 10 ppm to 0.2% | 100 ppm to 0.1% |
| Mo | 0% to 1% (e.g., 1 ppm to 0.5%) | 10 ppm to 0.2% | 50 ppm to 0.05% |
| Zn | 0% to 1% (e.g., 10 ppm to 1%) | 100 ppm to 0.7% | 500 ppm to 0.5% |
| Cu | 0% to 1% (e.g., 0.01 ppm to 0.1%) | 0.1 to 100 ppm | 1 to 30 ppm |

Evaporation Step (2)

In the evaporation step (2), the reaction mixture is separated into the volatile phase (2A) and the less-volatile phase (2B) as described above, and the less-volatile phase or catalyst liquid (2B) is recycled via the recycle line 21 to the reactor (1) in the reaction step (1).

The less-volatile phase (2B) (line 21) may have a composition typically as follows.

TABLE 7

| Average molecular weight: 63.47 | Range | Preferred range | More preferred range |
|---|---|---|---|
| Metal catalyst | 200 ppm to 0.5% | 500 ppm to 0.4% | 0.1% to 0.3% |
| Ionic iodide | 1% to 60% (e.g., 2% to 50%) | 3% to 40% (e.g., 5% to 35%) | 5% to 25% (e.g., 8% to 20%) |
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 0.1% (e.g., 1 ppt to 100 ppm) | 30 ppt to 2 ppm | 50 ppt to 1 ppm |
| CO | 0% to 1% (e.g., 5000 ppt to 30 ppm) | 300 ppb to 20 ppm (e.g., 1000 ppb to 10 ppm) | 500 ppb to 5 ppm (e.g., 200 ppb to 1 ppm) |
| $CO_2$ | 0% to 0.1% (e.g., 1 ppt to 100 ppm) | 30 ppt to 2 ppm | 50 ppt to 1 ppm |
| $CH_4$ | 0% to 0.1% (e.g., 1 ppt to 100 ppm) | 30 ppt to 2 ppm | 50 ppt to 1 ppm |
| $N_2$ | 0% to 0.1% (e.g., 1 ppt to 100 ppm) | 30 ppt to 2 ppm | 50 ppt to 1 ppm |
| AD | 0 to 1500 ppm (e.g., 10 ppm to 0.1%) | 5 to 700 ppm (e.g., 30 to 500 ppm) | 10 to 400 ppm (e.g., 20 to 200 ppm), e.g., 50 to 300 ppm |
| MeOH | 0% to 1% (e.g., 0% to 0.8%) | 0% to 0.3% | 0% to 0.2% |
| MeI | 0.01% to 8% (e.g., 0.05% to 6%) | 0.1% to 4% (e.g., 0.5% to 2.5%) | 0.3% to 2.5% (e.g., 0.5% to 2%) |
| MA | 0.6% to 20% (e.g., 0.7% to 15%) | 0.7% to 10% (e.g., 0.8% to 5%) | 0.9% to 3% (e.g., 0.9% to 2%) |
| $H_2O$ | 0.1% to 12% (e.g., 0.5% to 10%) | 0.7% to 8% (e.g., 0.8% to 5%) | 0.8% to 3% (e.g., 0.8% to 2%) |

TABLE 7-continued

| Average molecular weight: 63.47 | Range | Preferred range | More preferred range |
|---|---|---|---|
| AcOH | 35% to 95% (e.g., 45% to 90%) | 60% to 90% | 50% to 85% |
| HI | 0.001% to 1% (e.g., 0.01% to 0.7%) | 0.003% to 0.6% (e.g., 0.02% to 0.5%) | 0.005% to 0.4% (e.g., 0.05% to 0.3%) |
| FrOH | 0% to 0.1% (e.g., 1 ppm to 0.1%) | 5 to 500 ppm | 10 to 200 ppm |
| PrOH | 0% to 0.2% (e.g., 1 ppm to 0.2%) | 5 ppm to 0.1% (e.g., 10 to 500 ppm) | 30 to 300 ppm |
| DME | 0% to 0.5% (e.g., 0.1 ppm to 0.1%) | 1 to 500 ppm (e.g., 3 to 200 ppm) | 5 to 500 ppm (e.g., 10 to 300 ppm), e.g., 5 to 100 ppm |
| $(CH_3)_2C{=}O$ | 0% to 0.1% (e.g., 0.01 ppm to 0.1%) | 0.1 to 100 ppm | 1 to 50 ppm |
| EtOH | 0% to 0.1% (e.g., 0.01 ppm to 0.1%) | 0.1 to 100 ppm | 1 to 50 ppm |
| EA | 0% to 0.1% (e.g., 0.01 ppm to 0.1%) | 0.1 to 100 ppm | 1 to 50 ppm |
| EtI | 0% to 0.1% (e.g., 0.01 ppm to 0.1%) | 0.1 to 100 ppm | 1 to 50 ppm |
| LiI | 0.1% to 33% (e.g., 1% to 26%) | 5% to 30% (e.g., 6% to 21%) | 8% to 27% (e.g., 8% to 24%), e.g., 9% to 19% |
| Rh | 150 to 7000 ppm | 300 to 2500 ppm | 600 to 1800 ppm |
| Fe | 0% to 1% (e.g., 10 ppm to 1%) | 100 ppm to 0.7% | 500 ppm to 0.5% |
| Ni | 0% to 0.5% (e.g., 1 ppm to 0.5%) | 10 ppm to 0.2% | 100 ppm to 0.1% |
| Cr | 0% to 0.5% (e.g., 1 ppm to 0.5%) | 10 ppm to 0.2% | 100 ppm to 0.1% |
| Mo | 0% to 0.5% (e.g., 1 ppm to 0.5%) | 10 ppm to 0.2% | 50 ppm to 0.05% |
| Zn | 0% to 1% (e.g., 10 ppm to 1%) | 100 ppm to 0.7% | 500 ppm to 0.5% |
| Cu | 0% to 0.1% (e.g., 0.01 ppm to 0.1%) | 0.1 to 100 ppm | 1 to 30 ppm |

The less-volatile phase (2B) also contains metals resulting from corrosion, such as iron, nickel, chromium, molybdenum, cobalt, zirconium, zinc, and copper. The contents of these corrosion-derived metals may each be about 2000 ppm by mass or less (e.g., about 1 to about 1000 ppm by mass).

The less-volatile phase (2B) in the recycle line 21 is mixed with a portion 54 of the condensate of the second overhead 51 from the distillation column (dehydration column) (5) in the second distillation step (5) and is then recycled to the reactor (1) in the reaction step (1), where the portion 54 is a portion of the condensate rich in acetic acid.

The condensate 54 may have a composition typically as follows.

TABLE 8

| Average molecular weight: 56.08 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.1 ppt to 1%) | 0.1 ppb to 0.1% (e.g., 1 ppb to 100 ppm) | 1 to 10 ppm |
| CO | 0% to 1% (e.g., 0.1 ppm to 1%) | 1 ppm to 0.5% (e.g., 2 ppm to 0.1%) | 10 to 100 ppm |
| $CO_2$ | 0% to 1% (e.g., 0.1 ppt to 1%) | 0.1 ppb to 0.1% (e.g., 1 ppb to 100 ppm) | 1 to 10 ppm |
| $CH_4$ | 0% to 1% (e.g., 0.1 ppt to 1%) | 0.1 ppb to 0.1% (e.g., 1 ppb to 100 ppm) | 1 to 10 ppm |
| $N_2$ | 0% to 1% (e.g., 0.1 ppt to 1%) | 1 ppm to 0.5% (e.g., 2 ppm to 0.1%) | 10 to 100 ppm |
| AD | 10 ppm to 0.5% | 50 ppm to 0.2% | 100 ppm to 0.1% |
| MeOH | 0% to 2% (e.g., 10 ppm to 2%) | 50 ppm to 1% | 100 ppm to 0.5% |
| MeI | 1% to 30% | 2% to 20% | 5% to 15% |
| MA | 1% to 20% | 2% to 15% | 3% to 12% |
| $H_2O$ | 1% to 20% | 2% to 15% | 3% to 10% |

TABLE 8-continued

| Average molecular weight: 56.08 | Range | Preferred range | More preferred range |
|---|---|---|---|
| AcOH | 30% to 95% | 50% to 90% | 60% to 85% |
| FrOH | 0% to 1% (e.g., 0.1 ppm to 1%) | 10 ppm to 0.1% | 30 to 500 ppm |
| PrOH | 0% to 1% (e.g., 0.1 ppm to 0.1%) | 1 to 100 ppm | 5 to 50 ppm |
| DME | 0% to 2% (e.g., 0.1 ppm to 2%) | 1 ppm to 1% | 10 ppm to 0.2% |
| $(CH_3)_2C=O$ | 0% to 1% (e.g., 0.1 ppm to 1%) | 1 ppm to 0.5% | 10 ppm to 0.1% |
| EtOH | 0% to 1% (e.g., 0.1 ppm to 1%) | 1 ppm to 0.5% | 10 ppm to 0.1% |
| EA | 0% to 1% (e.g., 0.1 ppm to 1%) | 1 ppm to 0.5% | 10 ppm to 0.1% |
| EtI | 0% to 1% (e.g., 0.1 ppm to 1%) | 1 ppm to 0.5% | 10 ppm to 0.1% |
| LiI | 0% to 0.1% (e.g., 0.001 ppb to 10 ppm) | 0.01 ppb to 1 ppm | 0.1 ppb to 0.1 ppm |
| Rh | 0% to 0.1% (e.g., 0.001 ppb to 10 ppm) | 0.01 ppb to 1 ppm | 0.1 ppb to 0.1 ppm |
| Fe | 0% to 0.1% (e.g., 10 ppt to 10 ppm) | 100 ppt to 5 ppm | 1000 ppt to 1 ppm |
| Ni | 0% to 0.1% (e.g., 1 ppt to 1 ppm) | 10 ppt to 0.1 ppm | 100 ppt to 0.05 ppm |
| Cr | 0% to 0.1% (e.g., 1 ppt to 1 ppm) | 10 ppt to 0.1 ppm | 100 ppt to 0.01 ppm |
| Mo | 0% to 0.1% (e.g., 1 ppt to 1 ppm) | 10 ppt to 0.1 ppm | 100 ppt to 0.01 ppm |
| Zn | 0% to 0.1% (e.g., 1 ppt to 1 ppm) | 10 ppt to 0.1 ppm | 100 ppt to 0.01 ppm |
| Cu | 0% to 0.1% (e.g., 1 ppt to 1 ppm) | 10 ppt to 0.1 ppm | 100 ppt to 0.01 ppm |

The concentrations of iron (Fe), nickel (Ni), chromium (Cr), molybdenum (Mo), zinc (Zn), and copper (Cu) in all concentrates in the process streams may fall within the ranges given in the table, unless otherwise specified.

At least a portion of the volatile phase (2A) from the evaporator (2) is fed via a feed line 23 to a distillation column (splitter column) (3) in the lower-boiling component-removing step (3). A portion 24 of the volatile phase from the evaporator (2) is cooled and condensed sequentially in first and second condensers and is separated respectively into condensates 26 and 28, and non-condensable gases (offgases) 25 and 30. The condensates 26 and 28 are recycled via a hold tank T1 and the recycle line 27 to the reactor (1) to cool the reaction mixture in the reactor (1).

A gaseous phase 29 from the hold tank T1 is cooled in the second condenser, and the non-condensable gas (offgas) 30 from the second condenser is fed to a low-pressure absorber (17) in the offgas treatment section (15). A non-condensable gas 192 from the offgas treatment section (15) is also fed to a region between the first condenser and the second condenser and is cooled and condensed in the second condenser, as described later. A condensate (condensate rich in methyl iodide) 193 from the offgas treatment section (15) is also fed to the hold tank T1.

A portion 172 of an overhead stream 171 from the high-pressure absorber (16) in the offgas treatment section (15) is introduced into the evaporator (2), as described blow.

The flash evaporation may be performed as isothermal flash in which the reaction mixture is decompressed by heating, or adiabatic flash in which the reaction mixture is decompressed without heating, or a combination of these flash conditions. By such a flash evaporation, the reaction mixture may be separated into a vapor component (volatile phase) and a liquid component (less-volatile phase). The flash evaporation may be performed at a temperature of typically about 100° C. to about 250° C. (e.g., about 120° C. to about 230° C.), preferably about 150° C. to about 220° C. (e.g., about 160° C. to about 210° C.), and more preferably about 170° C. to about 200° C. The flash evaporation may also be performed at a pressure (absolute pressure) of about 0.03 to about 1 MPa (e.g., about 0.05 to about 1 MPa), preferably about 0.07 to about 0.7 MPa, and more preferably about 0.1 to about 0.5 MPa (e.g., about 0.15 to about 0.4 MPa). The less-volatile phase (2B) may have a temperature of typically about 80° C. to about 200° C. (e.g., about 90° C. to about 180° C.), preferably about 100° C. to about 170° C. (e.g., about 120° C. to about 160° C.), and more preferably about 130° C. to about 160° C. Under such relatively high-temperature (and high pressure) conditions, hydrogen iodide is liable to be formed, and, at some oxygen concentrations, iodine is liable to be formed. According to the present invention, the iodine formation can be effectively restrained even when hydrogen iodide is formed.

The volatile phase (2A) (lines 23 and 24) may have a composition typically as follows.

TABLE 9

| Average molecular weight: 70.17 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |

TABLE 9-continued

| Average molecular weight: 70.17 | Range | Preferred range | More preferred range |
|---|---|---|---|
| $H_2$ | 0% to 1% (e.g., 0.1 ppm to 1%) | 1 ppm to 0.1% | 10 ppm to 0.01% |
| CO | 100 ppm to 3% | 0.1% to 2% | 0.2% to 1% |
| $CO_2$ | 10 ppm to 2% | 100 ppm to 1% (e.g., 0.1% to 0.5%) | 0.02% to 0.5% |
| $CH_4$ | 0% to 1% (e.g., 1 ppm to 1%) | 10 ppm to 0.5% | 100 ppm to 0.1% |
| $N_2$ | 0% to 1% (e.g., 1 ppm to 1%) | 10 ppm to 0.5% | 100 ppm to 0.1% |
| AD | 0% to 1% (e.g., 0.01% to 0.5%) | 0.02% to 0.2% (e.g., 0.03% to 0.15%) | 0.04% to 0.1% |
| MeOH | 0% to 2% (e.g., 10 ppm to 2%) | 50 ppm to 1.5% (e.g., 100 ppm to 1%) | 500 ppm to 0.7% (e.g., 0.1% to 0.5%) |
| MeI | 10% to 60% | 15% to 50% | 20% to 45% |
| MA | 1% to 15% (e.g., 2% to 12%) | 4% to 10% | 5% to 8% |
| $H_2O$ | 0.1% to 10% | 0.8% to 8% | 1.5% to 4% |
| AcOH | 20% to 80% (e.g., 30% to 75%) | 40% to 70% (e.g., 50% to 65%) | 60% to 70% |
| HI | 0% to 1% (e.g., 0.1 ppm to 1%) | 1 ppm to 0.5% (e.g., 5 ppm to 0.3%) | 10 ppm to 0.1% |
| LiI | 0% to 1% (e.g., 0.1 ppm to 1%) | 1 ppm to 0.5% (e.g., 10 ppm to 0.1%) | 30 ppm to 0.03% |
| FrOH | 0% to 1% (e.g., 0.1 ppm to 0.1%) | 1 to 100 ppm | 5 to 50 ppm |
| PrOH | 0% to 1% (e.g., 0.1 ppm to 0.1%) | 1 to 300 ppm (e.g., 5 to 200 ppm) | 10 to 100 ppm |
| DME | 0% to 1% (e.g., 0.1 ppm to 0.1%) | 1 to 700 ppm (e.g., 1 to 100 ppm) | 5 to 500 ppm (e.g., 5 to 50 ppm) |
| $(CH_3)_2C=O$ | 0% to 1% (e.g., 1 ppm to 0.1%) | 10 to 500 ppm | 20 to 100 ppm |
| EtOH | 0% to 1% (e.g., 1 ppm to 0.1%) | 10 to 500 ppm | 20 to 100 ppm |
| EA | 0% to 1% (e.g., 1 ppm to 0.1%) | 10 to 500 ppm | 20 to 100 ppm |
| EtI | 0% to 1% (e.g., 1 ppm to 0.1%) | 10 to 500 ppm | 20 to 100 ppm |
| LiI | 0% to 0.5% (e.g., 1 ppb to 0.1%) | 0.01 to 500 ppm | 0.1 to 200 ppm |
| Rh | 0% to 0.5% (e.g., 1 ppb to 0.1%) | 0.01 to 500 ppm | 0.1 to 100 ppm |
| Fe | 0% to 1% (e.g., 0.1 ppm to 0.2%) | 1 ppm to 0.1% | 10 to 500 ppm |
| Ni | 0% to 0.5% (e.g., 0.1 ppm to 0.1%) | 1 to 500 ppm | 10 to 200 ppm |
| Cr | 0% to 0.5% (e.g., 0.1 ppm to 0.1%) | 1 to 500 ppm | 10 to 200 ppm |
| Mo | 0% to 0.5% (e.g., 0.01 to 500 ppm) | 0.1 to 200 ppm | 1 to 100 ppm |
| Zn | 0% to 1% (e.g., 0.1 ppm to 0.2%) | 1 ppm to 0.1% | 10 to 500 ppm |
| Cu | 0% to 0.1% (e.g., 0.001 to 100 ppm) | 0.01 to 50 ppm | 0.1 to 10 ppm |

The condensate 26 from the first condenser may have a composition typically as follows.

The condensate (recycle line) 27 recycled from the hold tank T1 to the reactor (1) may have a composition approximately identical to or similar to the composition of the condensate 26 from the first condenser. A component proportion of the condensate 27 may be determined by weighted-averaging the corresponding component proportion of the condensate 26 from the first condenser and the component proportion of the condensate 28 from the second condenser.

TABLE 10

| Average molecular weight: 70.60 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.01 ppm to 1%) | 0.1 ppm to 0.1% | 1 ppm to 0.01% |
| CO | 0% to 1% (e.g., 1 ppm to 1%) | 10 ppm to 0.5% | 100 ppm to 0.1% |
| $CO_2$ | 0% to 1% (e.g., 1 ppm to 1%) | 10 ppm to 0.5% | 100 ppm to 0.1% |
| $CH_4$ | 0% to 1% (e.g., 1 ppm to 1%) | 10 ppm to 0.5% | 100 ppm to 0.1% |
| $N_2$ | 0% to 1% (e.g., 1 ppm to 1%) | 10 ppm to 0.5% | 100 ppm to 0.1% |

TABLE 10-continued

| Average molecular weight: 70.60 | Range | Preferred range | More preferred range |
|---|---|---|---|
| AD | 0% to 1% (e.g., 1 ppm to 1%) | 10 ppm to 0.5% | 100 ppm to 0.1% |
| MeOH | 0% to 1% (e.g., 1 ppm to 1%) | 10 ppm to 0.5% | 100 ppm to 0.1% |
| MeI | 1% to 95% | 5% to 90% | 10% to 70% |
| MA | 0.1% to 40% | 0.5% to 20% | 1% to 10% |
| $H_2O$ | 0.1% to 40% | 0.5% to 20% | 1% to 7% |
| AcOH | 1% to 95% | 10% to 90% | 30% to 80% |
| HI | 0% to 0.5% (e.g., 0.01 ppm to 0.1%) | 0.1 ppm to 0.01% | 1 ppm to 0.001% |
| LiI | 0% to 0.5% (e.g., 0.01 ppm to 0.1%) | 0.1 ppm to 0.05% | 1 ppm to 0.01% |
| FrOH | 0% to 0.5% (e.g., 0.01 ppm to 0.1%) | 0.1 ppm to 0.05% | 1 ppm to 0.01% |
| PrOH | 0% to 1% (e.g., 0.1 ppm to 1%) | 1 ppm to 0.1% | 2 ppm to 0.01% |
| DME | 0% to 1% (e.g., 0.01 ppm to 1%) | 0.1 ppm to 0.1% | 1 ppm to 0.01% |
| $(CH_3)_2C=O$ | 0% to 1% (e.g., 0.1 ppm to 1%) | 1 ppm to 0.1% | 5 ppm to 0.05% |
| EtOH | 0% to 1% (e.g., 0.1 ppm to 1%) | 1 ppm to 0.1% | 5 ppm to 0.05% |
| EA | 0% to 1% (e.g., 0.1 ppm to 1%) | 1 ppm to 0.1% | 5 ppm to 0.05% |
| EtI | 0% to 1% (e.g., 0.1 ppm to 1%) | 1 ppm to 0.1% | 5 ppm to 0.05% |
| LiI | 0% to 0.1% (e.g., 0.1 ppt to 10 ppm) | 1 ppt to 1 ppm | 10 ppt to 0.1 ppm |
| Rh | 0% to 0.1% (e.g., 0.1 ppt to 10 ppm) | 1 ppt to 1 ppm | 10 ppt to 0.1 ppm |
| Fe | 0% to 0.5% (e.g., 0.1 ppm to 0.2%) | 1 ppm to 0.1% | 10 to 500 ppm |
| Ni | 0% to 0.2% (e.g., 0.1 ppm to 0.1%) | 1 to 500 ppm | 10 to 200 ppm |
| Cr | 0% to 0.2% (e.g., 0.1 ppm to 0.1%) | 1 to 500 ppm | 10 to 200 ppm |
| Mo | 0% to 0.1% (e.g., 0.01 to 500 ppm) | 0.1 to 200 ppm | 1 to 100 ppm |
| Zn | 0% to 0.5% (e.g., 0.1 ppm to 0.2%) | 1 ppm to 0.1% | 10 to 500 ppm |
| Cu | 0% to 0.1% (e.g., 0.001 to 100 ppm) | 0.01 to 50 ppm | 0.1 to 10 ppm |

The non-condensable gas (offgas) 25 from the first condenser may have a composition typically as follows.

TABLE 11

| Average molecular weight: 46.42 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.1% to 10% | 0.2% to 5% | 0.5% to 5% |
| CO | 1% to 99% | 5% to 90% | 10% to 80% |
| $CO_2$ | 0.1% to 20% | 0.2% to 15% | 0.5% to 8% |
| $CH_4$ | 0.1% to 20% | 0.2% to 15% | 0.5% to 8% |
| $N_2$ | 0.1% to 20% | 0.2% to 15% | 0.5% to 8% |
| AD | 0.001% to 3% | 0.01% to 1% | 0.02% to 0.5% |
| MeOH | 0% to 1% (e.g., 1 ppm to 1%) | 5 ppm to 0.5% | 10 ppm to 0.1% |
| MeI | 1% to 95% | 10% to 90% | 20% to 80% |
| MA | 0.1% to 20% | 0.5% to 10% | 1% to 5% |
| $H_2O$ | 0.01% to 2% | 0.05% to 1% | 0.1% to 0.5% |
| AcOH | 0.1% to 20% | 0.5% to 10% | 1% to 5% |
| FrOH | 0% to 1% (e.g., 0.1 ppm to 0.5%) | 1 ppm to 0.2% | 10 ppm to 0.1% |
| PrOH | 0% to 1% (e.g., 0.1 ppm to 0.5%) | 1 ppm to 0.2% | 10 ppm to 0.1% |
| DME | 0% to 1% (e.g., 0.1 ppm to 1%) | 1 ppm to 0.1% | 5 ppm to 0.05% |
| $(CH_3)_2C=O$ | 0% to 1% (e.g., 0.1 ppm to 1%) | 1 ppm to 0.1% | 5 ppm to 0.05% |
| EtOH | 0% to 1% (e.g., 0.1 ppm to 1%) | 1 ppm to 0.1% | 5 ppm to 0.05% |
| EA | 0% to 1% (e.g., 0.1 ppm to 1%) | 1 ppm to 0.1% | 5 ppm to 0.05% |
| EtI | 0% to 1% (e.g., 0.1 ppm to 1%) | 1 ppm to 0.1% | 5 ppm to 0.05% |
| LiI | 0% to 0.1% (e.g., 0.1 ppt to 100 ppm) | 1 ppt to 10 ppm | 10 ppt to 1 ppm |

TABLE 11-continued

| Average molecular weight: 46.42 | Range | Preferred range | More preferred range |
|---|---|---|---|
| Rh | 0% to 0.1% (e.g., 0.1 ppt to 100 ppm) | 1 ppt to 10 ppm | 10 ppt to 1 ppm |
| Fe | 0% to 0.1% (e.g., 0.1 ppt to 100 ppm) | 1 ppt to 10 ppm | 10 ppt to 1 ppm |
| Ni | 0% to 0.1% (e.g., 0.1 ppt to 100 ppm) | 1 ppt to 10 ppm | 10 ppt to 1 ppm |
| Cr | 0% to 0.1% (e.g., 0.1 ppt to 100 ppm) | 1 ppt to 10 ppm | 10 ppt to 1 ppm |
| Mo | 0% to 0.1% (e.g., 0.1 ppt to 100 ppm) | 1 ppt to 10 ppm | 10 ppt to 1 ppm |
| Zn | 0% to 0.1% (e.g., 0.1 ppt to 100 ppm) | 1 ppt to 10 ppm | 10 ppt to 1 ppm |
| Cu | 0% to 0.1% (e.g., 0.1 ppt to 100 ppm) | 1 ppt to 10 ppm | 10 ppt to 1 ppm |

The condensate 28 from the second condenser may have a composition typically as follows.

TABLE 12

| Average molecular weight: 111.15 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 2% (e.g., 0.01 ppm to 1%) | 0.1 ppm to 0.1% | 1 ppm to 0.01% |
| CO | 0% to 2% (e.g., 1 ppm to 1%) | 10 ppm to 0.5% | 100 ppm to 0.1% |
| $CO_2$ | 0% to 2% (e.g., 1 ppm to 1%) | 10 ppm to 0.5% | 100 ppm to 0.1% |
| $CH_4$ | 0% to 1% (e.g., 0.1 ppm to 0.1%) | 1 ppm to 0.05% | 10 ppm to 0.01% |
| $N_2$ | 0% to 1% (e.g., 0.1 ppm to 0.1%) | 1 ppm to 0.05% | 10 ppm to 0.01% |
| AD | 0% to 1% (e.g., 0.1 ppm to 0.1%) | 1 ppm to 0.05% | 10 ppm to 0.01% |
| MeOH | 0% to 1% (e.g., 0.1 ppm to 0.1%) | 1 ppm to 0.05% | 10 ppm to 0.01% |
| MeI | 1% to 95% (e.g., 5% to 90%) | 10% to 85% (e.g., 50% to 85%) | 70% to 83% |
| MA | 0.1% to 40% | 0.5% to 20% | 1% to 10% |
| $H_2O$ | 0.1% to 40% (e.g., 0.3% to 20%) | 0.5% to 20% (e.g., 1% to 7%) | 0.7% to 5% |
| AcOH | 1% to 95% (e.g., 10% to 90%) | 5% to 30% | 7% to 15% |
| FrOH | 0% to 1% (e.g., 0.01 ppm to 0.1%) | 0.1 ppm to 0.01% | 1 ppm to 0.001% |
| PrOH | 0% to 1% (e.g., 0.01 ppm to 0.1%) | 0.1 ppm to 0.05% | 1 ppm to 0.01% |
| DME | 0% to 1% (e.g., 0.01 ppm to 0.1%) | 0.1 ppm to 0.05% | 1 ppm to 0.01% |
| $(CH_3)_2C{=}O$ | 0% to 1% (e.g., 0.1 ppm to 0.1%) | 1 ppm to 0.05% | 5 ppm to 0.05% |
| EtOH | 0% to 1% (e.g., 0.1 ppm to 0.1%) | 1 ppm to 0.05% | 5 ppm to 0.05% |
| EA | 0% to 1% (e.g., 0.1 ppm to 0.1%) | 1 ppm to 0.05% | 5 ppm to 0.05% |
| EtI | 0% to 1% (e.g., 0.1 ppm to 0.1%) | 1 ppm to 0.05% | 5 ppm to 0.05% |
| LiI | 0% to 0.1% (e.g., 0.1 ppt to 10 ppm) | 1 ppt to 1 ppm | 10 ppt to 0.1 ppm |
| Rh | 0% to 0.1% (e.g., 0.1 ppt to 10 ppm) | 1 ppt to 1 ppm | 10 ppt to 0.1 ppm |

The non-condensable gas 30 from the second condenser may have a composition typically as follows.

TABLE 13

| Average molecular weight: 41.38 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.01% to 5% | 0.05% to 2% | 0.1% to 1% |
| CO | 1% to 99% | 5% to 80% | 10% to 70% |
| $CO_2$ | 0.1% to 20% | 0.5% to 15% | 1% to 10% |
| $CH_4$ | 0.1% to 20% | 0.5% to 15% | 1% to 10% |
| $N_2$ | 0.1% to 20% | 0.5% to 15% | 1% to 10% |
| AD | 0.001% to 3% | 0.01% to 1% | 0.1% to 0.5% |
| MeOH | 0% to 1% (e.g., 1 ppm to 1%) | 5 ppm to 0.5% | 10 ppm to 0.1% |
| MeI | 1% to 95% | 10% to 90% | 20% to 80% |
| MA | 0.01% to 20% | 0.1% to 10% | 0.5% to 5% |
| $H_2O$ | 0.01% to 10% | 0.02% to 1% | 0.05% to 0.5% |
| AcOH | 0.001% to 10% | 0.01% to 1% | 0.05% to 0.5% |
| FrOH | 0% to 1% (e.g., 0.1 ppm to 0.5%) | 1 ppm to 0.2% | 10 ppm to 0.1% |
| PrOH | 0% to 1% (e.g., 0.1 ppm to 0.5%) | 1 ppm to 0.2% | 10 ppm to 0.1% |
| DME | 0% to 1% (e.g., 0.1 ppm to 1%) | 1 ppm to 0.1% | 5 ppm to 0.05% |
| $(CH_3)_2C=O$ | 0% to 1% (e.g., 0.1 ppm to 1%) | 1 ppm to 0.1% | 5 ppm to 0.05% |
| EtOH | 0% to 1% (e.g., 0.1 ppm to 1%) | 1 ppm to 0.1% | 5 ppm to 0.05% |
| EA | 0% to 1% (e.g., 0.1 ppm to 1%) | 1 ppm to 0.1% | 5 ppm to 0.05% |
| EtI | 0% to 1% (e.g., 0.1 ppm to 1%) | 1 ppm to 0.1% | 5 ppm to 0.05% |
| LiI | 0% to 0.1% (e.g., 0.1 ppt to 10 ppm) | 1 ppt to 1 ppm | 10 ppt to 0.1 ppm |
| Rh | 0% to 0.1% (e.g., 0.1 ppt to 10 ppm) | 1 ppt to 1 ppm | 10 ppt to 0.1 ppm |

The evaporator (2) may include a flasher or flashers. A portion of the volatile phase (2A) may be condensed in a condenser, and the resulting condensate may be recycled to the reaction step (the reactor (1)). Alternatively, the entire volatile phase (2A) may be fed to the splitter column (3) in the lower-boiling component-removing step (3) without recycling a portion of the volatile phase (2A) to the reactor (1).

Where necessary, the catalytic component (metal catalyst component) may be separated from the less-volatile phase (2B) through a step or steps and may be recycled to and reused in the reaction step (1).

In the lower-boiling component-removing step (3) and the splitter column (3), the volatile phase (2A) (line 23) is separated into a first overhead (3A), a crude acetic acid stream or side-cut crude acetic acid stream (3B), and a bottom stream (higher-boiling component) (3C). The first overhead (overhead gas, lower-boiling component) (3A) is withdrawn from the top or an upper part of the column via a line 31. The crude acetic acid stream (3B), which mainly contains acetic acid, is side-cut via a line 4. The bottom stream (3C) is withdrawn from the bottom or a lower part of the column via a bottom line 45.

Although not shown, to the splitter column (3) are recycled: a component 66 of a third overhead (6A) (line 61) from a heavy ends column (6); the portion 172 of the overhead stream 171 from the high-pressure absorber (16) in the offgas treatment section (15); and a bottom acetic acid stream 184 from the low-pressure absorber (17) in the offgas treatment section (15).

The first overhead (3A) contains not only methyl iodide, water, and methyl acetate, but also acetaldehyde and carbon monoxide; and is fed to the separation section (9) for removal of impurities such as acetaldehyde, and to the offgas treatment section (15).

The crude acetic acid stream (3B) (line 42) mainly contains acetic acid and further contains other components such as methyl iodide, methyl acetate, and water. A portion 43 of the crude acetic acid stream 42 may be returned to the splitter column (3). The remainder 44 of the crude acetic acid stream 42 is purified in the purification section (4) for dehydration and removal of higher-boiling components, to yield a high-purity acetic acid product.

The bottom stream (3C) (line 45) generally contains water and acetic acid and may often further contain other components such as propionic acid. A portion of the bottom stream (3C) is returned to a lower part of the splitter column (3). The bottom stream 45, which may contain an entrained metal catalyst component (lithium iodide), is recycled to the evaporator (2).

The first overhead (3A) contains methyl iodide and a permanganate reducing compound or compounds (PRC's) including by-produced acetaldehyde. The first overhead (3A) generally further contains methyl acetate and may often contain other components such as acetic acid, methanol, water, dimethyl ether, and acetaldehyde-derived by-products. Non-limiting examples of the acetaldehyde-derived by-products include aldehydes such as crotonaldehyde and butyraldehyde; acetaldehyde derivatives such as $C_2$-$C_{12}$ alkyl iodides and $C_3$-$C_{12}$ alkanecarboxylic acids; and $C_2$-$C_{12}$ alkanes.

The first overhead (3A) (line 31) may have a composition typically as follows.

TABLE 14

| Average molecular weight: 52.19 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 0.1 ppm to 1%) | 1 ppm to 0.1% | 10 ppm to 0.03% |
| CO | 500 ppm to 10% | 0.1% to 5% | 0.2% to 3% |
| $CO_2$ | 100 ppm to 2% | 500 ppm to 1% | 0.1% to 0.5% |
| $CH_4$ | 0% to 1% (e.g., 1 ppm to 1%) | 10 ppm to 0.5% | 100 ppm to 0.3% |
| $N_2$ | 0% to 1% (e.g., 1 ppm to 1%) | 10 ppm to 0.5% | 100 ppm to 0.3% |
| AD | 0.01% to 1% | 0.05% to 0.5% | 0.1% to 0.3% |
| MeOH | 0% to 4%, e.g., 0% to 2% (e.g., 10 ppm to 2%) | 100 ppm to 1% | 200 ppm to 0.7% (e.g., 0.1% to 0.5%) |
| MeI | 20% to 95% | 30% to 90% | 50% to 80% |
| MA | 1% to 40% | 3% to 30% | 7% to 20% |
| $H_2O$ | 1% to 60% | 5% to 50% | 10% to 30% |
| AcOH | 0.1% to 20% | 1% to 15% | 2% to 10% |
| HI | 0% to 1% (e.g., 0.1 ppm to 1%) | 1 ppm to 0.5% | 5 ppm to 0.3% (e.g., 10 ppm to 0.1%) |
| FrOH | 0% to 1% (e.g., 0.1 ppm to 1%) | 1 ppm to 0.5% | 10 ppm to 0.1% |
| PrOH | 0% to 0.5% (e.g., 0.1 ppm to 0.1%) | 1 to 700 ppm (e.g., 1 to 100 ppm) | 3 to 500 ppm (e.g., 3 to 50 ppm) |
| DME | 0% to 0.5% (e.g., 0.1 ppm to 0.1%) | 0.5 to 700 ppm (e.g., 1 to 300 ppm) | 5 to 500 ppm (e.g., 10 to 100 ppm) |
| $(CH_3)_2C{=}O$ | 0% to 0.5% (e.g., 0.1 ppm to 0.1%) | 1 to 100 ppm | 10 to 70 ppm |
| EtOH | 0% to 0.5% (e.g., 0.1 ppm to 0.1%) | 1 to 100 ppm | 10 to 70 ppm |
| EA | 0% to 0.5% (e.g., 0.1 ppm to 0.1%) | 1 to 100 ppm | 10 to 70 ppm |
| EtI | 0% to 0.5% (e.g., 0.1 ppm to 0.1%) | 1 to 100 ppm | 10 to 70 ppm |
| LiI | 0% to 0.1% (e.g., 0.1 ppt to 10 ppm) | 1 ppt to 1 ppm | 10 ppt to 0.1 ppm |
| Rh | 0% to 0.1% (e.g., 0.1 ppt to 10 ppm) | 1 ppt to 1 ppm | 10 ppt to 0.1 ppm |

The acetic acid stream (3B) (line 42) may have a composition typically as follows.

The crude acetic acid stream 44 to be fed to the purification section may have a composition approximately identical to or similar to the composition of the crude acetic acid stream (3B) (line 42).

TABLE 15

| Average molecular weight: 58.72 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.1 ppm to 1%) | 1 ppm to 0.1% | 10 ppm to 0.03% |
| CO | 0% to 1% (e.g., 10 ppm to 1%) | 50 ppm to 0.5% | 100 ppm to 0.3% |
| $CO_2$ | 0% to 1% (e.g., 0.1 ppm to 0.5%) | 1 ppm to 0.2% | 2 ppm to 0.1% |
| $CH_4$ | 0% to 1% (e.g., 1 ppm to 1%) | 10 ppm to 0.5% | 100 ppm to 0.3% |
| $N_2$ | 0% to 1% (e.g., 1 ppm to 1%) | 10 ppm to 0.5% | 100 ppm to 0.3% |
| AD | 0% to 1% (e.g., 5 ppm to 1%) | 10 ppm to 0.5% | 20 ppm to 0.3% |
| MeOH | 0% to 2% (e.g., 10 ppm to 1.5%) | 20 ppm to 1.2% (e.g., 100 ppm to 1%) | 30 ppm to 0.1% (or 0.1% to 0.5%) |
| MeI | 0.1% to 15% | 0.5% to 10% | 1% to 5% |
| MA | 0.1% to 15% | 0.5% to 10% | 1% to 5% |
| $H_2O$ | 0.1% to 10% | 0.5% to 8% | 1% to 5% |
| AcOH | 10% to 99% (e.g., 30% to 98%) | 50% to 97% | 60% to 95% |
| HI | 0% to 1% (e.g., 0.1 ppm to 1%) | 1 ppm to 0.5% | 10 ppm to 0.1% |

TABLE 15-continued

| Average molecular weight: 58.72 | Range | Preferred range | More preferred range |
|---|---|---|---|
| FrOH | 0% to 1% (e.g., 0.1 ppm to 1%) | 1 ppm to 0.5% | 10 ppm to 0.1% |
| PrOH | 0% to 0.5% (e.g., 0.1 ppm to 0.1%) | 1 to 700 ppm (e.g., 1 to 100 ppm) | 3 to 500 ppm (e.g., 3 to 50 ppm) |
| DME | 0% to 0.5% (e.g., 0.1 ppm to 0.1%) | 0.5 to 700 ppm (e.g., 1 to 300 ppm) | 5 to 500 ppm (e.g., 10 to 100 ppm) |
| $(CH_3)_2C=O$ | 0% to 0.5% (e.g., 0.1 ppm to 0.1%) | 1 to 100 ppm | 10 to 70 ppm |
| EtOH | 0% to 0.5% (e.g., 0.1 ppm to 0.1%) | 1 to 100 ppm | 10 to 70 ppm |
| EA | 0% to 0.5% (e.g., 0.1 ppm to 0.1%) | 1 to 100 ppm | 10 to 70 ppm |
| EtI | 0% to 0.5% (e.g., 0.1 ppm to 0.1%) | 1 to 100 ppm | 10 to 70 ppm |
| Li | 0% to 0.1% (e.g., 100 ppt to 10 ppm) | 0.5 ppb to 50 ppm (e.g., 1 ppb to 1 ppm) | 5 ppb to 10 ppm (e.g., 10 ppb to 0.5 ppm) |
| Rh | 0% to 0.1% (e.g., 10 ppt to 10 ppm) | 0.1 ppb to 1 ppm | 1 to 100 ppb |
| Fe | 0% to 0.1% (e.g., 0.1 ppt to 100 ppm) | 1 ppt to 10 ppm | 10 ppt to 1 ppm |
| Ni | 0% to 0.1% (e.g., 0.1 ppt to 100 ppm) | 1 ppt to 10 ppm | 10 ppt to 1 ppm |
| Cr | 0% to 0.1% (e.g., 0.1 ppt to 100 ppm) | 1 ppt to 10 ppm | 10 ppt to 1 ppm |
| Mo | 0% to 0.1% (e.g., 0.1 ppt to 100 ppm) | 1 ppt to 10 ppm | 10 ppt to 1 ppm |
| Zn | 0% to 0.1% (e.g., 0.1 ppt to 100 ppm) | 1 ppt to 10 ppm | 10 ppt to 1 ppm |
| Cu | 0% to 0.1% (e.g., 0.1 ppt to 100 ppm) | 1 ppt to 10 ppm | 10 ppt to 1 ppm |

The mass ratio of the flow rate of the crude acetic acid stream (3B) to be fed to the purification section (4) to the flow rate of the portion 43 to be recycled to the splitter column (3), the ratio of the former and the latter, may be from about 100:1 to about 2:1 (e.g., from about 25:1 to about 5:1), preferably from about 15:1 to about 7:1 (e.g., from about 10:1 to about 8:1).

The bottom stream (3C) (line 45) may typically have a composition as follows.

TABLE 16

| Average molecular weight: 58.88 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.1 ppm to 1%) | 1 ppm to 0.1% | 10 ppm to 0.01% |
| CO | 0% to 2% (e.g., 1 ppm to 2%) | 10 ppm to 1% | 100 ppm to 0.1% |
| $CO_2$ | 0% to 1% (e.g., 0.1 ppm to 1%) | 1 ppm to 0.1% | 10 ppm to 0.01% |
| $CH_4$ | 0% to 1% (e.g., 0.1 ppm to 1%) | 1 ppm to 0.1% | 10 ppm to 0.01% |
| $N_2$ | 0% to 1% (e.g., 0.1 ppm to 1%) | 1 ppm to 0.1% | 10 ppm to 0.01% |
| AD | 0% to 0.1% (e.g., 0.01 to 500 ppm) | 0.1 to 200 ppm | 1 to 100 ppm |
| MeOH | 0% to 1% (e.g., 0.1 ppm to 1%) | 1 ppm to 0.2% | 10 ppm to 0.1% |
| MeI | 5 ppm to 5% (e.g., 10 ppm to 2%) | 50 ppm to 3% (e.g., 100 ppm to 1%) | 200 ppm to 2% (e.g., 300 ppm to 0.5%) |
| MA | 0.01% to 6% | 0.1% to 4% | 0.5% to 3% |
| $H_2O$ | 0.01% to 10% | 0.1% to 5% | 0.5% to 4% (e.g., 1% to 3%) |
| AcOH | 60% to 99.5% (e.g., 80% to 99%) | 85% to 99% | 90% to 98% |
| HI | 0% to 1% (e.g., 0.01 ppm to 1%) | 0.1 ppm to 0.5% | 1 ppm to 0.1% |
| FrOH | 0% to 1% (e.g., 0.1 ppm to 0.1%) | 1 to 500 ppm | 5 to 100 ppm |
| PrOH | 0.1 ppm to 0.1% | 1 to 500 ppm | 3 to 300 ppm (e.g., 5 to 100 ppm) |
| DME | 0% to 1% (e.g., 0.1 ppm to 0.1%) | 1 to 500 ppm | 3 to 300 ppm (e.g., 5 to 100 ppm) |
| $(CH_3)_2C=O$ | 0% to 1% (e.g., 0.1 ppm to 0.1%) | 1 to 500 ppm | 5 to 100 ppm |
| EtOH | 0% to 1% (e.g., 0.1 ppm to 0.1%) | 1 to 500 ppm | 5 to 100 ppm |

TABLE 16-continued

| Average molecular weight: 58.88 | Range | Preferred range | More preferred range |
|---|---|---|---|
| EA | 0% to 1% (e.g., 0.1 ppm to 0.1%) | 1 to 500 ppm | 5 to 100 ppm |
| EtI | 0% to 1% (e.g., 0.1 ppm to 0.1%) | 1 to 500 ppm | 5 to 100 ppm |
| LiI | 1 ppm to 2% (e.g., 1 ppm to 0.5%) | 3 ppm to 1.5% (e.g., 5 ppm to 0.1%) | 5 ppm to 1% (e.g., 10 to 500 ppm) |
| Rh | 1 ppb to 300 ppm | 10 ppb to 100 ppm | 100 ppb to 50 ppm |
| Fe | 0% to 1% (e.g., 0.1 ppm to 0.5%) | 1 ppm to 0.2% | 10 ppm to 0.1% |
| Ni | 0% to 0.5% (e.g., 0.1 ppm to 0.2%) | 1 ppm to 0.1% | 10 to 400 ppm |
| Cr | 0% to 0.5% (e.g., 0.1 ppm to 0.2%) | 1 ppm to 0.1% | 10 to 400 ppm |
| Mo | 0% to 0.5% (e.g., 0.01 ppm to 0.1%) | 0.1 to 400 ppm | 1 to 200 ppm |
| Zn | 0% to 1% (e.g., 0.1 ppm to 4000 ppm) | 1 ppm to 0.2% | 10 ppm to 0.1% |
| Cu | 0% to 0.1% (e.g., 0.001 to 200 ppm) | 0.01 to 100 ppm | 0.1 to 20 ppm |

The splitter column (3) for use herein may be selected typically from plate columns and packed columns. The liquid stream (3C) may be discharged; or may be partially or entirely returned to the splitter column (3) and/or recycled to the reactor (1).

Purification Section (4)

The crude acetic acid stream (3B) (line 44) contains impurities such as lower-boiling impurities, higher-boiling impurities, and ionic iodine compounds. To separate and remove these impurities for purification, the crude acetic acid stream (3B) is fed to the purification section (4). The purification section (4) may include steps such as (5) a dehydrating step, (6) a higher-boiling component-removing step, (7) a rectifying step, and (8) an ion exchange step. The dehydrating step (second distillation step) (5) is the step of removing mainly water from the crude acetic acid stream. The higher-boiling component-removing step (third distillation step) (6) is the step of removing higher-boiling components from the crude acetic acid stream. The rectifying step (fourth distillation step) (7) is the step of further removing impurities from the crude acetic acid stream by distillation. The ion exchange step (8) is the step of separating iodine compounds from the crude acetic acid stream by ion exchange. The dehydrating step (5), the higher-boiling component-removing step (6), the rectifying step (7), and the ion exchange step (8) may be performed in any sequence. For example, the dehydrating step (5), the higher-boiling component-removing step (6), and the rectifying step (7) may be performed after the ion exchange step (8). Alternatively, the ion exchange step (8) and subsequently the rectifying step (7) may be performed after the dehydrating step (5) and the higher-boiling component-removing step (6). Further alternatively, the ion exchange step (8) may be performed after the dehydrating step (5), the higher-boiling component-removing step (6), and the rectifying step (7). The purification section (4) may often include the dehydrating step (5) among the steps (5) to (8). The purification section (4) does not always have to include the rectifying step (7). The dehydrating step (5), the higher-boiling component-removing step (6), and the rectifying step (7) are performed respectively in a dehydration-distillation column (second distillation column), a higher-boiling distillation column (third distillation column), and a purification-distillation column (rectifying column). When the lower-boiling component-removing step (3) is a lower-boiling component-removing-dehydrating step, the purification section (4) does not have to include the dehydrating step (5).

Dehydration Step (5)

In the dehydrating step (5), the crude acetic acid stream (3B) (line 44) is distilled in the dehydration-distillation column (5) and is separated into a second overhead (5A) and a bottom acetic acid stream (5B). The second overhead (5A), which is rich in water, is withdrawn from the top or an upper part of the column via a line 51. The bottom acetic acid stream (second acetic acid stream) (5B), which is rich in acetic acid, is withdrawn from the bottom or a lower part of the column via a bottom line 56. A portion of the bottom acetic acid stream (5B) is heated in a heating unit and is returned to the dehydration-distillation column (5); whereas the remainder of the bottom acetic acid stream (5B) is fed to the heavy ends column (6).

The second overhead (5A) is cooled in a condenser and introduced into a hold tank T2 to form a condensate 52 and a gaseous phase 55. A portion 53 of the condensate 52 is refluxed to the dehydration-distillation column (5), and another portion of the condensate is sent via a line 54, mixed with the less-volatile phase (2B), and recycled to the reactor (1). The gaseous phase 55 (non-condensable gas (offgas)) from the hold tank T2, which is rich in carbon monoxide, is fed to the offgas treatment section (15).

The second overhead (5A) (line 51) may typically have a composition as follows.

The condensates (condensates from the hold tank T2) 52 and 53 of the second overhead (5A) may have compositions approximately identical to or similar to the composition of the second overhead (5A). A component proportion in the compositions of the condensates 52 and 53 may be determined by subtracting the corresponding component proportion in the gaseous phase (non-condensable gas) 55 fed from the hold tank T2, from the component proportion in the second overhead (5A).

TABLE 17

| Average molecular weight: 56.08 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 0.01 ppm to 0.1%) | 0.1 ppb to 500 ppm (e.g., 0.1 to 500 ppm) | 1 ppb to 100 ppm (e.g., 1 to 100 ppm) |
| CO | 0% to 1% (e.g., 0.1 ppm to 1%) | 0.1 ppb to 0.5% (e.g., 1 ppm to 0.5%) | 10 ppb to 0.1% (e.g., 10 ppm to 0.1%) |
| $CO_2$ | 0% to 1% (e.g., 0.01 ppm to 0.1%) | 0.1 ppb to 500 ppm (e.g., 0.1 to 500 ppm) | 1 ppb to 100 ppm (e.g., 1 to 100 ppm) |
| $CH_4$ | 0% to 1% (e.g., 0.01 ppm to 0.1%) | 0.1 ppb to 500 ppm (e.g., 0.1 to 500 ppm) | 1 ppb to 100 ppm (e.g., 1 to 100 ppm) |
| $N_2$ | 0% to 5%, 0% to 2%, 0% to 1% (e.g., 0.01 ppm to 0.1%) | 0.1 to 500 ppm | 1 to 100 ppm |
| AD | 0.1 ppm to 1%, e.g., 1 ppm to 0.3% | 1 ppm to 0.2%, e.g., 10 ppm to 0.1% | 1 ppm to 0.1%, e.g., 50 to 500 ppm |
| MeOH | 0% to 2% (e.g., 10 ppm to 2%) | 100 ppm to 1% | 200 ppm to 0.5%, e.g., 0.1% to 0.5% |
| MeI | 0.1% to 30% | 1% to 20% | 3% to 15% |
| MA | 0.1% to 20% | 1% to 15% | 2% to 12% |
| $H_2O$ | 0.1% to 20% | 1% to 15% | 2% to 10% |
| AcOH | 10% to 95% (e.g., 30% to 90%) | 50% to 85% | 60% to 85% |
| HI | 0% to 1% (e.g., 0.1 ppm to 1%), e.g., 0.1 ppb to 1% | 10 ppb to 0.5% (e.g., 1 ppm to 0.5%) | 0.1 ppm to 0.1% (e.g., 10 ppm to 0.1%) |
| FrOH | 0% to 1% (e.g., 0.1 ppm to 1%) | 1 ppm to 0.5% | 10 ppm to 0.1% |
| PrOH | 0% to 0.3% (e.g., 0.1 ppm to 0.1%) | 1 to 700 ppm (e.g., 1 to 100 ppm) | 3 to 500 ppm (e.g., 3 to 200 ppm), e.g., 3 to 50 ppm |
| DME | 0% to 1% (e.g., 0.1 ppm to 0.5%) | 1 ppm to 0.1% | 10 to 500 ppm |
| $(CH_3)_2C=O$ | 0% to 0.5% (e.g., 0.01 ppm to 0.1%) | 0.1 to 100 ppm | 1 to 50 ppm |
| EtOH | 0% to 0.5% (e.g., 0.01 ppm to 0.1%) | 0.1 to 100 ppm | 1 to 50 ppm |
| EA | 0% to 0.5% (e.g., 0.01 ppm to 0.1%) | 0.1 to 100 ppm | 1 to 50 ppm |
| EtI | 0% to 0.5% (e.g., 0.01 ppm to 0.1%) | 0.1 to 100 ppm | 1 to 50 ppm |
| Li | 0% to 0.1% (e.g., 0.1 ppt to 10 ppm) | 1 ppt to 1 ppm | 10 ppt to 0.1 ppm |
| Rh | 0% to 0.1% (e.g., 0.1 ppt to 10 ppm) | 1 ppt to 1 ppm | 10 ppt to 0.1 ppm |

The gaseous phase (non-condensable gas) 55 from the hold tank T2 may have a composition typically as follows.

Assume that, for example, an inert gas such as nitrogen gas is introduced to regulate the pressure of the dehydration-distillation column (5), and to eliminate or minimize the deposition of organic substances to measuring instruments, as described above. In this case, the composition of the inert gas (such as nitrogen gas) in the following table is significantly increased.

TABLE 18

| Average molecular weight: 27.90 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 0.01 ppm to 0.1%) | 0.1 to 500 ppm | 1 to 300 ppm |
| CO | 1% to 99.9% | 50% to 99.8% | 70% to 99.6% |
| $CO_2$ | 0% to 1% (e.g., 0.01 ppm to 0.5%) | 0.1 ppm to 0.1% | 1 to 500 ppm |
| $CH_4$ | 1 ppm to 10% | 10 ppm to 3% | 100 ppm to 1% |
| $N_2$ | 1 ppm to 10% | 10 ppm to 3% | 100 ppm to 1% |
| AD | 0% to 1% (e.g., 0.1 ppm to 0.5%) | 1 ppm to 0.1% | 10 to 500 ppm |
| MeOH | 0% to 1% (e.g., 0.1 ppm to 0.5%) | 1 ppm to 0.1% | 10 to 500 ppm |
| MeI | 0% to 1% (e.g., 1 ppm to 1%) | 5 ppm to 0.5% | 10pm to 0.1% |

TABLE 18-continued

| Average molecular weight: 27.90 | Range | Preferred range | More preferred range |
|---|---|---|---|
| MA | 0% to 1% (e.g., 1 ppm to 1%) | 5 ppm to 0.5% | 10pm to 0.1% |
| $H_2O$ | 0% to 1% (e.g., 1 ppm to 1%) | 5 ppm to 0.5% | 10pm to 0.1% |
| AcOH | 0% to 1% (e.g., 1 ppm to 1%) | 5 ppm to 0.5% | 10pm to 0.1% |
| HI | 0% to 0.5% (e.g., 0.01 ppm to 0.1%) | 0.1 ppm to 0.05% | 1 ppm to 0.01% |
| FrOH | 0% to 0.5% (e.g., 0.01 ppm to 0.1%) | 0.1 ppm to 0.05% | 1 ppm to 0.01% |
| PrOH | 0% to 0.5% (e.g., 0.01 ppm to 0.1%) | 0.1 ppm to 0.05% | 1 ppm to 0.01% |
| DME | 0% to 0.5% (e.g., 0.01 ppm to 0.1%) | 0.1 ppm to 0.05% | 1 ppm to 0.01% |
| $(CH_3)_2C{=}O$ | 0% to 0.5% (e.g., 0.01 ppm to 0.1%) | 0.1 to 100 ppm | 1 to 50 ppm |
| EtOH | 0% to 0.5% (e.g., 0.01 ppm to 0.1%) | 0.1 to 100 ppm | 1 to 50 ppm |
| EA | 0% to 0.5% (e.g., 0.01 ppm to 0.1%) | 0.1 to 100 ppm | 1 to 50 ppm |
| EtI | 0% to 0.5% (e.g., 0.01 ppm to 0.1%) | 0.1 to 100 ppm | 1 to 50 ppm |
| Li | 0% to 0.1% (e.g., 0.1 ppt to 10 ppm) | 1 ppt to 1 ppm | 10 ppt to 0.1 ppm |
| Rh | 0% to 0.1% (e.g., 0.1 ppt to 10 ppm) | 1 ppt to 1 ppm | 10 ppt to 0.1 ppm |

The bottom acetic acid stream (5B) (line 56) may have a composition typically as follows.

TABLE 19

| Average molecular weight: 59.99 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 0.1% (e.g., 0.01 to 100 ppm) | 0.1 to 50 ppm | 1 to 10 ppm |
| CO | 0% to 0.1% (e.g., 0.01 to 100 ppm) | 0.1 to 50 ppm | 1 to 10 ppm |
| $CO_2$ | 0% to 0.1% (e.g., 0.01 to 100 ppm) | 0.1 to 50 ppm | 1 to 10 ppm |
| $CH_4$ | 0% to 0.1% (e.g., 0.01 to 100 ppm) | 0.1 to 50 ppm | 1 to 10 ppm |
| $N_2$ | 0% to 0.1% (e.g., 0.01 to 100 ppm) | 0.1 to 50 ppm | 1 to 10 ppm |
| AD | 0% to 0.05% (e.g., 0.001 to 50 ppm) | 0.01 to 20 ppm | 0.1 to 10 ppm |
| MeOH | 0% to 0.1% (e.g., 0.001 to 100 ppm) | 0.01 to 10 ppm | 0.1 to 5 ppm |
| MeI | 0% to 0.01% (e.g., 0.01 to 10 ppb) | 0.05 to 200 ppb (e.g., 0.1 to 5 ppb) | 0.2 to 50 ppb (e.g., 0.2 to 10 ppb), e.g., 0.3 to 2 ppb |
| MA | 0% to 0.1% (e.g., 0.001 ppm to 0.1%) | 0.01 to 100 ppm | 0.1 to 50 ppm |
| $H_2O$ | 0% to 1% (e.g., 1 ppm to 1%) | 10 ppm to 0.5% | 100 ppm to 0.1% |
| AcOH | 98% to 100% | 99% to 99.999% | 99.5% to 99.99% |
| HI | 0% to 0.1% (e.g., 0.01 ppb to 100 ppm) | 0.1 ppb to 10 ppm | 1 ppb to 1 ppm |
| FrOH | 0% to 0.1% (e.g., 0.1 to 500 ppm) | 1 to 100 ppm | 5 to 50 ppm |
| PrOH | 0% to 0.2% (e.g., 5 ppm to 0.2%) | 30 ppm to 0.1% | 70 to 500 ppm (e.g., 100 to 250 ppm) |
| DME | 0% to 0.1% (e.g., 1 ppb to 10 ppm) | 10 ppb to 5 ppm | 50 ppb to 1 ppm |
| $(CH_3)_2C{=}O$ | 0% to 0.1% (e.g., 0.1 ppb to 100 ppm) | 1 ppb to 10 ppm | 10 ppb to 1 ppm |
| EtOH | 0% to 0.1% (e.g., 0.1 ppb to 100 ppm) | 1 ppb to 10 ppm | 10 ppb to 1 ppm |
| EA | 0% to 0.1% (e.g., 0.1 ppb to 100 ppm) | 1 ppb to 10 ppm | 10 ppb to 1 ppm |
| EtI | 0% to 0.1% (e.g., 0.1 ppb to 100 ppm) | 1 ppb to 10 ppm | 10 ppb to 1 ppm |
| Li | 0% to 0.1% (e.g., 1 ppt to 10 ppm) | 10 ppt to 1 ppm | 100 ppt to 0.1 ppm |
| Rh | 0% to 0.1% (e.g., 1 ppt to 10 ppm) | 10 ppt to 1 ppm | 100 ppt to 0.1 ppm |

In the dehydrating step (5), methanol 3 may be added (fed) at a site or sites of the dehydration-distillation column (5), so as to convert hydrogen iodide contained in the crude acetic acid stream 44 into methyl iodide and to be distilled out as the second overhead (5A) (line 51). In addition, the bottom acetic acid stream 56 from the dehydrating step (5) may be mixed with an aqueous potassium hydroxide solution 57 to allow potassium hydroxide to react with hydrogen iodide in the bottom acetic acid stream 56 to thereby remove hydrogen iodide as potassium iodide. A bottom acetic acid stream 58, which has been treated with potassium hydroxide, may be distilled in the higher-boiling component-removing step (6) for separating and removing mainly higher-boiling components.

Alternatively, a methanol source may be added to (fed to) the dehydration-distillation column so as to remove hydrogen iodide, where the methanol source may typically be at least one component selected from the group consisting of methanol, methyl acetate, and dimethyl ether. Potassium hydroxide is used in the above embodiment for the removal of hydrogen iodide. However, any of other alkali metal components may also be used. Non-limiting examples of the alkali metal components include alkali metal hydroxides such as sodium hydroxide; alkali metal carbonates; and alkali metal acetates such as sodium acetate and potassium acetate.

The methanol 3 has a composition approximately identical to or similar to that mentioned above.

The aqueous potassium hydroxide solution 57 may have a composition typically as follows.

TABLE 20

| Average molecular weight: 25.94 | Range | Preferred range | More preferred range |
| --- | --- | --- | --- |
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2O$ | 40% to 99.9% | 50% to 99% | 55% to 90% |
| KOH | 0.1% to 60% | 1% to 50% | 10% to 45% |

The bottom acetic acid stream 58 may have a composition typically as follows.

TABLE 21

| Average molecular weight: 59.98 | Range | Preferred range | More preferred range |
| --- | --- | --- | --- |
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 0.1% (e.g., 0.01 to 100 ppm) | 0.1 to 50 ppm | 1 to 10 ppm |
| CO | 0% to 0.1% (e.g., 0.01 to 100 ppm) | 0.1 to 50 ppm | 1 to 10 ppm |
| $CO_2$ | 0% to 0.1% (e.g., 0.01 to 100 ppm) | 0.1 to 50 ppm | 1 to 10 ppm |
| $CH_4$ | 0% to 0.1% (e.g., 0.01 to 100 ppm) | 0.1 to 50 ppm | 1 to 10 ppm |
| $N_2$ | 0% to 0.1% (e.g., 0.01 to 100 ppm) | 0.1 to 50 ppm | 1 to 10 ppm |
| AD | 0% to 0.1% (e.g., 0.001 to 50 ppm) | 0.01 to 20 ppm | 0.1 to 10 ppm |
| MeOH | 0% to 0.1% (e.g., 0.001 to 100 ppm) | 0.01 to 10 ppm | 0.1 to 5 ppm |
| MeI | 0% to 0.01% (e.g., 0.01 to 10 ppb) | 0.1 to 5 ppb | 0.3 to 2 ppb |
| MA | 0% to 0.1% (e.g., 0.001 ppm to 0.1%) | 0.01 to 100 ppm | 0.1 to 50 ppm |
| $H_2O$ | 0% to 1% (e.g., 1 ppm to 1%) | 10 ppm to 0.5% | 100 ppm to 0.1% |
| AcOH | 98% to 99.999% | 99% to 99.99% | 99.5% to 99.9% |
| HI | 0% to 0.1% (e.g., 0.01 ppb to 100 ppm) | 0.1 ppb to 10 ppm | 1 ppb to 1 ppm |
| FrOH | 0% to 0.1% (e.g., 0.1 to 500 ppm) | 1 to 100 ppm | 5 to 50 ppm |
| PrOH | 0% to 0.2% (e.g., 5 ppm to 0.2%) | 30 ppm to 0.1% (e.g., 70 to 500 ppm) | 100 to 250 ppm |
| KOH | 0% to 0.1% (e.g., 1 ppm to 0.1%) | 5 to 500 ppm | 10 to 100 ppm |
| DME | 0% to 0.1% (e.g., 1 ppb to 10 ppm) | 10 ppb to 5 ppm | 50 ppb to 1 ppm |
| $(CH_3)_2C=O$ | 0% to 0.1% (e.g., 0.01 ppb to 10 ppm) | 0.1 ppb to 1 ppm | 1 ppb to 0.1 ppm |
| EtOH | 0% to 0.1% (e.g., 0.01 ppb to 10 ppm) | 0.1 ppb to 1 ppm | 1 ppb to 0.1 ppm |
| EA | 0% to 0.1% (e.g., 0.01 ppb to 10 ppm) | 0.1 ppb to 1 ppm | 1 ppb to 0.1 ppm |
| EtI | 0% to 0.1% (e.g., 0.01 ppb to 10 ppm) | 0.1 ppb to 1 ppm | 1 ppb to 0.1 ppm |
| Li | 0% to 0.1% (e.g., 1 ppt to 10 ppm) | 10 ppt to 1 ppm | 100 ppt to 0.1 ppm |
| Rh | 0% to 0.1% (e.g., 1 ppt to 10 ppm) | 10 ppt to 1 ppm | 100 ppt to 0.1 ppm |

The dehydrating step (5) may include a single step or may include steps in which the bottom stream (5B) is distilled through a succeeding step or steps. For example, it is acceptable that, while a portion of the bottom stream (5B) is returned to the dehydration-distillation column (5), the remainder of the bottom stream (5B) is fed to a succeeding dehydration-distillation column (5). The dehydration-distillation column(s) (5) for use herein may be selected typically from plate columns and packed columns.

Heavier Components-Removing Step (6)

The bottom acetic acid stream (5B) still contains higher-boiling components such as propionic acid, although it has a significantly improved acetic acid purity by the removal of lower-boiling components. To remove such higher-boiling components, the bottom acetic acid stream (line 56 or line 58) is subjected to the higher-boiling component-removing step (6). Specifically, in the higher-boiling component-removing step (6), the bottom acetic acid stream (5B) is distilled in a heavy ends column (higher-boiling distillation column) (6) to be separated into a third overhead (6A), an acetic acid stream (6B), and a bottom stream (6C). The third overhead (6A) (line 61), which is rich in acetic acid, is withdrawn from the top or an upper part of the column. The acetic acid stream (third acetic acid stream) (6B) (line 67), which is rich in acetic acid, is side-cut at a part upper than an intermediate part of the column. The bottom stream (6C) (line 68), which is rich in higher-boiling components including acetic acid, is withdrawn from the bottom or a lower part of the column.

To remove impurities, the side-cut acetic acid stream (6B) (line 67) is further purified in the rectifying step (7), and a side-cut acetic acid stream (fourth acetic acid stream) (7B) from the rectifying step (7) is fed to the ion exchange step (8). A portion of the side-cut acetic acid stream (7B) (line 75) is sent via a line 76 and mixed with the bottom stream (5B) from the dehydration-distillation column (5).

The third overhead (6A) is cooled and condensed in a condenser to form a condensate 62, and the condensate 62 is then stored in a hold tank T3. A first portion of the condensate 62 is refluxed via a reflux line 63 to an upper part of the heavy ends column (6); and a second portion of the condensate 62 is recycled via a line 64 to the dehydration-distillation column (5). A third portion of the condensate 62 is fed respectively via a line 65 and a line 66 to the stripping step (18) in the offgas treatment section (15) and to the evaporation step (2). The non-condensable gas from the hold tank T3 may be fed to the reactor (1) or the evaporator (2).

Of the bottom stream (6C) (line 68), which contains acetic acid, a portion is returned to the heavy ends column (6); and the remainder is fed via a line 69 to an incineration unit (not shown).

The third overhead (6A) may have a composition typically as follows.

A component proportion in the reflux liquids (lines 62 and 63) and the condensates (lines 64 and 65) may be determined by subtracting the corresponding component proportions of a gas not condensed in the condenser and of a non-condensable gas from the hold tank T3, from the component proportion in the third overhead (6A).

TABLE 22

| Average molecular weight: 59.58 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 0.001 ppm to 0.1%) | 0.01 to 100 ppm | 0.1 to 10 ppm |
| CO | 0% to 1% (e.g., 0.01 ppm to 1%) | 0.1 ppm to 0.1 % | 10 ppm to 0.01% |
| $CO_2$ | 0% to 1% (e.g., 0.001 ppm to 0.1%) | 0.01 to 100 ppm | 0.1 to 10 ppm |
| $CH_4$ | 0% to 1% (e.g., 0.001 ppm to 0.1%) | 0.01 to 100 ppm | 0.1 to 10 ppm |
| $N_2$ | 0% to 1% (e.g., 0.001 ppm to 0.1%) | 0.01 to 100 ppm | 0.1 to 10 ppm |
| AD | 0% to 1% (e.g., 0.01 ppm to 0.1%) | 0.1 to 100 ppm | 0.2 to 50 ppm, 0.5 to 50 ppm |
| MeOH | 0% to 1% (e.g., 0.01 ppm to 0.1%) | 0.1 to 100 ppm | 0.5 to 50 ppm |
| MeI | 0% to 1% (e.g., 0.01 ppm to 0.1%) | 0.001 to 300 ppm (e.g., 0.1 to 100 ppm) | 0.003 to 50 ppm (e.g., 0.5 to 10 ppm) |
| MA | 0% to 1% (e.g., 1 ppm to 1%) | 0.1 ppm to 0.5% (e.g., 10 ppm to 0.1%) | 1 to 750 ppm (e.g., 50 to 500 ppm) |
| $H_2O$ | 10 ppm to 2% | 100 ppm to 1% | 0.1% to 0.5% |
| AcOH | 90% to 99.99% | 98% to 99.9% | 99% to 99.8% |
| HI | 0% to 1% (e.g., 0.1 ppb to 0.1%) | 1 ppb to 100 ppm | 2 ppb to 10 ppm (e.g., 10 ppb to 10 ppm) |
| FrOH | 0% to 1% (e.g., 0.1 ppm to 0.5%) | 1 ppm to 0.1% | 10 to 500 ppm |
| PrOH | 0% to 1% (e.g., 0.01 ppm to 0.1%) | 0.1 to 200 ppm | 1 to 50 ppm |
| DME | 0% to 1% (e.g., 0.01 ppm to 0.1%) | 0.1 to 200 ppm | 1 to 50 ppm |
| $(CH_3)_2C=O$ | 0% to 1% (e.g., 0.01 ppb to 10 ppm) | 0.1 ppb to 1 ppm | 1 ppb to 0.1 ppm |
| EtOH | 0% to 1% (e.g., 0.01 ppb to 10 ppm) | 0.1 ppb to 1 ppm | 1 ppb to 0.1 ppm |
| EA | 0% to 1% (e.g., 0.01 ppb to 10 ppm) | 0.1 ppb to 1 ppm | 1 ppb to 0.1 ppm |
| EtI | 0% to 1% (e.g., 0.01 ppb to 10 ppm) | 0.1 ppb to 1 ppm | 1 ppb to 0.1 ppm |
| Li | 0% to 0.1% (e.g., 0.01 ppt to 1 ppm) | 0.1 ppt to 0.1 ppm | 1 ppt to 0.01 ppm |
| Rh | 0% to 0.1% (e.g., 0.01 ppt to 1 ppm) | 0.1 ppt to 0.1 ppm | 1 ppt to 0.01 ppm |

The side-cut acetic acid stream (6B) (line 67) may have a composition typically as follows.

TABLE 23

| Average molecular weight: 60.01 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.001 ppm to 0.1%) | 0.01 to 100 ppm | 0.1 to 10 ppm |
| CO | 0% to 1% (e.g., 0.01 ppm to 1%) | 0.1 ppm to 0.1% | 10 ppm to 0.01% |
| $CO_2$ | 0% to 1% (e.g., 0.001 ppm to 0.1%) | 0.01 to 100 ppm | 0.1 to 10 ppm |
| $CH_4$ | 0% to 1% (e.g., 0.001 ppm to 0.1%) | 0.01 to 100 ppm | 0.1 to 10 ppm |
| $N_2$ | 0% to 1% (e.g., 0.001 ppm to 0.1%) | 0.01 to 100 ppm | 0.1 to 10 ppm |
| AD | 0% to 1% (e.g., 0.001 ppm to 0.1%) | 0.01 to 100 ppm | 0.1 to 10 ppm |
| MeOH | 0% to 1% (e.g., 0.1 ppb to 100 ppm) | 1 ppb to 10 ppm | 10 ppb to 1 ppm |
| MeI | 0% to 1% (e.g., 0.01 ppb to 20 ppb) | 0.1 ppb to 10 ppm | 0.5 to 5 ppb |
| MA | 0% to 1% (e.g., 0.001 ppm to 0.1%) | 0.01 to 100 ppm | 0.1 to 10 ppm |
| $H_2O$ | 0% to 1% (e.g., 1 ppm to 0.5%) | 10 ppm to 0.2% | 50 ppm to 0.1% |
| AcOH | 99% to 100% | 99.8% to 99.999% | 99.9% to 99.99% |
| HI | 0% to 1% (e.g., 0.01 to 100 ppb) | 0.1 to 10 ppb | 0.5 to 5 ppb |
| FrOH | 0% to 1% (e.g., 0.1 to 500 ppm) | 1 to 100 ppm | 5 to 50 ppm |
| PrOH | 0% to 1% (e.g., 0.1 ppm to 0.1%) | 1 to 500 ppm | 10 to 250 ppm |
| DME | 50 ppm or less (1 ppt to 50 ppm) | 1 ppb to 10 ppm | 10 ppb to 1 ppm |

TABLE 23-continued

| Average molecular weight: 60.01 | Range | Preferred range | More preferred range |
|---|---|---|---|
| $(CH_3)_2C=O$ | 0% to 1% (e.g., 0.01 ppb to 10 ppm) | 0.1 ppb to 1 ppm | 1 ppb to 0.1 ppm |
| EtOH | 0% to 1% (e.g., 0.01 ppb to 10 ppm) | 0.1 ppb to 1 ppm | 1 ppb to 0.1 ppm |
| EA | 0% to 1% (e.g., 0.01 ppb to 10 ppm) | 0.1 ppb to 1 ppm | 1 ppb to 0.1 ppm |
| EtI | 0% to 1% (e.g., 0.01 ppb to 10 ppm) | 0.1 ppb to 1 ppm | 1 ppb to 0.1 ppm |
| Li | 0% to 0.1% (e.g., 1 ppt to 1 ppm) | 10 ppt to 0.1 ppm | 100 ppt to 0.01 ppm |
| Rh | 0% to 0.1% (e.g., 1 ppt to 1 ppm) | 10 ppt to 0.1 ppm | 50 ppt to 0.01 ppm |

The bottom stream (6C) (line 68) may have a composition typically as follows.

TABLE 24

| Average molecular weight: 59.70 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppt to 100 ppm) | 10 ppt to 10 ppm | 1 ppb to 1 ppm |
| CO | 0% to 1% (e.g., 1 ppt to 0.1%) | 10 ppt to 100 ppm | 1 ppb to 10 ppm |
| $CO_2$ | 0% to 1% (e.g., 1 ppt to 100 ppm) | 10 ppt to 10 ppm | 1 ppb to 1 ppm |
| $CH_4$ | 0% to 1% (e.g., 1 ppt to 100 ppm) | 10 ppt to 10 ppm | 1 ppb to 1 ppm |
| $N_2$ | 0% to 1% (e.g., 1 ppt to 100 ppm) | 10 ppt to 10 ppm | 1 ppb to 1 ppm |
| AD | 0% to 1% (e.g., 1 ppt to 100 ppm) | 10 ppt to 10 ppm | 1 ppb to 1 ppm |
| MeOH | 0% to 1% (e.g., 1 ppt to 100 ppm) | 10 ppt to 10 ppm | 1 ppb to 1 ppm |
| MeI | 0% to 1% (e.g., 1 ppt to 10 ppm) | 10 ppt to 10 ppm | 0.1 ppb to 1 ppm |
| MA | 0% to 1% (e.g., 1 ppt to 100 ppm) | 0.01 to 10 ppm | 0.1 ppm to 1 ppm |
| $H_2O$ | 0% to 1% (e.g., 1 ppm to 0.5%) | 5 ppm to 0.1% | 20 ppm to 0.02% |
| AcOH | 80% to 99% | 85% to 98% | 90% to 95% |
| HI | 0% to 1% (e.g., 0.01 ppb to 100 ppm) | 0.1 ppb to 10 ppm | 0.5 ppb to 1 ppm |
| FrOH | 0% to 1% (e.g., 0.1 ppb to 0.5%) | 1 ppb to 0.1% | 10 ppb to 500 ppm |
| PrOH | 0% to 1% (e.g., 10 ppm to 10%) | 50 ppm to 1% | 100 ppm to 0.1% |
| DME | 1 ppm or less (1 ppt to 1 ppm) | 1 ppb to 10 ppm | 10 ppb to 1 ppm |
| $(CH_3)_2C=O$ | 0% to 1% (e.g., 0.01 ppb to 10 ppm) | 0.1 ppb to 1 ppm | 1 ppb to 0.1 ppm |
| KOH | 0.01% to 40% | 0.1% to 20% | 1% to 15%, e.g., 3% to 10% |
| EtOH | 0% to 1% (e.g., 0.01 ppb to 10 ppm) | 0.1 ppb to 1 ppm | 1 ppb to 0.1 ppm |
| EA | 0% to 1% (e.g., 0.01 ppb to 10 ppm) | 0.1 ppb to 1 ppm | 1 ppb to 0.1 ppm |
| EtI | 0% to 1% (e.g., 0.01 ppb to 10 ppm) | 0.1 ppb to 1 ppm | 1 ppb to 0.1 ppm |
| Li | 0% to 0.1% (e.g., 1 ppb to 100 ppm) | 10 ppb to 10 ppm | 100 ppb to 5 ppm |
| Rh | 0% to 0.1% (e.g., 0.1 ppb to 50 ppm) | 1 ppb to 2 ppm | 10 ppb to 1 ppm |
| Fe | 0% to 0.1% (e.g., 100 ppt to 100 ppm) | 1000 ppt to 50 ppm | 1000 ppt to 10 ppm |
| Ni | 0% to 0.1% (e.g., 10 ppt to 10 ppm) | 100 ppt to 1 ppm | 1000 ppt to 0.5 ppm |
| Cr | 0% to 0.1% (e.g., 10 ppt to 10 ppm) | 100 ppt to 1 ppm | 1000 ppt to 0.5 ppm |
| Mo | 0% to 0.1% (e.g., 10 ppt to 10 ppm) | 100 ppt to 1 ppm | 1000 ppt to 0.5 ppm |
| Zn | 0% to 0.1% (e.g., 10 ppt to 10 ppm) | 100 ppt to 1 ppm | 1000 ppt to 0.5 ppm |
| Cu | 0% to 0.1% (e.g., 10 ppt to 10 ppm) | 100 ppt to 1 ppm | 1000 ppt to 0.5 ppm |

The higher-boiling component-removing step (6) may include a step or steps. For example, it is acceptable that, while a portion of the bottom stream (6C) is returned to the heavy ends column (6), the remainder of the bottom stream (6C) is fed to a succeeding heavy ends column (6). The bottom stream(s) (6C) from a higher-boiling component-removing step or steps (in particular, the last higher-boiling component-removing step) may be discharged as a liquid waste. The heavy ends column(s) (6) for use herein may be selected typically from plate columns and packed columns.

Rectifying Step (7)

In the rectifying step (7), the acetic acid stream (6B) (line 67) from the higher-boiling component-removing step (6) is distilled in a rectifying column (7) to be separated into a fourth overhead (7A), a purified acetic acid (7B), and a bottom stream (7C). The fourth overhead (7A), which is rich in lower-boiling components, is withdrawn from the top or an upper part of the column via a line 71. The purified acetic acid (7B) is side-cut via a withdrawing line 75. The bottom stream (7C), which contains higher-boiling components, is withdrawn from the bottom or a lower part of the column via a bottom line 77.

The fourth overhead (7A) is cooled and condensed in a condenser in the line 71 to form a condensate and a non-condensable gas. Of the condensate from the condenser, a portion is refluxed via a line 72 to the rectifying column (7); and the remainder is fed via a line 73 to an incineration unit (not shown). The non-condensable gas (offgas) from the condenser is fed via a line 74 to an incineration unit (not shown). The non-condensable gas (offgas) may be recycled to the reactor.

A first portion of the bottom stream (7C) is heated in a reboiler (heat exchanger) on a line 80 by a vapor, where the vapor is a portion of the third overhead (6A) (line 61) from the heavy ends column (6), and is recycled to the rectifying column (7). Specifically, the thermal energy of the portion of the third overhead (6A) is given to the first portion of the bottom stream (7C) to serve as a heat source for the rectifying step (7).

A second portion of the bottom stream (7C) is heated by a reboiler (heater) on a line 78 and is recycled as a vapor to the rectifying column (7).

The portion of the third overhead (6A) cooled by the reboiler (heat exchanger) on the line 80 is stored in a hold tank T4 and is recycled, together with the remainder of the bottom stream (7C), via a line 79 also to the heavy ends column (6), for removal of higher-boiling components.

The side-cut purified acetic acid (7B) (line 75) is cooled in a condenser or cooler and is then fed via a line 81 to the ion exchange step (8), and the resulting purified acetic acid may be stored in a product tank T5.

The fourth overhead (7A) (line 71) may have a composition typically as follows.

TABLE 25

| | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 0.001 ppm to 0.1%) | 0.01 to 100 ppm | 0.1 to 10 ppm |
| CO | 0% to 1% (e.g., 0.01 ppm to 1%) | 0.1 ppm to 0.1% | 10 ppm to 0.01% |
| $CO_2$ | 0% to 1% (e.g., 0.001 ppm to 0.1%) | 0.01 to 100 ppm | 0.1 to 10 ppm |
| $CH_4$ | 0% to 1% (e.g., 0.001 ppm to 0.1%) | 0.01 to 100 ppm | 0.1 to 10 ppm |
| $N_2$ | 0% to 1% (e.g., 0.001 ppm to 0.1%) | 0.01 to 100 ppm | 0.1 to 10 ppm |
| AD | 0% to 1% (e.g., 0.01 ppm to 0.1%) | 0.1 to 100 ppm | 0.5 to 50 ppm |
| MeOH | 0% to 1% (e.g., 0.01 ppm to 0.1%) | 0.1 to 100 ppm | 0.5 to 50 ppm |
| MeI | 0% to 1% (e.g., 1 ppb to 0.1%) | 0.01 to 100 ppm | 0.1 to 10 ppm |
| MA | 0% to 5% (e.g., 1 ppm to 3%) | 10 ppm to 2% | 100 ppm to 1% |
| $H_2O$ | 0.1% to 50% | 1% to 30% | 10% to 30% |
| AcOH | 50% to 99% | 60% to 95% | 70% to 90% |
| HI | 0% to 1% (e.g., 0.01 ppb to 0.1%) | 0.1 ppb to 100 ppm | 1 ppb to 10 ppm |
| FrOH | 0% to 1% (e.g., 10 ppm to 3%) | 100 ppm to 2% | 0.1% to 1% |
| PrOH | 0% to 1% (e.g., 0.01 ppm to 0.1%) | 0.1 to 200 ppm | 1 to 50 ppm |
| DME | 0% to 1% (e.g., 1 ppb to 0.1%) | 10 ppb to 200 ppm | 100 ppb to 50 ppm |
| $(CH_3)_2C=O$ | 0% to 1% (e.g., 0.01 ppb to 10 ppm) | 0.1 ppb to 1 ppm | 1 ppb to 0.1 ppm |
| EtOH | 0% to 1% (e.g., 0.01 ppb to 10 ppm) | 0.1 ppb to 1 ppm | 1 ppb to 0.1 ppm |
| EA | 0% to 1% (e.g., 0.01 ppb to 10 ppm) | 0.1 ppb to 1 ppm | 1 ppb to 0.1 ppm |
| EtI | 0% to 1% (e.g., 0.01 ppb to 10 ppm) | 0.1 ppb to 1 ppm | 1 ppb to 0.1 ppm |
| Li | 0% to 0.1% (e.g., 0.01 ppt to 0.1 ppm) | 0.1 ppt to 0.01 ppm | 1 ppt to 0.001 ppm |
| Rh | 0% to 0.1% (e.g., 0.01 ppt to 0.1 ppm) | 0.1 ppt to 0.01 ppm | 1 ppt to 0.001 ppm |

The condensates 72 and 73 may typically have compositions approximately identical to or similar to the composition of the fourth overhead (7A) (line 71). A component proportion in the compositions of the condensates 72 and 73 may be determined by subtracting the corresponding component proportion in the offgas 74 from the component proportion in the fourth overhead (7A) (line 71).

The offgas 74 may have a composition typically as follows.

Assume that the rectifying column (7) is purged with an inert gas (such as nitrogen gas or carbon monoxide gas), so as to regulate the pressure of the rectifying column (7) and/or to protect the measuring instruments, as described above. In this case, for example, the concentration of the inert gas, such as the nitrogen concentration column, in the following table significantly increases depending on the amount of the introduced inert gas.

TABLE 26

| | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 1 ppb to 1%) | 0.01 ppm to 0.5% | 0.1 to 500 ppm |
| CO | 0% to 1% (e.g., 1 ppm to 99.9%) | 10 ppm to 99% | 100 ppm to 98% |
| $CO_2$ | 0% to 1% (e.g., 1 ppb to 1%) | 0.01 ppm to 0.5% | 0.1 to 500 ppm |
| $CH_4$ | 0% to 1% (e.g., 1 ppb to 1%) | 0.01 ppm to 0.5% | 0.1 to 500 ppm |
| $N_2$ | 0% to 1% (e.g., 1 ppm to 80%) | 10 ppm to 75% | 100 ppm to 70% |

TABLE 26-continued

| | Range | Preferred range | More preferred range |
|---|---|---|---|
| AD | 0% to 1% (e.g., 0.1 ppm to 0.5%) | 1 ppm to 0.1% | 10 to 500 ppm |
| MeOH | 0% to 1% (e.g., 0.1 ppm to 0.5%) | 1 ppm to 0.1% | 10 to 500 ppm |
| MeI | 1 ppm to 5% | 10 ppm to 3% | 100 ppm to 1% |
| MA | 1 ppm to 20% | 10 ppm to 5% | 100 ppm to 1% |
| $H_2O$ | 10 ppm to 30% | 100 ppm to 20% | 0.1% to 10% |
| AcOH | 10 ppm to 30% | 100 ppm to 20% | 0.1% to 10% |
| HI | 0% to 1% (e.g., 1 ppb to 0.1%) | 10 ppb to 0.01% | 100 ppb to 0.001% |
| FrOH | 0% to 1% (e.g., 0.1 ppm to 1%) | 1 ppm to 0.5% | 10 ppm to 0.1% |
| PrOH | 0% to 1% (e.g., 0.01 ppm to 0.1%) | 0.1 ppm to 0.05% | 1 ppm to 0.01% |
| DME | 0% to 1% (e.g., 0.01 ppm to 0.1%) | 0.1 ppm to 0.05% | 1 ppm to 0.01% |
| $(CH_3)_2C{=}O$ | 0% to 1% (e.g., 0.01 ppb to 10 ppm) | 0.1 ppb to 1 ppm | 1 ppb to 0.1 ppm |
| EtOH | 0% to 1% (e.g., 0.01 ppb to 10 ppm) | 0.1 ppb to 1 ppm | 1 ppb to 0.1 ppm |
| EA | 0% to 1% (e.g., 0.01 ppb to 10 ppm) | 0.1 ppb to 1 ppm | 1 ppb to 0.1 ppm |
| EtI | 0% to 1% (e.g., 0.01 ppb to 10 ppm) | 0.1 ppb to 1 ppm | 1 ppb to 0.1 ppm |
| Li | 0% to 0.1% (e.g., 0.01 ppt to 0.1 ppm) | 0.1 ppt to 0.01 ppm | 1 ppt to 0.001 ppm |
| Rh | 0% to 0.1% (e.g., 0.01 ppt to 0.1 ppm) | 0.1 ppt to 0.01 ppm | 1 ppt to 0.001 ppm |

The side-cut purified acetic acid (7B) (line 75) may have a composition typically as follows.

TABLE 27

| | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.001 ppm to 0.1%) | 0.01 to 100 ppm | 0.1 to 10 ppm |
| CO | 0% to 1% (e.g., 0.01 ppm to 1%) | 0.1 ppm to 0.1% | 1 to 100 ppm |
| $CO_2$ | 0% to 1% (e.g., 0.001 ppm to 0.1%) | 0.01 to 100 ppm | 0.1 to 10 ppm |
| $CH_4$ | 0% to 1% (e.g., 0.001 ppm to 0.1%) | 0.01 to 100 ppm | 0.1 to 10 ppm |
| $N_2$ | 0% to 1% (e.g., 0.001 ppm to 0.1%) | 0.01 to 100 ppm | 0.1 to 10 ppm |
| AD | 0% to 1% (e.g., 0.001 to 100 ppm) | 0.01 to 50 ppm | 0.1 to 10 ppm |
| MeOH | 0% to 1% (e.g., 0.1 ppb to 100 ppm) | 1 ppb to 10 ppm | 10 ppb to 1 ppm |
| MeI | 0% to 0.1% (e.g., 1 ppt to 20 ppb) | 10 ppt to 10 ppb | 100 ppt to 5 ppb |
| MA | 0% to 1% (e.g., 1 ppb to 100 ppm) | 5 ppb to 50 ppm (e.g., 10 ppb to 10 ppm) | 50 ppb to 25 ppm (e.g., 100 ppb to 5 ppm) |
| $H_2O$ | 0% to 1% (e.g., 1 ppm to 0.5%) | 10 ppm to 0.2% | 50 ppm to 0.1% |
| AcOH | 99.8% to 100% | 99.9% to 99.999% | 99.95% to 99.99% |
| HI | 0% to 0.1% (e.g., 1 ppt to 20 ppb) | 10 ppt to 10 ppb | 100 ppt to 5 ppb |
| TOI | 0% to 1% (e.g., 0.1 ppb to 0.1%) | 1 ppb to 100 ppm | 10 ppb to 10 ppm |
| HexI | 0% to 0.1% (e.g., 1 ppt to 20 ppb) | 10 ppt to 10 ppb | 100 ppt to 5 ppb |
| FrOH | 0% to 1% (e.g., 0.1 to 500 ppm) | 1 to 100 ppm | 5 to 50 ppm |
| PrOH | 0% to 1% (e.g., 0.1 ppm to 0.1%) | 1 to 500 ppm | 10 to 250 ppm |
| DME | 0% to 1% (e.g., 1 ppt to 50 ppm) | 1 ppb to 10 ppm | 10 ppb to 1 ppm |
| AcA | 0% to 1% (e.g., 0.1 ppb to 0.1%) | 1 ppb to 100 ppm | 10 ppb to 10 ppm |
| $(CH_3)_2C{=}O$ | 0% to 1% (e.g., 0.01 ppb to 10 ppm) | 0.1 ppb to 1 ppm | 1 ppb to 0.1 ppm |
| EtOH | 0% to 1% (e.g., 0.01 ppb to 10 ppm) | 0.1 ppb to 1 ppm | 1 ppb to 0.1 ppm |
| EA | 0% to 1% (e.g., 0.01 ppb to 10 ppm) | 0.1 ppb to 1 ppm | 1 ppb to 0.1 ppm |
| EtI | 0% to 1% (e.g., 0.01 ppb to 10 ppm) | 0.1 ppb to 1 ppm | 1 ppb to 0.1 ppm |
| Li | 0% to 0.1% (e.g., 0.01 to 100 ppb) | 0.1 to 10 ppb | 0.5 to 5 ppb |
| Rh | 0% to 0.1% (e.g., 1 ppt to 50 ppb) | 10 ppt to 10 ppb | 50 ppt to 3 ppb |

Cooling of the side-cut purified acetic acid (7B) in the condenser seems to hardly give a non-condensable gas. For example, the purified acetic acid (7B), even when cooled, has a proportion of a non-condensable gas or gases of 1 percent by mass or less (e.g., about 0.1 percent by mass or less) of the totality of fluids. Accordingly, the purified acetic acid (line 81) from the condenser is different only in temperature (e.g., 17° C. to 60° C.) from the purified acetic acid (7B), but has a composition approximately identical to or similar to the composition of the purified acetic acid (7B).

The bottom stream (7C) (lines 77, 78, and 79) has a composition approximately identical to or similar to the composition of the side-cut purified acetic acid (7B) (line 75), except the concentration typically of Li and/or Rh. The concentrations of Li and Rh may typically be as follows. Oxygen, if included in the rectifying column (7), causes not only coloring of the side-cut purified acetic acid (7B) (line 75), but also stronger coloring of the bottom stream (7C).

TABLE 28

| | Range | Preferred range | More preferred range |
|---|---|---|---|
| Li | 1 ppm or less (0.1 ppb to 1000 ppb) | 1 to 100 ppb | 5 to 50 ppb |
| Rh | 1 ppm or less (10 ppt to 500 ppb) | 100 ppt to 100 ppb | 500 ppt to 30 ppb |

Ion-Exchange Step (8)

In the ion exchange step (8), the acetic acid stream (7B) from the rectifying step (7) is cooled and treated in an ion exchange tank (8) to separate iodine compounds from the acetic acid stream (7B) to thereby form a purified acetic acid stream (fifth acetic acid stream) (8A). The purified acetic acid stream (8A) is sent via a line 82 to the product tank T5 for storage.

For example, the concentration of oxygen and the composition of other components in the acetic acid stream 82, which has been treated in the ion exchange tank (8), may be approximately identical to or similar to those of the side-cut purified acetic acid (7B) (line 75), except the concentrations of components that have been removed by the ion exchange.

An ion exchanger for use in the ion exchange tank (8) may be selected from ion exchangers that can remove or adsorb iodine compounds. Non-limiting examples of such ion exchangers include zeolite, activated carbon, and ion exchange resins, of which cation-exchange resins are typified. The cation-exchange resin(s) may be selected from weakly acidic cation-exchange resins, but is preferably selected from strongly acidic cation-exchange resins such as macroreticular ion exchange resins. The ion exchanger may have active sites being substituted with or replaced with a metal or metals at least partially. In other words, the ion exchanger may be a metal-supported ion exchanger. Non-limiting examples of the active sites include cationic groups such as sulfone groups, carboxy groups, phenolic hydroxy groups, and phosphonic groups. Non-limiting examples of the metals include silver (Ag), mercury (Hg), and copper (Cu). For example, the ion exchanger may be a metal-supported ion exchanger with typically about 10 to about 80 mole percent, preferably about 25 to about 75 mole percent, and more preferably about 30 to about 70 mole percent, of the active sites in the ion exchanger being substituted with or replaced with a metal (such as silver).

The ion exchanger (such as a silver-supported ion exchange resin) is generally housed in or packed in an ion exchange column or treatment unit. Contact of the acetic acid stream with the ion exchanger enables removal of iodine compounds, where the contact is preferably performed by passing the acetic acid stream through the ion exchanger. Contact of the acetic acid stream with (or passing of the acetic acid stream through) the ion exchange resin with heating of the acetic acid stream continuously or stepwise as needed enables efficient removal of the iodine compounds while eliminating or minimizing leakage of the metal from the ion exchanger (ion exchange resin). Non-limiting examples of the ion exchange column include packed columns which are packed with at least an ion exchanger (such as a metal-supported ion exchanger); and columns each including, for example, an ion exchanger bed (such as a bed made of a granular ion exchanger (guard bed)). The ion exchange column may further house or be packed with one or more other ion exchangers (such as cation-exchange resins, anion-exchange resins, and nonion-exchange resins), in addition to the ion exchanger. The ion exchange treatment of the acetic acid stream may be performed typically using a column housing or being packed with the ion exchanger, in combination with a column housing or being packed with another ion exchanger. For example, the treatment unit for use herein may include an anion-exchange resin column in combination with an ion exchange column including a metal-supported ion exchange resin, where the metal-supported ion exchange resin is disposed downstream from, or upstream from, the anion-exchange resin column. The details of the former embodiment can be found typically in PCT International Publication Number WO02/062740.

The ion exchange treatment may be performed at a temperature of typically about 18° C. to about 100° C., preferably about 30° C. to about 70° C., and more preferably about 40° C. to about 60° C.; at a flow rate of the acetic acid stream of typically about 3 to about 15 bed volume/hr, preferably about 5 to about 12 bed volume/hr, and more preferably about 6 to about 10 bed volume/hr, typically in a removing column using a guard bed.

The purification section (4) may include at least one step selected from the group consisting of the dehydrating step (5), the higher-boiling component-removing step (6), the rectifying step (7), and the ion exchange step (8), and generally often includes the dehydrating step (5) and the higher-boiling component-removing step (6). The ion exchange step (8) may be performed after any step in the purification section (4), such as at least one of the dehydrating step (5) and the higher-boiling component-removing step (6), or may be performed between the higher-boiling component-removing step (6) and the rectifying step (7).

Separation Section (9)

The first overhead (3A) from the lower-boiling component-removing step (3) contains impurities and useful components, such as PRC's, methyl iodide, and methyl acetate, as described above. Thus, at least acetaldehyde is removed from the first overhead (3A) in the separation section (9). In particular, in the separation section (9), the first overhead (3A) is separated into a stream rich in acetaldehyde, and a stream rich in useful methyl iodide.

The separation section (9) may include (10) a liquid-liquid separation step, (11) a first aldehyde separation step, (12) an extraction step, (13) a second aldehyde separation step, and (14) an alkane separation step. The liquid-liquid separation step (10) is the step of condensing the first overhead (3A) to give two phases (an upper phase and a lower phase). The first aldehyde separation step (fifth distillation step) (11) is the step of forming a fifth overhead from at least one of the upper phase and the lower phase, where the fifth overhead is rich in acetaldehyde and methyl iodide. The extraction step (sixth distillation step) (12) is the step of extracting acetaldehyde from the fifth overhead and thereby separating the fifth overhead into an extract and a raffinate, where the extract is rich in acetaldehyde, and the raffinate is rich in methyl iodide. The second aldehyde separation step (seventh distillation step) (13) is the step of separating aldehyde from at least one of the extract and the raffinate. The alkane separation step (eighth distillation step) (14) is the step of separating an alkane or alkanes from at least one of the upper phase and the lower phase.

Liquid-Liquid Separation Step (10)

In the liquid-liquid separation step (10), the first overhead (3A) (line 31) is cooled and condensed in a condenser to give a condensate 32 and a non-condensable gas 33. The condensate 32 is rich in methyl iodide and contains other components such as water. The condensate 32 is separated into an aqueous phase 38 and an organic phase 39 in the decanter S2. A portion of the condensate (upper phase) is refluxed via a reflux line 41 to the splitter column (3). In addition, at least a portion of the upper phase (aqueous phase or lighter phase rich in acetaldehyde) 38, which has been separated in the decanter S2; and at least a portion of the lower phase (organic phase or heavier phase rich in methyl iodide) 39 are recycled respectively via the line 41 and the line 40 to the reactor (1).

At least a portion of the lower phase, which has been separated in the decanter S2 and is rich in methyl iodide, is fed via feed lines 111 and 112 to a fifth distillation column (11) to form the fifth overhead rich in acetaldehyde and methyl iodide. The lower phase, which is rich in methyl iodide, from the decanter S2 is mixed with a portion (branch stream) 124 of a bottom stream (11B) (line 123) from the fifth distillation column (11) and is recycled to the reactor (1).

The non-condensable gas (offgas) 33, which has not been condensed in the condenser, is rich in methyl iodide and contains other components such as carbon monoxide. The non-condensable-gas is, together with a non-condensable gas from the decanter S2, sent via lines 34, 35, and 37 to the offgas treatment section (15) for treatment, as with the offgas. The non-condensable gas (offgas) is further cooled and condensed in a condenser on the line 34 to give a condensate and a non-condensable gas. The condensate is sent via a line 36, mixed with the lower phase 39 from the feed line 111; whereas the non-condensable gas is fed via the line 35 to a decanter S3. A condensate liquefied in the decanter S3 is mixed with the lower phase 39 in the feed line 112. A non-condensable gas from the decanter S3 is sent via the line 37 to the offgas treatment section (15) for treatment.

The condensate 32 may typically have a composition approximately identical to or similar to the composition of the first overhead (3A) (line 31). A component proportion in the condensate 32 may be determined by subtracting the corresponding component proportion in the non-condensable gas (offgas) 33, which has not been condensed in the condenser, from the component proportion in the first overhead (3A).

The upper phase 38 from decanter S2 may have a composition typically as follows.

TABLE 29

| Average molecular weight: 23.26 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.1 ppm to 1%) | 1 ppm to 0.1% | 2 ppm to 0.1% |
| CO | 0% to 1% (e.g., 0.1 ppm to 1%) | 1 ppm to 0.1% | 10 ppm to 0.05% |
| $CO_2$ | 0% to 1% (e.g., 0.1 ppm to 1%) | 1 ppm to 0.1% | 10 ppm to 0.05% |
| $CH_4$ | 0% to 1% (e.g., 0.1 ppm to 1%) | 1 ppm to 0.1% | 2 ppm to 0.1% |
| $N_2$ | 0% to 1% (e.g., 0.1 ppm to 1%) | 1 ppm to 0.1% | 2 ppm to 0.1% |
| AD | 0% to 2% (e.g., 0.01% to 2%) | 0.05% to 1% | 0.1% to 0.7% |
| MeOH | 0% to 10% (e.g., 10 ppm to 10%) | 100 ppm to 5% | 0.1% to 3% |
| MeI | 0.1% to 15% | 1% to 10% | 2% to 6% |
| MA | 1% to 40% | 5% to 30% | 10% to 25% |
| $H_2O$ | 10% to 95% | 20% to 90% | 40% to 80% |
| AcOH | 1% to 30% | 3% to 20% | 8% to 15% |
| HI | 0% to 1% (e.g., 0.01 ppm to 1%) | 0.1 ppm to 0.5% | 1 ppm to 0.1% |
| FrOH | 0% to 1% (e.g., 0.1 ppm to 1%) | 1 ppm to 0.5% | 10 ppm to 0.1% |
| PrOH | 0% to 1% (e.g., 0.1 ppm to 0.1%) | 1 to 100 ppm | 3 to 50 ppm |
| DME | 0% to 1% (e.g., 0.1 ppm to 1%) | 1 ppm to 0.1% | 10 ppm to 0.05% |
| $(CH_3)_2C=O$ | 0% to 1% (e.g., 1 ppm to 0.5%) | 10 ppm to 0.2% | 50 ppm to 0.1% |
| EtOH | 0% to 1% (e.g., 1 ppm to 0.5%) | 10 ppm to 0.2% | 50 ppm to 0.1% |
| EA | 0% to 1% (e.g., 1 ppm to 0.5%) | 10 ppm to 0.2% | 50 ppm to 0.1% |
| EtI | 0% to 1% (e.g., 1 ppm to 0.5%) | 10 ppm to 0.2% | 50 ppm to 0.1% |
| Li | 0% to 0.1% (e.g., 0.01 ppt to 0.1 ppm) | 0.1 ppt to 0.01 ppm | 1 ppt to 0.001 ppm |
| Rh | 0% to 0.1% (e.g., 0.01 ppt to 0.1 ppm) | 0.1 ppt to 0.01 ppm | 1 ppt to 0.001 ppm |

The upper phase in the line 41, which leads to the reactor (1) and the splitter column (3), may also typically have a composition approximately identical to or similar to the composition of the upper phase 38 from the decanter S2.

The lower phase 39 in the decanter S2 may have a composition typically as follows.

TABLE 30

| Average molecular weight: 119.79 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm | 10 ppt to 300 ppm, e.g., 100 ppt to 100 ppm |
| $H_2$ | 0 % to 1 % (e.g., 0.1 ppm to 1%) | 1 ppm to 0.1% | 2 ppm to 0.1% |
| CO | 0% to 1% (e.g., 0.1 ppm to 1%) | 1 ppm to 0.1% | 10 ppm to 0.05% |
| $CO_2$ | 0% to 1% (e.g., 0.1 ppm to 1%) | 1 ppm to 0.1% | 10 ppm to 0.05% |
| $CH_4$ | 0% to 1% (e.g., 0.1 ppm to 1%) | 1 ppm to 0.1% | 2 ppm to 0.1% |
| $N_2$ | 0 % to 1 % (e.g., 0.1 ppm to 1%) | 1 ppm to 0.1% | 2 ppm to 0.1% |
| AD | 0% to 2% (e.g., 0.01% to 2%) | 0.05% to 1% | 0.08% to 0.5% |
| MeOH | 0% to 2% (e.g., 1 ppm to 2%) | 10 ppm to 1% | 100 ppm to 0.3% |

TABLE 30-continued

| Average molecular weight: 119.79 | Range | Preferred range | More preferred range |
|---|---|---|---|
| MeI | 20% to 99% | 40% to 95% | 60% to 92% |
| MA | 1% to 40% | 4% to 30% | 7% to 20% |
| $H_2O$ | 0.01% to 20% | 0.1% to 10% | 0.5% to 3% |
| AcOH | 0.01% to 20% | 0.1% to 10% | 0.5% to 3% |
| HI | 0% to 1% (e.g., 0.01 ppm to 0.1%) | 0.1 to 500 ppm | 1 to 100 ppm |
| FrOH | 0% to 1% (e.g., 0.1 ppm to 0.1%) | 1 to 100 ppm | 3 to 50 ppm |
| PrOH | 0% to 1% (e.g., 0.1 ppm to 0.1%) | 1 to 100 ppm | 3 to 30 ppm |
| DME | 0% to 1% (e.g., 1 ppm to 1%) | 10 ppm to 0.5% | 100 ppm to 0.1% |
| $(CH_3)_2C{=}O$ | 0% to 1% (e.g., 1 ppm to 0.5%) | 10 ppm to 0.2% | 50 ppm to 0.1% |
| EtOH | 0% to 1% (e.g., 1 ppm to 0.5%) | 10 ppm to 0.2% | 50 ppm to 0.1% |
| EA | 0% to 1% (e.g., 1 ppm to 0.5%) | 10 ppm to 0.2% | 50 ppm to 0.1% |
| EtI | 0% to 1% (e.g., 1 ppm to 0.5%) | 10 ppm to 0.2% | 50 ppm to 0.1% |
| Li | 0% to 0.1% (e.g., 0.01 ppt to 0.1 ppm) | 0.1 ppt to 0.01 ppm | 1 ppt to 0.001 ppm |
| Rh | 0% to 0.1% (e.g., 0.01 ppt to 0.1 ppm) | 0.1 ppt to 0.01 ppm | 1 ppt to 0.001 ppm |

The non-condensable gas (offgas) (line 33) from the condenser may have a composition typically as follows.

TABLE 31

| Average molecular weight: 79.89 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 1 ppm to 5% | 5 ppm to 2.5% (e.g., 10 ppm to 1%) | 50 ppm to 1% (e.g., 100 ppm to 0.1%) |
| CO | 0.01% to 50% | 0.1% to 30% | 1% to 15% |
| $CO_2$ | 0.01% to 20% | 0.1% to 10% | 0.5% to 5% |
| $CH_4$ | 1 ppm to 10% | 10 ppm to 3% | 100 ppm to 1% |
| $N_2$ | 1 ppm to 10% | 10 ppm to 3% | 100 ppm to 1% |
| AD | 1 ppm to 10% | 10 ppm to 3% | 100 ppm to 1% |
| MeOH | 0% to 1% (e.g., 0.1 ppm to 1%) | 1 ppm to 0.5% | 10 ppm to 0.1% |
| MeI | 1% to 99% | 10% to 95% | 40% to 90% |
| MA | 0.01% to 50% | 0.1% to 20% | 1% to 10% |
| $H_2O$ | 0.001% to 20% | 0.01% to 10% | 0.1% to 5% |
| AcOH | 0.001% to 20% | 0.01% to 10% | 0.1% to 5% |
| HI | 0% to 1% (e.g., 1 ppb to 0.1%) | 10 ppb to 0.01% | 100 ppb to 0.001% |
| FrOH | 0% to 1% (e.g., 1 ppb to 0.1%) | 10 ppb to 0.01% | 100 ppb to 0.001% |
| PrOH | 0% to 1% (e.g., 1 ppb to 0.1%) | 10 ppb to 0.01% | 100 ppb to 0.001% |
| DME | 0% to 10% (e.g., 0.1 ppm to 10%) | 1 ppm to 2% | 10 ppm to 1% |
| $(CH_3)_2C{=}O$ | 0% to 1% (e.g., 0.01 ppm to 1%) | 0.1 ppm to 0.1% | 1 ppm to 0.05% |
| EtOH | 0% to 1% (e.g., 0.01 ppm to 1%) | 0.1 ppm to 0.1% | 1 ppm to 0.05% |
| EA | 0% to 1% (e.g., 0.01 ppm to 1%) | 0.1 ppm to 0.1% | 1 ppm to 0.05% |
| EtI | 0% to 1% (e.g., 0.01 ppm to 1%) | 0.1 ppm to 0.1% | 1 ppm to 0.05% |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

The non-condensable gas in the line 34 may have a composition typically as follows.

TABLE 32

| Average molecular weight: 82.08 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |

TABLE 32-continued

| Average molecular weight: 82.08 | Range | Preferred range | More preferred range |
|---|---|---|---|
| | 0.1 ppb to 2%), e.g., 1 ppb to 1% (e.g., 10 ppb to 0.5%) | | |
| $H_2$ | 1 ppm to 5% | 10 ppm to 1% | 100 ppm to 0.1% |
| CO | 0.01% to 50% | 0.1% to 30% | 1% to 15% |
| $CO_2$ | 0.01% to 20% | 0.1% to 10% | 0.5% to 5% |
| $CH_4$ | 1 ppm to 10% | 10 ppm to 3% | 100 ppm to 1% |
| $N_2$ | 1 ppm to 10% | 10 ppm to 3% | 100 ppm to 1% |
| AD | 1 ppm to 10% | 10 ppm to 3% | 100 ppm to 1% |
| MeOH | 0% to 1% (e.g., 0.1 ppm to 1%) | 1 ppm to 0.5% | 10 ppm to 0.1% |
| MeI | 1% to 99% | 10% to 95% | 40% to 90% |
| MA | 0.01% to 50% | 0.1% to 20% | 1% to 20% |
| $H_2O$ | 0.001% to 20% | 0.01% to 10% | 0.1% to 5% |
| AcOH | 0.001% to 20% | 0.01% to 10% | 0.1% to 5% |
| HI | 0% to 1% (e.g., 1 ppb to 0.1%) | 10 ppb to 0.01% | 100 ppb to 0.001% |
| FrOH | 0% to 1% (e.g., 1 ppb to 0.1%) | 10 ppb to 0.01% | 100 ppb to 0.001% |
| PrOH | 0% to 1% (e.g., 1 ppb to 0.1%) | 10 ppb to 0.01% | 100 ppb to 0.001% |
| DME | 0% to 10% (e.g., 0.1 ppm to 10%) | 1 ppm to 2% | 10 ppm to 1% |
| $(CH_3)_2C=O$ | 0% to 1% (e.g., 0.01 ppm to 1%) | 0.1 ppm to 0.1% | 1 ppm to 0.05% |
| EtOH | 0% to 1% (e.g., 0.01 ppm to 1%) | 0.1 ppm to 0.1% | 1 ppm to 0.05% |
| EA | 0% to 1% (e.g., 0.01 ppm to 1%) | 0.1 ppm to 0.1% | 1 ppm to 0.05% |
| EtI | 0% to 1% (e.g., 0.01 ppm to 1%) | 0.1 ppm to 0.1% | 1 ppm to 0.05% |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

The non-condensable gas in the line 35 may have a composition typically as follows.

TABLE 33

| Average molecular weight: 42.11 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 1 ppm to 10% | 10 ppm to 5% | 100 ppm to 1% |
| CO | 0.01% to 90% | 0.1% to 70% | 1% to 50% |
| $CO_2$ | 0.01% to 30% | 0.1% to 20% | 0.5% to 10% |
| $CH_4$ | 10 ppm to 20% | 100 ppm to 10% | 0.1% to 5% |
| $N_2$ | 10 ppm to 20% | 100 ppm to 10% | 0.1% to 5% |
| AD | 1 ppm to 10% | 10 ppm to 3% | 100 ppm to 1% |
| MeOH | 0% to 1% (e.g., 0.1 ppm to 1%) | 1 ppm to 0.5% | 10 ppm to 0.1% |
| MeI | 1% to 99% | 10% to 90% | 20% to 70% |
| MA | 0.01% to 50% | 0.1% to 20% | 1% to 10% |
| $H_2O$ | 0.001% to 20% | 0.01% to 10% | 0.1% to 5% |
| AcOH | 0% to 10% (e.g., 1 ppm to 10%) | 10 ppm to 5% | 100 ppm to 1% |
| HI | 0% to 1% (e.g., 1 ppb to 0.1%) | 10 ppb to 0.01% | 100 ppb to 0.001% |
| FrOH | 0% to 1% (e.g., 1 ppb to 0.1%) | 10 ppb to 0.01% | 100 ppb to 0.001% |
| PrOH | 0% to 1% (e.g., 1 ppb to 0.1%) | 10 ppb to 0.01% | 100 ppb to 0.001% |
| DME | 0% to 10% (e.g., 0.1 ppm to 10%) | 1 ppm to 2% | 10 ppm to 1% |
| $(CH_3)_2C=O$ | 0% to 1% (e.g., 0.01 ppm to 1%) | 0.1 ppm to 0.1% | 1 ppm to 0.05% |
| EtOH | 0% to 1% (e.g., 0.01 ppm to 1%) | 0.1 ppm to 0.1% | 1 ppm to 0.05% |
| EA | 0% to 1% (e.g., 0.01 ppm to 1%) | 0.1 ppm to 0.1% | 1 ppm to 0.05% |
| EtI | 0% to 1% (e.g., 0.01 ppm to 1%) | 0.1 ppm to 0.1% | 1 ppm to 0.05% |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

The condensate in the line 36 may have a composition typically as follows.

TABLE 34

| Average molecular weight: 112.80 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.01 ppm to 1%) | 0.1 ppm to 0.1% | 1 ppm to 0.01% |
| CO | 0% to 1% (e.g., 1 ppm to 1%) | 10 ppm to 0.5% | 100 ppm to 0.1% |
| $CO_2$ | 1 ppm to 1% | 10 ppm to 0.5% | 100 ppm to 0.2% |
| $CH_4$ | 0% to 1% (e.g., 0.1 ppm to 0.1%) | 1 ppm to 0.05% | 10 ppm to 0.01% |
| $N_2$ | 0% to 1% (e.g., 0.1 ppm to 0.1%) | 1 ppm to 0.05% | 10 ppm to 0.01% |
| AD | 100 ppm to 3% | 0.1% to 1% | 0.2% to 6000 ppm |
| MeOH | 0% to 1% (e.g., 1 ppm to 1%) | 10 ppm to 0.5% | 100 ppm to 0.3% |
| MeI | 20% to 99% | 50% to 97% | 70% to 90% |
| MA | 1% to 40% | 5% to 30% | 7% to 20% |
| $H_2O$ | 0.01% to 10% | 0.1% to 8% | 0.5% to 5% |
| AcOH | 0.001% to 5% | 0.01% to 1% | 0.05% to 0.5% |
| HI | 0% to 1% (e.g., 0.01 ppm to 0.1%) | 0.1 to 500 ppm | 1 to 100 ppm |
| FrOH | 0% to 1% (e.g., 0.1 ppm to 0.1%) | 1 to 100 ppm | 3 to 50 ppm |
| PrOH | 0% to 1% (e.g., 0.1 ppm to 0.1%) | 1 to 100 ppm | 3 to 30 ppm |
| DME | 0% to 3% (e.g., 1 ppm to 3%) | 10 ppm to 2% | 100 ppm to 1% |
| $(CH_3)_2C{=}O$ | 0% to 1% (e.g., 0.01 ppm to 1%) | 0.1 ppm to 0.1% | 1 ppm to 0.05% |
| EtOH | 0% to 1% (e.g., 0.01 ppm to 1%) | 0.1 ppm to 0.1% | 1 ppm to 0.05% |
| EA | 0% to 1% (e.g., 0.01 ppm to 1%) | 0.1 ppm to 0.1% | 1 ppm to 0.05% |
| EtI | 0% to 1% (e.g., 0.01 ppm to 1%) | 0.1 ppm to 0.1% | 1 ppm to 0.05% |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

The non-condensable gas in the line 37 from the decanter S3 may have a composition typically as follows.

TABLE 35

| Average molecular weight: 42.11 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.01% to 5% | 0.05% to 2% | 0.1% to 1% |
| CO | 1% to 99% | 5% to 80% | 10% to 70% |
| $CO_2$ | 0.1% to 20% | 0.5% to 15% | 1% to 15% |
| $CH_4$ | 0.1% to 20% | 0.5% to 15% | 1% to 10% |
| $N_2$ | 0.1% to 20% | 0.5% to 15% | 1% to 10% |
| AD | 0% to 10% (e.g., 0.001% to 10%) | 0.01% to 5% | 0.1% to 3% |
| MeOH | 0% to 1% (e.g., 1 ppm to 1%) | 5 ppm to 0.5% | 10 ppm to 0.1% |
| MeI | 1% to 95% | 10% to 90% | 20% to 80% |
| MA | 0.01% to 40% | 0.1% to 20% | 1% to 10% |
| $H_2O$ | 0% to 10% (e.g., 0.01% to 10%) | 0.02% to 5% | 0.05% to 2% |
| AcOH | 0% to 1% (e.g., 0.001% to 1%) | 5 ppm to 0.5% | 10 ppm to 0.1% |
| HI | 0% to 1% (e.g., 1 ppt to 0.1%) | 100 ppt to 0.01% | 10 ppb to 1 ppm |
| FrOH | 0% to 1% (e.g., 1 ppb to 0.1%) | 10 ppb to 100 ppm | 100 ppb to 10 ppm |
| PrOH | 0% to 1% (e.g., 1 ppb to 0.1%) | 10 ppb to 100 ppm | 100 ppb to 10 ppm |
| DME | 0% to 1% (e.g., 0.1 ppm to 1%) | 1 ppm to 0.1% | 5 ppm to 0.05% |
| $(CH_3)_2C{=}O$ | 0% to 1% (e.g., 0.01 ppm to 1%) | 0.1 ppm to 0.1% | 1 ppm to 0.05% |
| EtOH | 0% to 1% (e.g., 0.01 ppm to 1%) | 0.1 ppm to 0.1% | 1 ppm to 0.05% |
| EA | 0% to 1% (e.g., 0.01 ppm to 1%) | 0.1 ppm to 0.1% | 1 ppm to 0.05% |
| EtI | 0% to 1% (e.g., 0.01 ppm to 1%) | 0.1 ppm to 0.1% | 1 ppm to 0.05% |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

The lower phase in the feed line 111 may typically have a composition approximately identical to or similar to the composition of the lower phase 39 in the decanter S2.

The lower phase in the feed line 112 may typically have a composition approximately identical to or similar to the composition of the composition of the lower phase 39 from the decanter S2. A component proportion in the lower phase in the feed line 112 may be determined by weighted-averaging the corresponding component proportion in the lower phase in the feed line 111 and the component proportion in the condensate in the line 36.

The ratio (mass ratio) of the flow rate of the upper phase to the flow rate of the lower phase, each of which is withdrawn from the decanter S2, may be typically from about 0.1:1 to about 10:1 (e.g., from about 0.3:1 to about 3:1), and preferably from about 0.5:1 to about 2:1 (e.g., from about 0.7:1 to about 1.5:1). For the upper phase, the ratio (mass ratio) of the amount to be returned to the splitter column (3) to the amount to be recycled to the reactor (1) may be typically from about 2:1 to about 1000:1 (e.g., from about 5:1 to about 200:1), and preferably from about 10:1 to about 100:1 (e.g., from about 15:1 to about 50:1).

The first overhead (3A) may be fed to a first aldehyde-removing column (11) for the first aldehyde separation step (11), without condensation and liquid-liquid separation in the decanter S2. Alternatively, it is also acceptable that the first overhead (3A) is subjected to liquid-liquid separation into an upper phase rich in acetaldehyde, and a lower phase rich in methyl iodide, and at least one of the upper phase and the lower phase is fed to at least one of the first aldehyde removing column (11) and the reactor (1). To the reactor (1), a portion of the upper phase is recycled in this embodiment, but the lower phase may be recycled. The upper phase, instead of the lower phase, may be fed to the first aldehyde-removing column (11).

Assume that the first overhead (3A) is cooled successively in condensers having successively lowering cooling temperatures to form condensates. In this case, as compared with a process liquid (condensate) condensed by the first condenser, a condensate formed by a downstream condenser contains acetaldehyde in a higher concentration. Accordingly, a concentrate (condensate) containing acetaldehyde in a higher concentration may be fed to the first aldehyde separation step (11) to separate acetaldehyde from the concentrate.

First Aldehyde Separation Step (11)

A condensate in the line 112 from the decanter S2 in the liquid-liquid separation step (10) is at least a portion 112 of the lower phase 39, which is rich in methyl iodide and contains other components such as methyl acetate. The portion 112 is heated in a heating unit, and held in a hold tank S4 for gas-liquid separation or degassing treatment to give a condensate mixture. The condensate mixture, which is rich in methyl iodide and contains other components such as methyl acetate, is fed from the hold tank S4 via a line 114 to the fifth distillation column (11) for distillation, to form a fifth overhead (11A) rich in acetaldehyde and methyl iodide. Specifically, in the first aldehyde separation step (11) in this embodiment, the lower phase, which has been liquid-liquid separated in the liquid-liquid separation step (10) and fed via the feed lines 112 and 114, is distilled and separated into the fifth overhead (11A) and a bottom stream (11B). The fifth overhead (11A) is withdrawn from the top or an upper part of the fifth distillation column (11) via a withdrawing line (line 115). The bottom stream (11B) is withdrawn from the column via a bottom line 123. The gaseous phase from the hold tank S4, which contains methyl iodide or another component, is sent via a line 113, mixed with the non-condensable gas from the decanter S2 in the liquid-liquid separation step (10), and the mixture is cooled and condensed in a condenser.

The bottom stream (11B) (line 123) contains components such as acetic acid and water. Of the bottom stream (11B), a first portion is recycled to the fifth distillation column (11); and a second portion (or the remainder) is sent via a line 124, mixed with the methyl iodide-rich lower phase from the decanter S2, and recycled to the reactor (1).

The fifth overhead (11A) (line 115), which is rich in acetaldehyde and methyl iodide, is cooled and condensed in a condenser to give a condensate and a non-condensable gas. The condensate is sent via lines 117 and 119 to a hold tank T6 for storage. The non-condensable gas, which contains methyl iodide and other components, is sent via lines 116 and 118, mixed with the non-condensable gas from the decanter S2 in the liquid-liquid separation step (10), and the mixture is cooled and condensed in a condenser. Of the condensate from the hold tank T6, a portion is refluxed via lines 120 and 121 to the fifth distillation column (11); and the remainder is cooled in a condenser in a line 122 and fed via a line 125 to an aqueous extraction-distillation column (12) in the extraction step (12).

The condensate (line 114) from the decanter S4 may have a composition typically as follows.

The condensate (line 114) from the decanter S4 may have a composition approximately identical to or similar to the composition of the lower phase 39 in the decanter S2, or the composition of the mixture in the feed line 112, except the concentrations of components to be contained in the non-condensable gas and the concentration of DME. Accordingly, the following table presents, of the composition of the condensate, the concentrations of components to be contained in the non-condensable gas and the concentration of DME.

TABLE 36

| Average molecular weight: 119.03 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0%10 1% (e.g., 0.1 ppm to 0.1%) | 1 ppm to 0.01% | 2 to 500 ppm |
| CO | 0% to 1% (e.g., 0.1 ppm to 0.1%) | 1 ppm to 0.01% | 1 to 500 ppm |
| $CO_2$ | 0% to 1% (e.g., 0.1 ppm to 0.1%) | 1 ppm to 0.01% | 1 to 500 ppm |
| $CH_4$ | 0% to 1% (e.g., 0.1 ppm to 0.1%) | 1 ppm to 0.01% | 1 to 500 ppm |
| $N_2$ | 0% to 1% (e.g., 0.1 ppm to 1%) | 1 ppm to 0.1% | 2 ppm to 0.1% |
| DME | 0% to 1% (e.g., 0.01 ppm to 0.1%) | 0.05 to 100 ppm | 0.5 to 20 ppm |

The non-condensable gas (line 113) from the decanter S4 may have a composition typically as follows.

TABLE 37

| Average molecular weight: 100.95 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) 0% to 5% | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | (e.g., 1 ppm to 5%) | 10 ppm to 1% | 100 ppm to 0.1% |
| CO | 0.001% to 10% | 0.01% to 5% | 0.1% to 1% |
| $CO_2$ | 0.001% to 20% | 0.01% to 10% | 0.1% to 2% |
| $CH_4$ | 0% to 5% (e.g., 1 ppm to 5%) | 10 ppm to 1% | 100 ppm to 0.1% |
| $N_2$ | 0% to 5% (e.g., 1 ppm to 5%) | 10 ppm to 1% | 100 ppm to 0.1% |
| AD | 0.001% to 10% | 0.01% to 5% | 0.1% to 1% |
| MeOH | 0% to 1% (e.g., 1 ppm to 1%) | 5 ppm to 0.5% | 10 ppm to 0.1% |
| MeI | 1% to 99% | 10% to 95% | 40% to 90% |
| MA | 0.01% to 50% | 0.1% to 20% | 1% to 10% |
| $H_2O$ | 0.001% to 20% | 0.01% to 10% | 0.1% to 5% |
| AcOH | 0% to 2% (e.g., 0.001% to 2%) | 0.005% to 1% | 0.01% to 0.5% |
| HI | 0% to 1% (e.g., 1 ppb to 0.1%) | 10 ppb to 0.01% | 100 ppb to 0.001% |
| FrOH | 0% to 1% (e.g., 1 ppb to 0.1%) | 10 ppb to 0.01% | 100 ppb to 0.001% |
| PrOH | 0% to 1% (e.g., 1 ppb to 0.1%) | 10 ppb to 0.01% | 100 ppb to 0.001% |
| DME | 0% to 1% (e.g., 0.1 ppm to 1%) | 1 ppm to 0.1% | 5 ppm to 0.05% |
| $(CH_3)_2C=O$ | 0% to 1% (e.g., 0.01 ppm to 1%) | 0.1 ppm to 0.1% | 1 ppm to 0.05% |
| EtOH | 0% to 1% (e.g., 0.01 ppm to 1%) | 0.1 ppm to 0.1% | 1 ppm to 0.05% |
| EA | 0% to 1% (e.g., 0.01 ppm to 1%) | 0.1 ppm to 0.1% | 1 ppm to 0.05% |
| EtI | 0% to 1% (e.g., 0.01 ppm to 1%) | 0.1 ppm to 0.1% | 1 ppm to 0.05% |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

The fifth overhead (11A) (line 115) may have a composition typically as follows.

TABLE 38

| Average molecular weight: 71.30 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 0.01 ppm to 1%) | 0.1 ppm to 0.1% | 1 ppm to 0.01% |
| CO | 0% to 3% (e.g., 0.1 ppm to 3%) | 1 ppm to 1% | 10 ppm to 0.1% |
| $CO_2$ | 0% to 3% (e.g., 0.1 ppm to 3%) | 1 ppm to 1% | 10 ppm to 0.1% |
| $CH_4$ | 0% to 1% (e.g., 0.01 ppm to 1%) | 0.1 ppm to 0.1% | 1 ppm to 0.01% |
| $N_2$ | 0% to 1% (e.g., 0.01 ppm to 1%) | 0.1 ppm to 0.1% | 1 ppm to 0.01% |
| AD | 5% to 90% (e.g., 10% to 80%) | 15% to 75% | 20% to 60% |
| MeOH | 0% to 5% (e.g., 0.1 ppm to 5%) | 1 ppm to 1% | 10 ppm to 0.1% |
| MeI | 5% to 95% (e.g., 10% to 90%) | 20% to 85% | 40% to 80% |
| MA | 0.1 ppm to 5% | 1 ppm to 1% | 10 ppm to 0.5% |
| $H_2O$ | 1 ppm to 10% | 10 ppm to 2% | 100 ppm to 1% |
| AcOH | 0% to 1% (e.g., 1 ppb to 1%) | 10 ppb to 0.1% | 100 ppb to 0.01% |
| HI | 0% to 1% (e.g., 1 ppb to 0.1%) | 10 ppb to 0.01% | 100 ppb to 0.001% |
| FrOH | 0% to 1% (e.g., 1 ppb to 0.1%) | 10 ppb to 0.01% | 100 ppb to 0.001% |
| PrOH | 0% to 1% (e.g., 1 ppb to 0.1%) | 10 ppb to 0.01% | 100 ppb to 0.001% |
| DME | 0% to 1% (e.g., 0.1 ppm to 1%) | 1 ppm to 0.1% | 5 ppm to 0.05% |
| $(CH_3)_2C=O$ | 0% to 1% (e.g., 0.01 ppm to 1%) | 0.1 ppm to 0.1% | 1 ppm to 0.05% |
| EtOH | 0% to 1% (e.g., 0.01 ppm to 1%) | 0.1 ppm to 0.1% | 1 ppm to 0.05% |
| EA | 0% to 1% (e.g., 0.01 ppm to 1%) | 0.1 ppm to 0.1% | 1 ppm to 0.05% |
| EtI | 0% to 1% (e.g., 0.01 ppm to 1%) | 0.1 ppm to 0.1% | 1 ppm to 0.05% |
| Li | 0% to 0.1% (e.g., 0.01 ppt to 100 ppb) | 0.1 ppt to 10 ppb | 1 ppt to 1 ppb |

TABLE 38-continued

| Average molecular weight: 71.30 | Range | Preferred range | More preferred range |
|---|---|---|---|
| Rh | 0% to 0.1% (e.g., 0.01 ppt to 100 ppb) | 0.1 ppt to 10 ppb | 1 ppt to 1 ppb |

The condensates (lines 120, 121, and 122) of the fifth overhead (line 115) from the condensers may each have a composition typically as follows.

The condensates (lines 120, 121, and 122) may each have a composition approximately identical to or similar to the composition of the fifth overhead (11A) (line 115), except the concentrations of components to be contained in the non-condensable gas. Thus, the following table presents, of the composition of the condensates, the concentrations of components to be contained in the non-condensable gas.

TABLE 39

| Average molecular weight: 71.33 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% 10 1% (e.g., 1 ppb to 0.1%) | 10 ppb to 0.01% | 100 ppb to 0.001% |
| CO | 0% to 1% (e.g., 0.01 ppm to 1%) | 0.1 ppm to 0.1% | 1 ppm to 0.01% |
| $CO_2$ | 0% to 2% (e.g., 0.1 ppm to 2%) | 1 ppm to 1% | 10 ppm to 0.5% |
| $CH_4$ | 0% to 1% (e.g., 0.01 ppm to 1%) | 0.1 ppm to 0.1% | 1 ppm to 0.01% |
| $N_2$ | 0% to 1% (e.g., 0.01 ppm to 1%) | 0.1 ppm to 0.1% | 1 ppm to 0.01% |

The non-condensable gas (line 118), which has not been condensed by the condenser, derived from the fifth overhead (line 115) may have a composition typically as follows.

As described above, purging of a distillation column with an inert gas (such as nitrogen gas or carbon monoxide gas) may be performed so as to control the pressure of the distillation column and to protect instruments such as a level gauge, a pressure gauge, and a thermometer from a condensable gas. The introduction of such a component causes significant variation of the gas composition of the non-condensable gas in the lines 115, 116, and 118, and causes significant variation of the concentrations of other components, due to dilution with the introduced inert gas.

TABLE 40

| Average molecular weight: 39.25 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 0.1 ppm to 1%) | 1 ppm to 0.1% | 10 ppm to 0.01% |
| CO | 0.01% to 20% | 0.1% to 15% | 0.5% to 10% |
| $CO_2$ | 0.01% to 70% | 0.1% to 60% | 0.5% to 50% |
| $CH_4$ | 0% to 1% (e.g., 0.1 ppm to 1%) | 1 ppm to 0.1% | 10 ppm to 0.01% |
| $N_2$ | 10 ppm to 70% | 100 ppm to 50% | 0.1% to 40% |
| AD | 1 ppm to 30% | 10 ppm to 25% | 100 ppm to 20% |
| MeOH | 0% to 1% (e.g., 0.1 ppm to 1%) | 1 ppm to 0.5% | 10 ppm to 0.1% |
| MeI | 1% to 50% | 2% to 40% | 5% to 25% |
| MA | 0% to 10% (e.g., 5 ppm to 1%) | 10 ppm to 0.5% | 25 ppm to 0.1% |
| $H_2O$ | 0% to 10% (e.g., 10 ppm to 5%) | 50 ppm to 1% | 50 ppm to 0.1% |
| AcOH | 0% to 1% (e.g., 1 ppm to 1%) | 10 ppm to 0.3% | 100 ppm to 0.1% |
| HI | 0% to 1% (e.g., 1 ppb to 0.1%) | 10 ppb to 0.01% | 100 ppb to 0.001% |
| FrOH | 0% to 1% (e.g., 1 ppb to 0.1%) | 10 ppb to 0.01% | 100 ppb to 0.001% |
| PrOH | 0% to 1% (e.g., 1 ppb to 0.1%) | 10 ppb to 0.01% | 100 ppb to 0.001% |

TABLE 40-continued

| Average molecular weight: 39.25 | Range | Preferred range | More preferred range |
|---|---|---|---|
| DME | 0% to 2% (e.g., 0.1 ppm to 1%) | 1 ppm to 1% | 10 ppm to 0.1% |
| $(CH_3)_2C=O$ | 0% to 1% (e.g., 0.01 ppm to 1%) | 0.1 ppm to 0.1% | 1 ppm to 0.05% |
| EtOH | 0% to 1% (e.g., 0.01 ppm to 1%) | 0.1 ppm to 0.1% | 1 ppm to 0.05% |
| EA | 0% to 1% (e.g., 0.01 ppm to 1%) | 0.1 ppm to 0.1% | 1 ppm to 0.05% |
| EtI | 0% to 1% (e.g., 0.01 ppm to 1%) | 0.1 ppm to 0.1% | 1 ppm to 0.05% |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

The bottom stream (11B) (lines 123 and 124) from the fifth distillation column (11) may have a composition typically as follows.

TABLE 41

| Average molecular weight: 119.33 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppt to 0.1%) | 10 ppt to 0.01% | 100 ppt to 0.001% |
| CO | 0% to 1% (e.g., 1 ppt to 0.1%) | 10 ppt to 0.01% | 100 ppt to 0.001% |
| $CO_2$ | 0% to 1% (e.g., 1 ppt to 0.1%) | 10 ppt to 0.01% | 100 ppt to 0.001% |
| $CH_4$ | 0% to 1% (e.g., 1 ppt to 0.1%) | 10 ppt to 0.01% | 100 ppt to 0.001% |
| $N_2$ | 0% to 1% (e.g., 1 ppt to 0.1%) | 10 ppt to 0.01% | 100 ppt to 0.001% |
| AD | 0% to 1% (e.g., 1 ppm to 0.5%) | 10 ppm to 0.2% | 100 to 700 ppm |
| MeOH | 0% to 1% (e.g., 0.1 ppm to 0.5%) | 1 ppm to 0.1% | 10 ppm to 0.01% |
| MeI | 1% to 99% (e.g., 10% to 95%) | 30% to 98% (e.g., 50% to 95%) | 70% to 90% |
| MA | 1% to 40% | 5% to 30% | 7% to 20% |
| $H_2O$ | 0.01% to 30% | 0.1% to 10% | 0.5% to 5% |
| AcOH | 0.01% to 10% | 0.1% to 5% | 0.5% to 3% |
| HI | 0% to 1% (e.g., 0.01 ppm to 0.1%) | 0.05 ppm to 0.2% (e.g., 0.1% to 500 ppm) | 0.5 ppm to 0.1% (e.g., 1 to 100 ppm) |
| FrOH | 0% to 1% (e.g., 1 ppb to 100 ppm) | 10 ppb to 10 ppm | 100 ppb to 5 ppm |
| PrOH | 0% to 1% (e.g., 1 ppb to 100 ppm) | 10 ppb to 10 ppm | 100 ppb to 5 ppm |
| DME | 0% to 1% (e.g., 1 ppb to 100 ppm) | 5 ppb to 0.5% (e.g., 10 ppb to 10 ppm) | 50 ppb to 0.1% (e.g., 100 ppb to 5 ppm) |
| $(CH_3)_2C=O$ | 0% to 1% (e.g., 1 ppb to 100 ppm) | 10 ppb to 10 ppm | 100 ppb to 5 ppm |
| EtOH | 0% to 1% (e.g., 1 ppb to 100 ppm) | 10 ppb to 10 ppm | 100 ppb to 5 ppm |
| EA | 0% to 1% (e.g., 1 ppb to 100 ppm) | 10 ppb to 10 ppm | 100 ppb to 5 ppm |
| EtI | 0% to 1% (e.g., 1 ppb to 100 ppm) | 10 ppb to 10 ppm | 100 ppb to 5 ppm |
| Li | 0% to 0.1% (e.g., 0.01 ppt to 100 ppb) | 1 ppt to 10 ppb | 10 ppt to 1 ppb |
| Rh | 0% to 0.1% (e.g., 0.01 ppt to 100 ppb) | 1 ppt to 10 ppb | 10 ppt to 1 ppb |

The first aldehyde separation step (11) has only to perform distillation of the condensate, which has been condensed in the liquid-liquid separation step (10), to thereby form the fifth overhead (11A) rich in acetaldehyde and methyl iodide. Thus, the distillation may be performed on the upper phase of the condensate, or on the lower phase, or on the condensate mixture of the upper phase and the lower phase. The fifth distillation column (11) for use herein may be selected typically from plate columns and packed columns.

Extraction Step (12)

In the aqueous extraction-distillation column (sixth distillation column) (12) in the extraction step (12), extraction of acetaldehyde from the fifth overhead (11A) (a condensate cooled in a condenser) is performed to form an extract and a raffinate, where the extract is rich in acetaldehyde, and the raffinate is rich in methyl iodide. Specifically, the condensate and an extractant (water) are fed respectively via a feed line 125 and a feed line 126 to the aqueous extraction-distillation column (12), where the feed line 126 leads to a lower part of the column (12). In the aqueous extraction-distillation column (12), the fifth overhead (11A) is separated into an aqueous extract (12A) and a raffinate (12B). The aqueous extract (extract of acetaldehyde) (12A) is withdrawn from the top or an upper part of the aqueous extraction-distillation column (12) via a withdrawing line 131. The raffinate (12B), which is rich in methyl iodide, is withdrawn from a bottom line 132. The raffinate (12B) (line 132) is discarded as a liquid waste, or recycled to the reactor (1). The aqueous extract (12A) (line 131) is further fed to the second aldehyde separation step (13).

The extractant (water) fed from the feed line 126 may have a composition typically as follows.

TABLE 42

| Average molecular weight: 18.02 | Range | Preferred range | More preferred range |
|---|---|---|---|
| O$_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| H$_2$ | 0% to 1% (e.g., 1 ppt to 1%) | 10 ppt to 0.1% | 100 ppt to 0.01% |
| CO | 0% to 1% (e.g., 1 ppt to 1%) | 10 ppt to 0.1% | 100 ppt to 0.01% |
| CO$_2$ | 0% to 1% (e.g., 1 ppt to 1%) | 10 ppt to 0.1% | 100 ppt to 0.01% |
| CH$_4$ | 0% to 1% (e.g., 1 ppt to 1%) | 10 ppt to 0.1% | 100 ppt to 0.01% |
| N$_2$ | 0% to 1% (e.g., 1 ppt to 1%) | 10 ppt to 0.1% | 100 ppt to 0.01% |
| AD | 0% to 0.01% (e.g., 0.001 to 100 ppm) | 0.01 to 50 ppm | 0.1 to 10 ppm |
| MeOH | 0% to 0.01% (e.g., 0.001 to 100 ppm) | 0.01 to 50 ppm | 0.1 to 10 ppm |
| MeI | 0% to 0.01% (e.g., 0.001 to 100 ppm) | 0.01 to 50 ppm | 0.1 to 10 ppm |
| MA | 0% to 0.01% (e.g., 0.001 to 100 ppm) | 0.01 to 50 ppm | 0.1 to 10 ppm |
| H$_2$O | 99% to 100% | 99.5% to 99.999% | 99.9% to 99.99% |
| AcOH | 0% to 1% (e.g., 0% to 0.01%) | 0.01 to 50 ppm | 0.1 to 10 ppm |
| HI | 0% to 0.01% (e.g., 0.001 to 100 ppm) | 0.01 to 50 ppm | 0.1 to 10 ppm |
| FrOH | 0% to 0.01% (e.g., 0.001 to 100 ppm) | 0.01 to 50 ppm | 0.1 to 10 ppm |
| PrOH | 0% to 0.01% (e.g., 0.001 to 100 ppm) | 0.01 to 50 ppm | 0.1 to 10 ppm |
| DME | 0% to 0.01% (e.g., 0.001 to 100 ppm) | 0.01 to 50 ppm | 0.1 to 10 ppm |
| (CH$_3$)$_2$C=O | 0% to 0.01% (e.g., 0.001 to 100 ppm) | 0.01 to 50 ppm | 0.1 to 10 ppm |
| EtOH | 0% to 0.01% (e.g., 0.001 to 100 ppm) | 0.01 to 50 ppm | 0.1 to 10 ppm |
| EA | 0% to 0.01% (e.g., 0.001 to 100 ppm) | 0.01 to 50 ppm | 0.1 to 10 ppm |
| EtI | 0% to 0.01% (e.g., 0.001 to 100 ppm) | 0.01 to 50 ppm | 0.1 to 10 ppm |
| Li | 0% to 0.1% (e.g., 0 to 1 ppm) | 1 ppt to 10 ppb | 10 ppt to 1 ppb |
| Rh | 0% to 0.1% (e.g., 0 to 1 ppm) | 1 ppt to 10 ppb | 10 ppt to 1 ppb |

The aqueous extract (12A) (line 131) may have a composition typically as follows.

TABLE 43

| Average molecular weight: 21.43 | Range | Preferred range | More preferred range |
|---|---|---|---|
| O$_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| H$_2$ | 0.1% or less (e.g., 1 ppt to 0.1%) | 10 ppt to 0.01% | 100 ppt to 0.001% |
| CO | 0% to 1% (e.g., 1 ppt to 0.1%) | 10 ppt to 0.01% | 100 ppt to 0.001% |
| CO$_2$ | 0% to 5% (e.g., 1 ppt to 5%) | 10 ppt to 3% | 100 ppt to 1% |
| CH$_4$ | 0% to 1% (e.g., 1 ppt to 0.1%) | 10 ppt to 0.01% | 100 ppt to 0.001% |
| N$_2$ | 0% to 1% (e.g., 1 ppt to 0.5%) | 10 ppt to 0.1% | 100 ppt to 0.01% |
| AD | 1% to 50% | 3% to 40% | 5% to 30% |
| MeOH | 0% to 1% (e.g., 0.1 ppm to 0.5%) | 1 ppm to 0.1% | 10 ppm to 0.01% |
| MeI | 0% to 25% (e.g., 0.1% to 20%) | 0.5% to 20% | 1% to 15% |
| MA | 0% to 2% (e.g., 10 ppb to 1%) | 100 ppb to 1% | 1 ppm to 0.5% |
| H$_2$O | 10% to 98% | 50% to 95% | 60% to 90% |
| AcOH | 0% to 5% (e.g., 10 ppb to 1%) | 100 ppb to 3% | 1 ppm to 1% |
| HI | 0% to 1% (e.g., 0.01 ppm to 0.1%) | 0.1 to 500 ppm | 1 to 100 ppm |
| FrOH | 0% to 1% (e.g., 0.1 ppb to 100 ppm) | 1 ppb to 10 ppm | 10 ppb to 1 ppm |
| PrOH | 0% to 1% (e.g., 0.1 ppb to 100 ppm) | 1 ppb to 10 ppm | 10 ppb to 1 ppm |
| DME | 0% to 1% (e.g., 10 ppb to 1%) | 100 ppb to 0.2% | 1 to 500 ppm |
| (CH$_3$)$_2$C=O | 0% to 1% (e.g., 1 ppb to 100 ppm) | 10 ppb to 10 ppm | 100 ppb to 5 ppm |
| EtOH | 0% to 1% (e.g., 1 ppb to 100 ppm) | 10 ppb to 10 ppm | 100 ppb to 5 ppm |
| EA | 0% to 1% (e.g., 1 ppb to 100 ppm) | 10 ppb to 10 ppm | 100 ppb to 5 ppm |
| EtI | 0% to 1% (e.g., 1 ppb to 100 ppm) | 10 ppb to 10 ppm | 100 ppb to 5 ppm |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

The raffinate (12B) (line 132) may have a composition typically as follows.

TABLE 44

| Average molecular weight: 115.86 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppt to 0.1%) | 10 ppt to 0.01% | 100 ppt to 0.001% |
| CO | 0% to 1% (e.g., 1 ppt to 0.1%) | 10 ppt to 0.01% | 100 ppt to 0.001% |
| $CO_2$ | 0% to 5% (e.g., 1 ppt to 5%) | 10 ppt to 2% | 100 ppt to 1% |
| $CH_4$ | 0% to 1% (e.g., 1 ppt to 0.1%) | 10 ppt to 0.01% | 100 ppt to 0.001% |
| $N_2$ | 0% to 1% (e.g., 1 ppt to 0.5%) | 10 ppt to 0.1% | 100 ppt to 0.01% |
| AD | 0.1% to 30% | 1% to 20% | 5% to 15% |
| MeOH | 0% to 1% (e.g., 0.01 ppm to 1%) | 0.1 ppm to 0.1% | 1 to 100 ppm |
| MeI | 80% to 100% | 90% to 99.999% | 99% to 99.99% |
| MA | 0.1 ppm to 2% | 1 ppm to 1% | 10 ppm to 0.5% |
| $H_2O$ | 10 ppm to 2% | 100 ppm to 1% | 500 ppm to 0.5% |
| AcOH | 0% to 1% (e.g., 10 ppb to 1%) | 100 ppb to 0.5% | 1 ppm to 0.1% |
| HI | 0% to 1% (e.g., 1 ppb to 0.1%) | 10 ppb to 500 ppm | 100 ppb to 100 ppm |
| FrOH | 0% to 1% (e.g., 0.1 ppb to 100 ppm) | 1 ppb to 10 ppm | 10 ppb to 1 ppm |
| PrOH | 0% to 1% (e.g., 0.1 ppb to 100 ppm) | 1 ppb to 10 ppm | 10 ppb to 1 ppm |
| DME | 0% to 1% (e.g., 10 ppb to 1%) | 100 ppb to 0.2% | 1 to 500 ppm |
| $(CH_3)_2C=O$ | 0% to 1% (e.g., 1 ppb to 100 ppm) | 10 ppb to 10 ppm | 100 ppb to 5 ppm |
| EtOH | 0% to 1% (e.g., 1 ppb to 100 ppm) | 10 ppb to 10 ppm | 100 ppb to 5 ppm |
| EA | 0% to 1% (e.g., 1 ppb to 100 ppm) | 10 ppb to 10 ppm | 100 ppb to 5 ppm |
| EtI | 0% to 1% (e.g., 1 ppb to 100 ppm) | 10 ppb to 10 ppm | 100 ppb to 5 ppm |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

For the aqueous extraction-distillation, it is acceptable that the condensate mixture is fed to the aqueous extraction-distillation column, and the extractant (water) is fed to an upper part of the aqueous extraction-distillation column, to give an raffinate and an aqueous extract. The raffinate, which is rich in methyl iodide, is withdrawn from the top or an upper part of the column. The aqueous extract (extract of acetaldehyde) is withdrawn from the bottom. The aqueous extraction-distillation column (12) for use herein may be selected typically from plate columns and packed columns.

The extraction step (12) may employ an extraction unit (extractor) instead of the aqueous extraction-distillation column (12). The extraction unit may include an extractor or extractors. Non-limiting examples of the extractor for use herein include the combination of a mixer with a settler, the combination of a handheld immersion blender with a decanter, rotated disk contactors (RDCs), Karr columns, spray columns, packed columns, perforated-plate columns, baffle columns, and pulsed columns. The extractor (extraction column) may be a single-stage extracting device, or may include two or more of the single-stage extracting device arranged in a cascade manner, where the single-stage extracting device is capable of mixing an object with water, extracting the object from the mixture, and thereby separating the mixture into liquids. Alternatively, two or more extractors may constitute a multistage extracting device for sequential extraction, where each extractor has a theoretical number of plates of 1. Further alternatively, extractors arranged in one device may constitute a multistage extracting device. The extractor may also be a single extracting device that has a theoretical number of plates equivalent to such a multistage extracting device (theoretical number of plates corresponding to multistage extraction). The extraction may be performed according to either a batch system or a continuous system, as either co-current extraction or countercurrent extraction.

At least a portion of the raffinate (12B) may be recycled to the reactor (1). At least a portion of the aqueous extract may be fed to the succeeding second aldehyde separation step (13).

Second Aldehyde Separation Step (13)

In a seventh distillation column (13) in the second aldehyde separation step (13) (seventh distillation step), the aqueous extract (12A) (line 131), which is rich in acetaldehyde, is distilled and separated into a sixth overhead (13A) and a bottom stream (13B), as in the first aldehyde separation step (11). The sixth overhead (13A) is withdrawn from the top or an upper part of the column via a withdrawing line 141. The bottom stream (13B) is withdrawn via a bottom line 146.

The bottom stream (13B) (line 146) contains components such as water. Of the bottom stream (13B), a first portion is recycled to the seventh distillation column (13); and a second portion (or the remainder) is fed via the line 146 to a incinerator for incineration.

The sixth overhead (13A), which is rich in acetaldehyde, is cooled and condensed in a condenser in the withdrawing line 141 to form a condensate and a non-condensable gas, and the condensate is stored in a hold tank T7. Of the condensate, a portion is refluxed via a reflux line 143 to the seventh distillation column (13); and the remainder is sent via a line 144 to an incineration unit for incineration. The non-condensable gas, which has not been condensed in the condenser, is mixed, through a line 145, with the non-condensable gas from the decanter S2 in the liquid-liquid separation step (10), and the mixture is cooled and condensed in a condenser.

The sixth overhead (13A) (line 141) may have a composition typically as follows.

TABLE 45

| Average molecular weight: 42.08 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 1 ppt to 0.1%) | 10 ppt to 0.01% | 100 ppt to 0.001% |
| CO | 0% to 1% (e.g., 1 ppt to 0.1%) | 10 ppt to 0.01% | 100 ppt to 0.001% |
| $CO_2$ | 0% to 1% (e.g., 1 ppt to 1%) | 10 ppt to 0.5% | 100 ppt to 0.05% |
| $CH_4$ | 0% to 1% (e.g., 1 ppt to 0.1%) | 10 ppt to 0.01% | 100 ppt to 0.001% |
| $N_2$ | 0% to 5% (e.g., 1 ppt to 5%) | 10 ppt to 1% | 100 ppt to 0.1% |
| AD | 50% to 99% | 70% to 95% | 80% to 90% |
| MeOH | 0% to 5% (e.g., 0.1 ppm to 5%) | 1 ppm to 1% | 10 ppm to 0.1% |
| MeI | 0.1% to 30% | 0.5% to 20% | 1% to 10% |
| MA | 0.1 ppm to 3% | 1 ppm to 1% | 10 ppm to 0.5% |
| $H_2O$ | 0.1% to 30% | 1% to 20% | 3% to 10% |
| AcOH | 0% to 1% (e.g., 0.1 ppb to 0.1%) | 1 ppb to 0.01% | 10 ppb to 0.001% |
| HI | 0% to 1% (e.g., 1 ppb to 0.5%) | 10 ppb to 0.1% | 100 ppb to 200 ppm |
| FrOH | 0% to 1% (e.g., 0.1 ppb to 100 ppm) | 1 ppb to 10 ppm | 10 ppb to 1 ppm |
| PrOH | 0% to 1% (e.g., 0.1 ppb to 100 ppm) | 1 ppb to 10 ppm | 10 ppb to 1 ppm |
| DME | 0% to 1% (e.g., 10 ppb to 1%) | 100 ppb to 0.2% | 1 to 500 ppm |
| $(CH_3)_2C=O$ | 0% to 1% (e.g., 1 ppb to 100 ppm) | 10 ppb to 10 ppm | 100 ppb to 5 ppm |
| EtOH | 0% to 1% (e.g., 1 ppb to 100 ppm) | 10 ppb to 10 ppm | 100 ppb to 5 ppm |
| EA | 0% to 1% (e.g., 1 ppb to 100 ppm) | 10 ppb to 10 ppm | 100 ppb to 5 ppm |
| EtI | 0% to 1% (e.g., 1 ppb to 100 ppm) | 10 ppb to 10 ppm | 100 ppb to 5 ppm |
| Li | 0% to 0.1% (e.g., 0.01 ppt to 100 ppb) | 0.1 ppt to 10 ppb | 1 ppt to 1 ppb |
| Rh | 0% to 0.1% (e.g., 0.01 ppt to 100 ppb) | 0.1 ppt to 10 ppb | 1 ppt to 1 ppb |

The condensates 143 and 144 from the condenser may each have a composition approximately identical to or similar to the composition of the sixth overhead (13A) (line 141), except the concentrations of components to be contained in the non-condensable gas. Accordingly, the following table presents, of the composition of the condensates 143 and 144, the concentrations of components to be contained in the non-condensable gas from the condenser.

TABLE 46

| Average molecular weight: 42.08 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 1 ppt to 0.1%) | 10 ppt to 0.01% | 100 ppt to 0.001% |
| CO | 0% to 1% (e.g., 1 ppt to 0.01%) | 10 ppt to 0.001% | 100 ppt to 0.0001% |
| $CO_2$ | 0% to 1% (e.g., 1 ppt to 0.1%) | 10 ppt to 0.05% | 100 ppt to 0.005% |
| $CH_4$ | 0% to 1% (e.g., 1 ppt to 0.01%) | 10 ppt to 0.001% | 100 ppt to 0.0001% |
| $N_2$ | 0% to 1% (e.g., 1 ppt to 0.5%) | 10 ppt to 0.1% | 100 ppt to 0.01% |

The non-condensable gas 145 from the condenser may have a composition typically as follows.

The composition of the non-condensable gas 145 significantly varies depending on the amount of the purge inert gas, as described above.

TABLE 47

| Average molecular weight: 37.56 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 1% (e.g., 0.1 ppm to 1%) | 1 ppm to 0.1% | 10 ppm to 0.01% |
| CO | 0.01% to 60% | 0.1% to 50% | 0.5% to 40% |
| $CO_2$ | 0.01% to 60% | 0.1% to 50% | 0.5% to 40% |
| $CH_4$ | 0% to 3% (e.g., 0.1 ppm to 2%) | 1 ppm to 1% | 10 ppm to 0.5% |
| $N_2$ | 0% to 3% (e.g., 10 ppm to 2%) | 50 ppm to 1% | 100 ppm to 0.5% |
| AD | 0.1% to 90% | 1% to 80% | 5% to 70% |
| MeOH | 0% to 1% (e.g., 0.1 ppm to 1%) | 1 ppm to 0.5% | 10 ppm to 0.1% |
| MeI | 100 ppm to 50% | 0.1% to 20% | 0.5% to 5% |
| MA | 0.001% to 10% | 0.01% to 5% | 0.1% to 2% |
| $H_2O$ | 0% to 1% (e.g., 0.0001% to 2%) | 0.001% to 1% | 0.01% to 0.1% |
| AcOH | 0% to 1% (e.g., 0.0001% to 2%) | 0.001% to 1% | 0.01% to 0.1% |
| HI | 0% to 1% (e.g., 1 ppb to 0.1%) | 10 ppb to 0.01% | 100 ppb to 0.001% |
| FrOH | 0% to 1% (e.g., 1 ppb to 0.1%) | 10 ppb to 0.01% | 100 ppb to 0.001% |
| PrOH | 0% to 1% (e.g., 1 ppb to 0.1%) | 10 ppb to 0.01% | 100 ppb to 0.001% |
| DME | 0% to 1% (e.g., 0.1 ppm to 10%) | 1 ppm to 2% | 10 ppm to 1% |
| $(CH_3)_2C{=}O$ | 0% to 1% (e.g., 0.01 ppm to 1%) | 0.1 ppm to 0.1% | 1 ppm to 0.05% |
| EtOH | 0% to 1% (e.g., 0.01 ppm to 1%) | 0.1 ppm to 0.1% | 1 ppm to 0.05% |
| EA | 0% to 1% (e.g., 0.01 ppm to 1%) | 0.1 ppm to 0.1% | 1 ppm to 0.05% |
| EtI | 0% to 1% (e.g., 0.01 ppm to 1%) | 0.1 ppm to 0.1% | 1 ppm to 0.05% |
| Li | 0% to 0.1% (e.g., 0.1 ppt to 100 ppb) | 1 ppt to 10 ppb | 10 ppt to 1 ppb |
| Rh | 0% to 0.1% (e.g., 0.1 ppt to 100 ppb) | 1 ppt to 10 ppb | 10 ppt to 1 ppb |

The bottom stream (13B) (line 146) may have a composition typically as follows.

TABLE 48

| Average molecular weight: 18.02 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppt to 0.1%) | 10 ppt to 0.01% | 100 ppt to 0.001% |
| CO | 0% to 1% (e.g., 1 ppt to 0.1%) | 10 ppt to 0.01% | 100 ppt to 0.001% |
| $CO_2$ | 0% to 1% (e.g., 1 ppt to 0.1%) | 10 ppt to 0.01% | 100 ppt to 0.001% |
| $CH_4$ | 0% to 1% (e.g., 1 ppt to 0.1%) | 10 ppt to 0.01% | 100 ppt to 0.001% |
| $N_2$ | 0% to 1% (e.g., 1 ppt to 0.1%) | 10 ppt to 0.01% | 100 ppt to 0.001% |
| AD | 0% to 1% (e.g., 1 ppm to 0.5%) | 10 ppm to 0.2% | 100 to 700 ppm |
| MeOH | 0% to 1% (e.g., 0.1 ppm to 0.5%) | 1 ppm to 0.1% | 10 ppm to 0.01% |
| MeI | 0% to 1% (e.g., 0.1 ppm to 0.5%) | 1 ppm to 0.1% | 10 ppm to 0.01% |
| MA | 0% to 1% (e.g., 0.1 ppm to 0.5%) | 1 ppm to 0.1% | 10 ppm to 0.01% |
| $H_2O$ | 90% to 100% | 98% to 99.999% | 99% to 99.99% |
| AcOH | 0% to 1% (e.g., 0.1 ppm to 0.5%) | 1 ppm to 0.1% | 10 ppm to 0.01% |
| HI | 0% to 1% (e.g., 0.01 ppm to 0.1%) | 0.1 to 500 ppm | 1 to 100 ppm |
| FrOH | 0% to 1% (e.g., 1 ppb to 100 ppm) | 10 ppb to 10 ppm | 100 ppb to 5 ppm |
| PrOH | 0% to 1% (e.g., 1 ppb to 100 ppm) | 10 ppb to 10 ppm | 100 ppb to 5 ppm |
| DME | 0% to 1% (e.g., 1 ppb to 100 ppm) | 10 ppb to 10 ppm | 100 ppb to 5 ppm |
| $(CH_3)_2C{=}O$ | 0% to 1% (e.g., 1 ppb to 100 ppm) | 10 ppb to 10 ppm | 100 ppb to 5 ppm |
| EtOH | 0% to 1% (e.g., 1 ppb to 100 ppm) | 10 ppb to 10 ppm | 100 ppb to 5 ppm |
| EA | 0% to 1% (e.g., 1 ppb to 100 ppm) | 10 ppb to 10 ppm | 100 ppb to 5 ppm |
| EtI | 0% to 1% (e.g., 1 ppb to 100 ppm) | 10 ppb to 10 ppm | 100 ppb to 5 ppm |
| Li | 0% to 0.1% (e.g., 0.01 ppt to 100 ppb) | 1 ppt to 10 ppb | 10 ppt to 1 ppb |
| Rh | 0% to 0.1% (e.g., 0.01 ppt to 100 ppb) | 1 ppt to 10 ppb | 10 ppt to 1 ppb |

In the second aldehyde separation step (13), at least a portion of the raffinate (12B) (line 132), which is rich in methyl iodide, may be distilled instead of the at least portion of the aqueous extract (12A) (line 131); or the at least portion of the aqueous extract (12A) (line 131) may be distilled in combination with at least a portion of the raffinate (12B) (line 132), to form the overhead (13A) containing acetaldehyde. The seventh distillation column (13) for use herein may be selected typically from plate columns and packed columns.

Alkane Separation Step (14)

TABLE 49

| Average molecular weight: 119.79 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 0.1 ppm to 1%) | 1 ppm to 0.1% | 2 ppm to 0.1% |
| CO | 0% to 1% (e.g., 0.1 ppm to 1%) | 1 ppm to 0.1% | 10 ppm to 0.05% |
| $CO_2$ | 0% to 1% (e.g., 0.1 ppm to 1%) | 1 ppm to 0.1% | 10 ppm to 0.05% |
| $CH_4$ | 0% to 1% (e.g., 0.1 ppm to 1%) | 1 ppm to 0.1% | 2 ppm to 0.1% |
| $N_2$ | 0 % to 1% (e.g., 0.1 ppm to 1%) | 1 ppm to 0.1% | 2 ppm to 0.1% |
| AD | 0% to 2% (e.g., 0.01% to 2%) | 0.05% to 1% | 0.08% to 0.5% |
| MeOH | 0% to 2% (e.g., 1 ppm to 2%) | 10 ppm to 1% | 100 ppm to 0.3% |
| MeI | 0% to 1% (e.g., 0.1 ppm to 5%) | 1 ppm to 1% | 10 ppm to 0.1% |
| Alkanes ($C_4$ to $C_{20}$) | 1% to 99% | 10% to 80% | 20% to 70% |
| MA | 1% to 40% | 4% to 30% | 7% to 20% |
| $H_2O$ | 0.01% to 20% | 0.1% to 10% | 0.5% to 3% |
| AcOH | 0.1% to 30% | 0.3% to 20% | 0.5% to 15% |
| HI | 0% to 1% (e.g., 0.01 ppm to 0.1%) | 0.1 to 500 ppm | 1 to 100 ppm |
| FrOH | 0% to 1% (e.g., 0.1 ppm to 0.1%) | 1 to 100 ppm | 3 to 50 ppm |
| PrOH | 0% to 1% (e.g., 0.1 ppm to 0.1%) | 1 to 100 ppm | 3 to 30 ppm |
| DME | 0% to 1% (e.g., 1 ppm to 1%) | 10 ppm to 0.5% | 100 ppm to 0.1% |
| $(CH_3)_2C=O$ | 0% to 1% (e.g., 1 ppm to 0.5%) | 10 ppm to 0.2% | 50 ppm to 0.1% |
| EtOH | 0% to 1% (e.g., 1 ppm to 0.5%) | 10 ppm to 0.2% | 50 ppm to 0.1% |
| EA | 0% to 1% (e.g., 1 ppm to 0.5%) | 10 ppm to 0.2% | 50 ppm to 0.1% |
| EtI | 0% to 1% (e.g., 1 ppm to 0.5%) | 10 ppm to 0.2% | 50 ppm to 0.1% |
| Li | 0% to 1% (e.g., 0.01 ppt to 0.1 ppm) | 0.1 ppt to 0.01 ppm | 1 ppt to 0.001 ppm |
| Rh | 0% to 1% (e.g., 0.01 ppt to 0.1 ppm) | 0.1 ppt to 0.01 ppm | 1 ppt to 0.001 ppm |

In the alkane separation step (14), an alkane or alkanes are separated from at least one of the portion 41 of the upper phase and the portion 40 of the lower phase in an alkane-removing column (eighth distillation column) (14), where the upper and lower phases have been separated as liquids in the liquid-liquid separation step (10). Specifically, in this embodiment, the portion 40 of the lower phase is distilled and is separated into a seventh overhead (14A) and a bottom stream (14B) in the alkane separation step (14). The seventh overhead (14A) is withdrawn from the top or an upper part of the alkane-removing column (14) via a withdrawing line 151. The bottom stream (14B) is withdrawn from the column bottom via a bottom line 152.

Of the bottom stream (14B), which contains alkanes, a portion is heated and recycled to the alkane-removing column (14); and the remainder is fed to an incinerator unit for incineration.

The seventh overhead (14A), which contains acetaldehyde and methyl iodide, is cooled and condensed in a condenser in the withdrawing line 151 to give a condensate and a non-condensable gas, and the condensate is then stored in a tank T8. Of the condensate, a portion is refluxed to the alkane-removing column (14); and the remainder is recycled to the reactor (1). The non-condensable gas is mixed, through the line 113, with the non-condensable gas from the decanter S2 in the liquid-liquid separation step (10), and the mixture is cooled and condensed in a condenser.

The seventh overhead (14A) (line 151) may typically have a composition approximately identical or similar to the composition of the lower phase 39 from the decanter S2.

The bottom stream (14B) (line 152) may have a composition typically as follows.

The alkane-removing column (14) for use herein may be selected typically from plate columns and packed columns.

The separation section (9) often includes, among the steps (10) to (14), the liquid-liquid separation step (10), the first aldehyde separation step (11), the extraction step (12), and the second aldehyde separation step (13).

Offgas Treatment Section (15)

An offgas resulting from the process contains useful components such as carbon monoxide and methyl iodide. Accordingly, the method preferably includes the offgas treatment section (15) for subjecting the offgas to an absorbing treatment by an absorbing solvent to recover such useful components. The offgas treatment section (15) may typically include (16) a high-pressure absorbing step or first absorbing step, (17) a low-pressure absorbing step or second absorbing step, and (18) a stripping step. The high-pressure absorbing step or first absorbing step (16) is the step of allowing the absorbing solvent to absorb the offgas under a high pressure. The low-pressure absorbing step or second absorbing step (17) is the step of allowing the absorbing solvent to absorb the offgas under a low pressure. The striping step (18) is the step of stripping a gaseous component or components absorbed in the high-pressure absorbing step (16) and/or in the low-pressure absorbing step (17).

Non-limiting examples of the absorbing solvent for use herein include an acetic acid-containing solvent and a methanol-containing solvent. For example, assume that acetic acid is used as the absorbing solvent. In this case, the offgas can be absorbed by the absorbing solvent and separated into a stream rich in carbon monoxide, and a stream rich in acetic acid, in the offgas treatment section (15). The acetic acid-containing solvent may have a composition typically as follows.

TABLE 50

|  | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppb to 0.1%) | 10 ppb to 0.01% | 100 ppb to 0.001% |
| CO | 0% to 1% (e.g., 1 ppb to 0.1%) | 10 ppb to 0.01% | 100 ppb to 0.001% |
| $CO_2$ | 0% to 1% (e.g., 1 ppb to 0.1%) | 10 ppb to 0.01% | 100 ppb to 0.001% |
| $CH_4$ | 0% to 1% (e.g., 1 ppb to 0.1%) | 10 ppb to 0.01% | 100 ppb to 0.001% |
| $N_2$ | 0% to 1% (e.g., 1 ppb to 0.1%) | 10 ppb to 0.01% | 100 ppb to 0.001% |
| AD | 0% to 1% (e.g., 1 ppb to 0.1%) | 10 ppb to 0.01% | 100 ppb to 0.001% |
| MeOH | 0% to 1% (e.g., 1 ppb to 0.1%) | 10 ppb to 0.01% | 100 ppb to 0.001% |
| MeI | 0% to 1% (e.g., 1 ppb to 0.1%) | 10 ppb to 0.01% | 100 ppb to 0.001% |
| MA | 0% to 1% (e.g., 1 ppb to 0.1%) | 10 ppb to 0.01% | 100 ppb to 0.001% |
| $H_2O$ | 10 ppm to 5% | 100 ppm to 2% | 0.1% to 1% |
| AcOH | 80% to 100% | 90% to 99.99% | 98% to 99.9% |
| HI | 0% to 1% (e.g., 0.1 ppb to 0.5%) | 1 ppb to 0.1% | 10 ppb to 100 ppm |
| FrOH | 0% to 1% (e.g., 1 to 300 ppm) | 5 to 100 ppm | 10 to 50 ppm |
| PrOH | 0% to 1% (e.g., 0.1 ppm to 0.1%) | 1 to 200 ppm | 10 to 100 ppm |
| DME | 0% to 1% (e.g., 1 ppb to 100 ppm) | 10 ppb to 10 ppm | 100 ppb to 5 ppm |
| AcA | 0% to 1% (e.g., 1 ppb to 0.1%) | 10 ppb to 100 ppm | 100 ppb to 50 ppm |
| $(CH_3)_2C=O$ | 0% to 1% (e.g., 1 ppb to 0.1%) | 10 ppb to 100 ppm | 100 ppb to 50 ppm |
| EtOH | 0% to 1% (e.g., 1 ppb to 0.1%) | 10 ppb to 100 ppm | 100 ppb to 50 ppm |
| EA | 0% to 1% (e.g., 1 ppb to 0.1%) | 10 ppb to 100 ppm | 100 ppb to 50 ppm |
| EtI | 0% to 1% (e.g., 1 ppb to 0.1%) | 10 ppb to 100 ppm | 100 ppb to 50 ppm |
| Li | 0% to 0.1% (e.g., 0.01 ppt to 100 ppb) | 1 ppt to 10 ppb | 10 ppt to 1 ppb |
| Rh | 0% to 0.1% (e.g., 0.01 ppt to 100 ppb) | 1 ppt to 10 ppb | 10 ppt to 1 ppb |

The methanol-containing solvent may have a composition typically as follows.

TABLE 51

|  | Range | Preferred range | More preferred range |
|---|---|---|---|
| $O_2$ | 10% or less (e.g., 0.1 ppb to 10%), e.g. 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppt to 0.1%) | 10 ppt to 0.01% | 100 ppt to 0.001% |
| CO | 0% to 1% (e.g., 1 ppt to 0.1%) | 10 ppt to 0.01% | 100 ppt to 0.001% |
| $CO_2$ | 0% to 1% (e.g., 1 ppt to 0.1%) | 10 ppt to 0.01% | 100 ppt to 0.001% |
| $CH_4$ | 0% to 1% (e.g., 1 ppt to 0.1%) | 10 ppt to 0.01% | 100 ppt to 0.001% |
| $N_2$ | 0% to 1 % (e.g., 1 ppt to 0.1%) | 10 ppt to 0.01% | 100 ppt to 0.001% |
| AD | 0% to 1% (e.g., 1 ppb to 0.1%) | 10 ppb to 0.01% | 100 ppb to 0.001% |
| MeOH | 95% to 100% | 98% to 99.999% | 99% to 99.99% |
| MeI | 0% to 1% (e.g., 1 ppt to 0.1%) | 10 ppt to 0.01% | 100 ppt to 0.001% |
| MA | 0% to 1% (e.g., 1 ppb to 0.1%) | 10 ppb to 0.01% | 100 ppb to 0.001% |
| $H_2O$ | 0% to 1% (e.g., 1 ppm to 0.1%) | 10 ppm to 0.05% | 100 ppm to 0.01% |
| AcOH | 0% to 1% (e.g., 1 ppb to 0.1%) | 10 ppb to 0.01% | 100 ppb to 0.001% |
| HI | 0% to 1% (e.g., 0.1 ppb to 0.5%) | 1 ppb to 0.1% | 10 ppb to 100 ppm |
| FrOH | 0% to 1% (e.g., 1 to 300 ppm) | 5 to 100 ppm | 10 to 50 ppm |
| PrOH | 0% to 1% (e.g., 0.1 ppm to 0.1%) | 1 to 200 ppm | 10 to 100 ppm |
| DME | 0% to 1% (e.g., 1 ppb to 100 ppm) | 10 ppb to 10 ppm | 100 ppb to 5 ppm |
| AcA | 0% to 1% (e.g., 1 ppb to 0.1%) | 10 ppb to 100 ppm | 100 ppb to 50 ppm |
| $(CH_3)_2C=O$ | 0% to 1% (e.g., 1 ppb to 100 ppm) | 10 ppb to 50 ppm | 100 ppb to 30 ppm |
| EtOH | 0% to 1% (e.g., 1 ppb to 100 ppm) | 10 ppb to 50 ppm | 100 ppb to 10 ppm |
| EA | 0% to 1% (e.g., 1 ppb to 100 ppm) | 10 ppb to 50 ppm | 100 ppb to 10 ppm |
| EtI | 0% to 1% (e.g., 1 ppb to 100 ppm) | 10 ppb to 50 ppm | 100 ppb to 10 ppm |
| Li | 0% to 0.1% (e.g., 0.01 ppt to 100 ppb) | 1 ppt to 10 ppb | 10 ppt to 1 ppb |
| Rh | 0% to 0.1% (e.g., 0.01 ppt to 100 ppb) | 1 ppt to 10 ppb | 10 ppt to 1 ppb |
| Fe | 0% to 0.1% (e.g., 1 ppb to 1 ppm) | 10 ppt to 0.5 ppm | 100 ppt to 0.1 ppm |

The methanol-containing solvent is often approximately devoid of detectable levels of methyl iodide (MeI), methyl acetate (MA), acetic acid (AcOH), hydrogen iodide (HI), formic acid (FrOH), propionic acid (PrOH), acetic anhydride (AcA), lithium (Li), and rhodium (Rh).

High-Pressure Absorbing Step (16)

In the offgas treatment section (15), the non-condensable gas (offgas rich in carbon monoxide and methyl iodide) 11 from the reactor (1) is brought in contact with, and scrubbed by, an acetic acid 197 as an absorbing solvent in the high-pressure absorber (16) in the high-pressure absorbing step (16), to be separated into an overhead stream 171 and a bottom (lower-part) acetic acid stream 174. The overhead stream (gas stream) 171 is rich in carbon monoxide. The bottom acetic acid stream 174 is rich in methyl iodide, methyl acetate, and water. Of the overhead stream 171, the portion 172 is fed to the evaporator (2); and the remainder 173 is fed to a boiler and is used as a heat source for the process, or is discharged to the air (atmosphere) through a flare stack or a vent stack. The remainder 173 of the overhead stream 171 may also be incinerated or recovered. The bottom acetic acid stream 174 is fed to a stripper (18).

The overhead stream 171 may have a composition typically as follows.

TABLE 52

| Average molecular weight: 26.22 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 5% (e.g., 0.001 to 2.5%) | 0.01% to 2% | 0.1% to 1% |
| CO | 1% to 99% | 5% to 90% | 10% to 85% |
| $CO_2$ | 0% to 5% (e.g., 0.01% to 5%) | 0.1% to 3% | 0.2% to 2% |
| $CH_4$ | 0.01% to 15% | 0.1% to 10% | 1% to 6% |
| $N_2$ | 0.01% to 20% | 0.1% to 15% | 1% to 10% |
| AD | 0% to 1% (e.g., 0.001% to 1%) | 0.01% to 0.5% | 0.02% to 0.2% |
| MeOH | 0% to 1% (e.g., 1 ppm to 1%) | 5 ppm to 0.5% | 10 ppm to 0.1% |
| MeI | 0% to 90% (e.g., 1% to 90%) | 5% to 80% (e.g., 10% to 70%) | 20% to 50% |
| MA | 0% to 5% (e.g., 0.001% to 2%) | 0.01% to 1% | 0.05% to 0.5% |
| $H_2O$ | 0% to 1% (e.g., 1 ppm to 1%) | 5 ppm to 0.5% | 10 ppm to 0.1% |
| AcOH | 0% to 10% (e.g., 0.001% to 10%) | 0.01% to 5% | 0.1% to 2% |
| HI | 0% to 1% (e.g., 1 ppm to 1%) | 5 ppm to 0.5% | 10 ppm to 0.1% |
| FrOH | 0% to 1% (e.g., 0.1 ppm to 0.5%) | 1 ppm to 0.2% | 10 ppm to 0.1% |
| PrOH | 0% to 1% (e.g., 0.1 ppm to 0.5%) | 1 ppm to 0.2% | 10 ppm to 0.1% |
| DME | 0% to 1% (e.g., 0.1 ppm to 1%) | 1 ppm to 0.1% | 5 ppm to 0.05% |
| $(CH_3)_2C=O$ | 0% to 1% (e.g., 1 ppt to 0.1%) | 10 ppt to 100 ppm | 100 ppt to 10 ppm |
| EtOH | 0% to 1% (e.g., 1 ppt to 0.1%) | 10 ppt to 100 ppm | 100 ppt to 10 ppm |
| EA | 0% to 1% (e.g., 1 ppt to 0.1%) | 10 ppt to 100 ppm | 100 ppt to 10 ppm |
| EtI | 0% to 1% (e.g., 1 ppt to 0.1%) | 10 ppt to 100 ppm | 100 ppt to 10 ppm |
| Li | 0% to 0.1% (e.g., 1 ppt to 0.1%) | 10 ppt to 100 ppm | 100 ppt to 10 ppm |
| Rh | 0% to 0.1% (e.g., 1 ppt to 0.1%) | 10 ppt to 100 ppm | 100 ppt to 10 ppm |

The bottom acetic acid stream 174 may have a composition typically as follows.

TABLE 53

| Average molecular weight: 59.64 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppm to 1%) | 10 ppm to 0.5% | 50 ppm to 0.1% |
| CO | 0% to 5% (e.g., 1 ppm to 2%) | 10 ppm to 1% | 100 ppm to 0.5% |
| $CO_2$ | 0% to 1% (e.g., 1 ppm to 1%) | 10 ppm to 0.5% | 50 ppm to 0.1% |
| $CH_4$ | 0% to 1% (e.g., 1 ppm to 1%) | 10 ppm to 0.5% | 50 ppm to 0.1% |
| $N_2$ | 0% to 1% (e.g., 1 ppm to 1%) | 10 ppm to 0.5% | 50 ppm to 0.1% |

TABLE 53-continued

| Average molecular weight: 59.64 | Range | Preferred range | More preferred range |
|---|---|---|---|
| AD | 0% to 1% (e.g., 0.1 ppm to 1%) | 1 ppm to 0.5% | 10 ppm to 0.1% |
| MeOH | 0% to 1% (e.g., 1 ppm to 1%) | 10 ppm to 0.5% | 50 ppm to 0.1% |
| MeI | 10 ppm to 10% | 100 ppm to 5% | 0.1% to 2% |
| MA | 10 ppm to 10% | 100 ppm to 5% | 0.1% to 2% |
| $H_2O$ | 10 ppm to 10% | 100 ppm to 5% | 0.1% to 2% |
| AcOH | 80% to 99.9% | 90% to 99.5% | 97% to 99% |
| HI | 0% to 1% (e.g., 0.1 ppb to 0.5%) | 1 ppb to 0.1% | 10 ppb to 100 ppm |
| FrOH | 0% to 1% (e.g., 1 ppm to 0.1%) | 5 to 200 ppm | 10 to 100 ppm |
| PrOH | 0% to 1% (e.g., 0.1 ppm to 0.1%) | 1 to 300 ppm | 10 to 100 ppm |
| DME | 0% to 1% (e.g., 1 ppb to 0.1%) | 10 ppb to 100 ppm | 100 ppb to 20 ppm |
| $(CH_3)_2C=O$ | 0% to 1% (e.g., 1 ppb to 0.1%) | 10 ppb to 100 ppm | 100 ppb to 50 ppm |
| EtOH | 0% to 1% (e.g., 1 ppb to 0.1%) | 10 ppb to 100 ppm | 100 ppb to 50 ppm |
| EA | 0% to 1% (e.g., 1 ppb to 0.1%) | 10 ppb to 100 ppm | 100 ppb to 50 ppm |
| EtI | 0% to 1% (e.g., 1 ppb to 0.1%) | 10 ppb to 100 ppm | 100 ppb to 50 ppm |
| Li | 0% to 0.1% (e.g., 0.1 ppt to 1000 ppb) | 1 ppt to 100 ppb | 10 ppt to 10 ppb |
| Rh | 0% to 0.1% (e.g., 0.1 ppt to 1000 ppb) | 1 ppt to 100 ppb | 10 ppt to 10 ppb |

Low-Pressure Absorbing Step (17)

The non-condensable gas (non-liquefied component in the decanter S2) 37, which has not been condensed in the condenser in the lower-boiling component-removing step (3), is mixed with the non-condensable gas (offgas rich in acetic acid, methyl iodide, and methyl acetate) 30 from the evaporator (2) to form a mixture (or gaseous mixture) 176, and the mixture 176 is brought into contact with, and scrubbed by, an acetic acid 196 as an absorbing solvent in the low-pressure absorber (17) in the low-pressure absorbing step (17), and is separated into an overhead stream 181 and a bottom acetic acid stream 182. The overhead stream 181 is rich in carbon monoxide, carbon dioxide, and nitrogen. The bottom acetic acid stream 182 is rich in acetic acid, methyl iodide, and methyl acetate. The overhead stream 181 is mixed with the overhead stream 171 from the high-pressure absorber (16) to form a gaseous mixture 173, and the gaseous mixture 173 is fed to a boiler and is used as a heat source for the process. Of the bottom acetic acid stream 182, a portion 184 is mixed with a portion of the bottom acetic acid stream 174 from the high-pressure absorber (16), and the resulting mixture is fed to the evaporator (2); and the remainder 183 is mixed with a bottom 175 from the high-pressure absorber (16) to form an acetic acid stream mixture 185, which is then fed to the stripper (18).

The mixture (or gaseous mixture) 176 may have a composition typically as follows.

TABLE 54

| Average molecular weight: 41.94 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.01% to 5% | 0.05% to 2% | 0.1% to 1% |
| CO | 1% to 99% | 5% to 80% | 10% to 70% |
| $CO_2$ | 0.1% to 20% | 0.5% to 15% | 1% to 15% |
| $CH_4$ | 0.1% to 20% | 0.5% to 15% | 1% to 10% |
| $N_2$ | 0.1% to 20% | 0.5% to 15% | 1% to 10% |
| AD | 0% to 10% (e.g., 0.001% to 7%) | 0.01% to 5% | 0.1% to 3% |
| MeOH | 0% to 1% (e.g., 1 ppm to 1%) | 5 ppm to 0.5% | 10 ppm to 0.1% |
| MeI | 1% to 95% | 10% to 90% | 20% to 80% |
| MA | 0.01% to 40% | 0.1% to 20% | 1% to 10% |
| $H_2O$ | 0% to 20% (e.g., 0.01% to 20%) | 0.02% to 10% | 0.05% to 1% |
| AcOH | 0% to 10% (e.g., 0.001% to 10%) | 0.01% to 1% | 0.03% to 0.5% |
| HI | 0% to 1% (e.g., 1 ppt to 0.1%) | 100 ppt to 0.01% | 10 ppb to 1 ppm |
| FrOH | 0% to 1% (e.g., 1 ppb to 0.1%) | 10 ppb to 100 ppm | 100 ppb to 10 ppm |
| PrOH | 0% to 1% (e.g., 1 ppb to 0.1%) | 10 ppb to 100 ppm | 100 ppb to 10 ppm |
| DME | 0% to 1% (e.g., 0.1 ppm to 1%) | 1 ppm to 0.1% | 5 ppm to 0.05% |
| $(CH_3)_2C=O$ | 0% to 1% (e.g., 0.01 ppm to 100 ppm) | 0.1 ppb to 10 ppm | 1 ppb to 1 ppm |
| EtOH | 0% to 1% (e.g., 0.01 ppm to 100 ppm) | 0.1 ppb to 10 ppm | 1 ppb to 1 ppm |
| EA | 0% to 1% (e.g., 0.01 ppm to 100 ppm) | 0.1 ppb to 10 ppm | 1 ppb to 1 ppm |
| EtI | 0% to 1% (e.g., 0.01 ppm to 100 ppm) | 0.1 ppb to 10 ppm | 1 ppb to 1 ppm |
| Li | 0% to 0.1% (e.g., 0.01 ppb to 100 ppm) | 0.1 ppb to 10 ppm | 1 ppb to 1 ppm |

TABLE 54-continued

| Average molecular weight: 41.94 | Range | Preferred range | More preferred range |
|---|---|---|---|
| Rh | 0% to 0.1% (e.g., 0.01 ppb to 100 ppm) | 0.1 ppb to 10 ppm | 1 ppb to 1 ppm |

The overhead stream (line 181) may have a composition typically as follows.

TABLE 55

| Average molecular weight: 26.57 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.01% to 10% | 0.1% to 5% | 0.2% to 2% |
| CO | 10% to 90% | 20% to 80% | 40% to 75% |
| $CO_2$ | 0.1% to 40% | 1% to 30% | 5% to 20% |
| $CH_4$ | 0.1% to 20% | 0.5% to 15% | 1% to 10% |
| $N_2$ | 0.1% to 20% | 1% to 15% | 2% to 10% |
| AD | 0% to 1% (e.g., 0.1 ppm to 1%) | 1 ppm to 0.5% | 10 ppm to 0.1% |
| MeOH | 0% to 1% (e.g., 1 ppm to 1%) | 5 ppm to 0.5% | 10 ppm to 0.1% |
| MeI | 0% to 1% (e.g., 0.01 ppm to 1%) | 0.1 ppm to 0.1% | 1 to 100 ppm |
| MA | 0% to 5% (e.g., 0.001% to 5%) | 0.01% to 1% | 0.05% to 0.5% |
| $H_2O$ | 0% to 1% (e.g., 1 ppm to 1%) | 5 ppm to 0.5% | 10 ppm to 0.1% |
| AcOH | 0% to 30% (e.g., 0.001% to 30%) | 0.01% to 10% | 0.1% to 5% |
| HI | 0% to 1% (e.g., 1 ppb to 1%) | 10 ppb to 0.1% | 100 ppb to 0.01% |
| FrOH | 0% to 1% (e.g., 0.01 ppm to 0.5%) | 0.1 ppm to 0.1% | 10 ppm to 0.01% |
| PrOH | 0% to 1% (e.g., 1 ppb to 0.1%) | 10 ppb to 0.01% | 100 ppb to 0.001% |
| DME | 0% to 1% (e.g., 0.1 ppm to 1%) | 1 ppm to 0.1% | 5 ppm to 0.05% |
| $(CH_3)_2C{=}O$ | 0% to 1% (e.g., 1 ppt to 0.1%) | 10 ppt to 100 ppm | 100 ppt to 10 ppm |
| EtOH | 0% to 1% (e.g., 1 ppt to 0.1%) | 10 ppt to 100 ppm | 100 ppt to 10 ppm |
| EA | 0% to 1% (e.g., 1 ppt to 0.1%) | 10 ppt to 100 ppm | 100 ppt to 10 ppm |
| EtI | 0% to 1% (e.g., 1 ppt to 0.1%) | 10 ppt to 100 ppm | 100 ppt to 10 ppm |
| Li | 0% to 0.1% (e.g., 1 ppt to 0.1%) | 10 ppt to 100 ppm | 100 ppt to 10 ppm |
| Rh | 0% to 0.1% (e.g., 1 ppt to 0.1%) | 10 ppt to 100 ppm | 100 ppt to 10 ppm |

The bottom acetic acid stream (line 182) may have a composition typically as follows.

TABLE 56

| Average molecular weight: 63.17 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppm to 1%) | 10 ppm to 0.5% | 50 ppm to 0.1% |
| CO | 0% to 2% (e.g., 1 ppm to 2%) | 10 ppm to 1% | 100 ppm to 0.5% |
| $CO_2$ | 0% to 5% (e.g., 1 ppm to 3%) | 10 ppm to 1% | 50 ppm to 0.5% |
| $CH_4$ | 0% to 1% (e.g., 1 ppm to 1%) | 10 ppm to 0.5% | 50 ppm to 0.1% |
| $N_2$ | 0% to 1% (e.g., 1 ppm to 1%) | 10 ppm to 0.5% | 50 ppm to 0.1% |
| AD | 0% to 5% (e.g., 1 ppm to 2%) | 10 ppm to 1% | 100 ppm to 0.5% |
| MeOH | 0% to 1% (e.g., 1 ppm to 1%) | 10 ppm to 0.5% | 50 ppm to 0.1% |
| MeI | 100 ppm to 30% | 0.1% to 20% | 1% to 15% |
| MA | 10 ppm to 10% | 100 ppm to 5% | 0.1% to 2% |
| $H_2O$ | 10 ppm to 10% | 100 ppm to 5% | 0.1% to 1% |
| AcOH | 70% to 99% | 80% to 98% | 85% to 95% |
| HI | 0% to 1% (e.g., 1 ppb to 0.5%) | 10 ppb to 0.1% | 100 ppb to 100 ppm |
| FrOH | 0% to 1% (e.g., 1 ppm to 0.1%) | 5 to 100 ppm | 10 to 50 ppm |

TABLE 56-continued

| Average molecular weight: 63.17 | Range | Preferred range | More preferred range |
|---|---|---|---|
| PrOH | 0% to 1% (e.g., 0.1 ppm to 0.1%) | 1 to 300 ppm | 10 to 100 ppm |
| DME | 0% to 1% (e.g., 1 ppb to 0.1%) | 10 ppb to 100 ppm | 100 ppb to 20 ppm |
| $(CH_3)_2C=O$ | 0% to 1% (e.g., 1 ppb to 0.1%) | 10 ppb to 100 ppm | 100 ppb to 50 ppm |
| EtOH | 0% to 1% (e.g., 1 ppb to 0.1%) | 10 ppb to 100 ppm | 100 ppb to 50 ppm |
| EA | 0% to 1% (e.g., 1 ppb to 0.1%) | 10 ppb to 100 ppm | 100 ppb to 50 ppm |
| EtI | 0% to 1% (e.g., 1 ppb to 0.1%) | 10 ppb to 100 ppm | 100 ppb to 50 ppm |
| Li | 0% to 0.1% (e.g., 0.1 ppt to 1000 ppb) | 1 ppt to 100 ppb | 10 ppt to 10 ppb |
| Rh | 0% to 0.1% (e.g., 0.1 ppt to 1000 ppb) | 1 ppt to 100 ppb | 10 ppt to 10 ppb |

Stripping Step (18)

In a stripper (stripping column) (18) in the stripping step (18), the acetic acid stream mixture 185 is distilled, stripped, and separated into an overhead stream 191 and a bottom acetic acid stream 194. The overhead stream 191 is rich in methyl iodide and acetic acid and further contains other components such as methyl acetate and acetaldehyde. The bottom acetic acid stream 194 is rich in acetic acid, methyl acetate, and water. Of the bottom acetic acid stream 194, a first portion is heated in a heating unit and returned to a lower part of the stripper (18); and a second portion (or the remainder) is mixed with a portion 65 of a condensate of the third overhead 61 from the heavy ends column (6) to give a liquid mixture 195, where the portion 65 is a portion of the condensate which is rich in acetic acid and stored in the hold tank T3. Of the liquid mixture 195, a portion 197 is recycled to an upper part of the high-pressure absorber (16); and the remainder 196 is recycled to an upper part of the low-pressure absorber (17).

The overhead stream 191 is cooled and condensed in a condenser to form a non-condensable gas 192 and a condensate 193. The non-condensable gas 192 is rich in methyl iodide and carbon monoxide and also contains other components such as carbon dioxide, methane, ethyl acetate, and acetaldehyde. The non-condensable gas 192 is mixed with the non-condensable gas from the decanter S2 in the liquid-liquid separation step (10), or with the non-condensable gas derived from the volatile phase 24 from the evaporator (2), to give a mixture, and the mixture is cooled and condensed in a condenser. The condensate 193 is rich in methyl iodide, acetic acid, and methyl acetate and also contains other components such as water and acetaldehyde. The condensate 193 is fed to the hold tank T1 which stores the condensates 26 and 28 derived from the volatile phase 24 from the evaporator (2). The condensate 193 is recycled via the hold tank T1 to the reactor (1). Alternatively, the condensate 193 may be recycled directly to the reactor (1).

The acetic acid stream mixture 185 may have a composition typically as follows.

TABLE 57

| Average molecular weight: 62.31 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppm to 1%) | 10 ppm to 0.5% | 50 ppm to 0.1% |
| CO | 0% to 2% (e.g., 1 ppm to 2%) | 10 ppm to 1% | 100 ppm to 0.5% |
| $CO_2$ | 0% to 2% (e.g., 1 ppm to 1%) | 10 ppm to 0.5% | 50 ppm to 0.2% |
| $CH_4$ | 0% to 1% (e.g., 1 ppm to 1%) | 10 ppm to 0.5% | 50 ppm to 0.1% |
| $N_2$ | 0% to 1% (e.g., 1 ppm to 1%) | 10 ppm to 0.5% | 50 ppm to 0.1% |
| AD | 0% to 2% (e.g., 1 ppm to 2%) | 10 ppm to 1% | 100 ppm to 0.5% |
| MeOH | 0% to 1% (e.g., 1 ppm to 1%) | 10 ppm to 0.5% | 50 ppm to 0.1% |
| MeI | 100 ppm to 30% | 0.1% to 20% | 1% to 15% |
| MA | 10 ppm to 10% | 100 ppm to 5% | 0.1% to 2% |
| $H_2O$ | 10 ppm to 10% | 100 ppm to 5% | 0.1% to 1% |
| AcOH | 70% to 99% | 80% to 98% | 85% to 95% |
| HI | 0% to 1% (e.g., 1 ppb to 0.5%) | 10 ppm to 0.1% | 100 ppb to 100 ppm |
| FrOH | 0% to 1% (e.g., 1 ppm to 0.1%) | 5 to 100 ppm | 10 to 50 ppm |
| PrOH | 0% to 1% (e.g., 0.1 ppm to 0.1%) | 1 to 300 ppm | 10 to 100 ppm |
| DME | 0% to 1% (e.g., 1 ppb to 0.1%) | 10 ppb to 100 ppm | 100 ppb to 50 ppm |
| $(CH_3)_2C=O$ | 0% to 1% (e.g., 1 ppb to 0.1%) | 10 ppb to 100 ppm | 100 ppb to 50 ppm |
| EtOH | 0% to 1% (e.g., 1 ppb to 0.1%) | 10 ppb to 100 ppm | 100 ppb to 50 ppm |
| EA | 0% to 1% (e.g., 1 ppb to 0.1%) | 10 ppb to 100 ppm | 100 ppb to 50 ppm |
| EtI | 0% to 1% (e.g., 1 ppb to 0.1%) | 10 ppb to 100 ppm | 100 ppb to 50 ppm |
| Li | 0% to 0.1% (e.g., 0.1 ppt to 1000 ppb) | 1 ppt to 100 ppb | 10 ppt to 10 ppb |

TABLE 57-continued

| Average molecular weight: 62.31 | Range | Preferred range | More preferred range |
|---|---|---|---|
| Rh | 0% to 0.1% (e.g., 0.1 ppt to 1000 ppb) | 1 ppt to 100 ppb | 10 ppt to 10 ppb |

The overhead stream 191 may have a composition typically as follows.

TABLE 58

| Average molecular weight: 95.18 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 2% (e.g., 0.1 ppm to 2%) | 1 ppm to 1% | 10 ppm to 0.1% |
| CO | 0.001% to 10% | 0.01% to 5% | 0.1% to 2% |
| $CO_2$ | 0.001% to 10% | 0.01% to 5% | 0.1% to 2% |
| $CH_4$ | 0% to 5% (e.g., 1 ppm to 5%) | 10 ppm to 2% | 100 ppm to 1% |
| $N_2$ | 0% to 2% (e.g., 0.1 ppm to 2%) | 1 ppm to 1% | 10 ppm to 0.1% |
| AD | 10 ppm to 5% | 100 ppm to 2% | 0.1% to 1% |
| MeOH | 0% to 1% (e.g., 1 ppm to 1%) | 5 ppm to 0.5% | 10 ppm to 0.1% |
| MeI | 5% to 99% | 10% to 90% | 30% to 80% |
| MA | 0.01% to 30% | 0.1% to 20% | 1% to 10% |
| $H_2O$ | 0.001% to 10% | 0.01% to 5% | 0.1% to 2% |
| AcOH | 0.1% to 50% | 1% to 40% | 5% to 30% |
| HI | 0% to 1% (e.g., 1 ppb to 1%) | 10 ppb to 0.1% | 100 ppb to 0.01% |
| FrOH | 0% to 1% (e.g., 0.01 ppm to 0.5%) | 0.1 ppm to 0.1% | 1 ppm to 0.01% |
| PrOH | 0% to 1% (e.g., 0.01 ppm to 0.5%) | 0.1 ppm to 0.1% | 1 ppm to 0.01% |
| DME | 0% to 1% (e.g., 0.1 ppm to 1%) | 1 ppm to 0.1% | 5 ppm to 0.05% |
| $(CH_3)_2C=O$ | 0% to 1% (e.g., 1 ppt to 0.1%) | 10 ppt to 100 ppm | 100 ppt to 10 ppm |
| EtOH | 0% to 1% (e.g., 1 ppt to 0.1%) | 10 ppt to 100 ppm | 100 ppt to 10 ppm |
| EA | 0% to 1% (e.g., 1 ppt to 0.1%) | 10 ppt to 100 ppm | 100 ppt to 10 ppm |
| EtI | 0% to 1% (e.g., 1 ppt to 0.1%) | 10 ppt to 100 ppm | 100 ppt to 10 ppm |
| Li | 0% to 0.1% (e.g., 1 ppt to 0.1%) | 10 ppt to 100 ppm | 100 ppt to 10 ppm |
| Rh | 0% to 0.1% (e.g., 1 ppt to 0.1%) | 10 ppt to 100 ppm | 100 ppt to 10 ppm |

The bottom acetic acid stream 194 may have a composition typically as follows.

TABLE 59

| Average molecular weight: 59.59 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0% to 1% (e.g., 1 ppb to 0.1%) | 10 ppb to 0.01% | 100 ppb to 0.001% |
| CO | 0% to 2% (e.g., 1 ppb to 1%) | 10 ppb to 0.5% | 100 ppb to 0.3% |
| $CO_2$ | 0% to 2% (e.g., 1 ppb to 1%) | 10 ppb to 0.5% | 100 ppb to 0.3% |
| $CH_4$ | 0% to 1% (e.g., 1 ppb to 0.1%) | 10 ppb to 0.01% | 100 ppb to 0.001% |
| $N_2$ | 0% to 1% (e.g., 1 ppb to 0.1%) | 10 ppb to 0.01% | 100 ppb to 0.001% |
| AD | 0% to 1% (e.g., 1 ppb to 0.1%) | 10 ppb to 0.01% | 100 ppb to 0.001% |
| MeOH | 0% to 1% (e.g., 1 ppb to 0.1%) | 10 ppb to 0.01% | 100 ppb to 0.001% |
| MeI | 0% to 1% (e.g., 1 ppb to 0.1%) | 10 ppb to 0.01% | 100 ppb to 0.001% |
| MA | 0% to 2% (e.g., 1 ppb to 1%) | 10 ppb to 0.5% | 100 ppb to 0.1% |
| $H_2O$ | 0% to 5% (e.g., 10 ppm to 5%) | 100 ppm to 2% | 0.1% to 1% |
| AcOH | 80% to 100% | 90% to 99.99% | 98% to 99.9% |
| HI | 0% to 1% (e.g., 0.1 ppb to 0.5%) | 1 ppb to 0.1% | 10 ppb to 100 ppm |
| FrOH | 0% to 1% (e.g., 1 to 100 ppm) | 5 to 1000 ppm | 10 to 300 ppm |

TABLE 59-continued

| Average molecular weight: 59.59 | Range | Preferred range | More preferred range |
|---|---|---|---|
| PrOH | 0% to 1% (e.g., 0.1 ppm to 0.1%) | 1 to 1000 ppm | 10 to 200 ppm |
| DME | 0% to 1% (e.g., 1 ppb to 100 ppm) | 10 ppb to 10 ppm | 100 ppb to 5 ppm |
| $(CH_3)_2C=O$ | 0% to 1% (e.g., 1 ppb to 0.1%) | 10 ppb to 100 ppm | 100 ppb to 50 ppm |
| EtOH | 0% to 1% (e.g., 1 ppb to 0.1%) | 10 ppb to 100 ppm | 100 ppb to 50 ppm |
| EA | 0% to 1% (e.g., 1 ppb to 0.1%) | 10 ppb to 100 ppm | 100 ppb to 50 ppm |
| EtI | 0% to 1% (e.g., 1 ppb to 0.1%) | 10 ppb to 100 ppm | 100 ppb to 50 ppm |
| Li | 0% to 0.1% (e.g., 1 ppb to 0.1%) | 10 ppb to 100 ppm | 100 ppb to 50 ppm |
| Rh | 0% to 0.1% (e.g., 0.01 ppt to 100 ppb) | 1 ppt to 10 ppb | 10 ppt to 1 ppb |

The portions 197 and 196 of the liquid mixture 195 may each typically have a composition approximately identical to or similar to the composition of the bottom acetic acid stream 194.

The non-condensable gas 192 derived from the overhead stream 191 may have a composition typically as follows.

TABLE 60

| Average molecular weight: 73.51 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0% to 2% (e.g., 1 ppm to 2%) | 10 ppm to 1% | 100 ppm to 0.2% |
| CO | 0.1% to 90% | 1% to 60% | 5% to 30% |
| $CO_2$ | 0.1% to 90% | 1% to 60% | 5% to 30% |
| $CH_4$ | 0.01% to 20% | 0.1% to 10% | 0.5% to 5% |
| $N_2$ | 0.01% to 20% | 0.1% to 10% | 0.3% to 3% |
| AD | 100 ppm to 20% | 0.1% to 10% | 0.5% to 5% |
| MeOH | 0% to 1% (e.g., 1 ppm to 1%) | 5 ppm to 0.5% | 10 ppm to 0.1% |
| MeI | 1% to 95% | 10% to 90% | 40% to 80% |
| MA | 0.01% to 20% | 0.1% to 10% | 0.5% to 5% |
| $H_2O$ | 10 ppm to 5% | 100 ppm to 2% | 500 ppm to 1% |
| AcOH | 10 ppm to 10% | 100 ppm to 5% | 0.1% to 2% |
| HI | 0% to 1% (e.g., 1 ppb to 1%) | 10 ppb to 0.1% | 100 ppb to 0.01% |
| FrOH | 0% to 1% (e.g., 0.01 ppm to 0.5%) | 0.1 ppm to 0.1% | 1 ppm to 0.01% |
| PrOH | 0% to 1% (e.g., 1 ppb to 0.1%) | 10 ppb to 0.01% | 100 ppb to 0.001% |
| DME | 0% to 1% (e.g., 0.1 ppm to 1%) | 1 ppm to 0.1% | 5 ppm to 0.05% |
| $(CH_3)_2C=O$ | 0% to 1% (e.g., 1 ppb to 0.1%) | 10 ppb to 100 ppm | 100 ppt to 10 ppm |
| EtOH | 0% to 1% (e.g., 1 ppb to 0.1%) | 10 ppb to 100 ppm | 100 ppt to 10 ppm |
| EA | 0% to 1% (e.g., 1 ppb to 0.1%) | 10 ppb to 100 ppm | 100 ppt to 10 ppm |
| EtI | 0% to 1% (e.g., 1 ppb to 0.1%) | 10 ppb to 100 ppm | 100 ppt to 10 ppm |
| Li | 0% to 0.1% (e.g., 1 ppt to 1 ppm) | 10 ppt to 0.1 ppm | 100 ppt to 0.01 ppm |
| Rh | 0% to 0.1% (e.g., 1 ppt to 1 ppm) | 10 ppt to 0.1 ppm | 100 ppt to 0.01 ppm |

The condensate 193 derived from the overhead stream 191 may have a composition typically as follows.

TABLE 61

| Average molecular weight: 97.27 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 pt to 1000 ppm), e.g., less than | 10 ppt to 300 ppm, e.g., 100 ppt to 100 ppm |

TABLE 61-continued

| Average molecular weight: 97.27 | Range | Preferred range | More preferred range |
|---|---|---|---|
| | | 700 ppm (e.g., 1 ppt to 500 ppm) | |
| $H_2$ | 0% to 1% (e.g., 1 ppm to 1%) | 10 ppm to 0.5% | 50 ppm to 0.1% |
| CO | 0% to 2% (e.g., 1 ppm to 2%) | 10 ppm to 1% | 100 ppm to 0.5% |
| $CO_2$ | 0% to 3% (e.g., 1 ppm to 1%) | 10 ppm to 1% | 50 ppm to 0.5% |
| $CH_4$ | 0% to 1% (e.g., 1 ppm to 1%) | 10 ppm to 0.5% | 50 ppm to 0.1% |
| $N_2$ | 0% to 1% (e.g., 1 ppm to 1%) | 10 ppm to 0.5% | 50 ppm to 0.1% |
| AD | 0% to 3% (e.g., 1 ppm to 2%) | 10 ppm to 1.5% | 100 ppm to 1% |
| MeOH | 0% to 1% (e.g., 1 ppm to 1%) | 10 ppm to 0.5% | 50 ppm to 0.1% |
| MeI | 10% to 95% | 30% to 90% | 50% to 80% |
| MA | 0.1% to 30% | 1% to 20% | 3% to 10% |
| $H_2O$ | 0.001% to 10% | 0.01% to 5% | 0.1% to 2% |
| AcOH | 1% to 70% | 5% to 50% | 10% to 35% |
| HI | 0% to 1% (e.g., 1 ppb to 0.5%) | 10 ppb to 0.1% | 100 ppb to 100 ppm |
| FrOH | 0% to 1% (e.g., 0.01 ppm to 0.1%) | 0.1 to 100 ppm | 1 to 50 ppm |
| PrOH | 0% to 1% (e.g., 0.01 ppm to 0.1%) | 0.1 to 300 ppm | 1 to 100 ppm |
| DME | 0% to 1% (e.g., 1 ppb to 0.1%) | 10 ppb to 100 ppm | 100 ppb to 20 ppm |
| $(CH_3)_2C=O$ | 0% to 1% (e.g., 1 ppb to 0.1%) | 10 ppb to 100 ppm | 100 ppb to 50 ppm |
| EtOH | 0% to 1% (e.g., 1 ppb to 0.1%) | 10 ppb to 100 ppm | 100 ppb to 50 ppm |
| EA | 0% to 1% (e.g., 1 ppb to 0.1%) | 10 ppb to 100 ppm | 100 ppb to 50 ppm |
| EtI | 0% to 1% (e.g., 1 ppb to 0.1%) | 10 ppb to 100 ppm | 100 ppb to 50 ppm |
| Li | 0% to 0.1% (e.g., 0.1 ppt to 1000 ppb) | 1 ppt to 100 ppb | 10 ppt to 10 ppb |
| Rh | 0% to 0.1% (e.g., 0.1 ppt to 1000 ppb) | 1 ppt to 100 ppb | 10 ppt to 10 ppb |

The offgas treatment section (15) often includes at least one absorbing step selected from the high-pressure absorbing step (16) and the low-pressure absorbing step (17), among the steps (16) to (18).

EXAMPLES

The present invention will be illustrated in further detail with reference to several examples below. It should be noted, however, that the examples are never construed to limit the scope of the present invention.

Corrosion tests employed test pieces as follows.

Test Pieces

Zr: zirconium, supplied by Allegheny Technologies Japan Ltd.

HB2: HASTELLOY B2 (nickel-based alloy), supplied by Oda Koki Co., Ltd.

HC276: HASTELLOY C (nickel-based alloy), supplied by Oda Koki Co., Ltd.

SUS316: stainless steel, supplied by Oda Koki Co., Ltd.

Samples were evaluated for corrosion-related test items as follows.

Test Piece Corrosion Rate

The mass of each test piece after the corrosion test was measured, on the basis of which the corrosion rate was calculated. Specifically, the mass loss of the test piece due to corrosion was measured to determine a corrosion rate of the test piece per year, and the corrosion rate was converted into a decrease in thickness (mm) of the test piece per year (in "mm/Y"), thus evaluating the corrosion amount (corrosion rate).

Partial Corrosion

Whether each test piece underwent partial corrosion was visually observed. The category "partial corrosion" includes bead corrosion, pitting corrosion, and spot corrosion.

Degree of Coloration

The APHA color (estimation of color in Hazen units; Hazen scale) of a liquid mixture was measured according to Japanese Industrial Standards (JIS). A greater APHA value means a higher degree of coloration.

Compositions (Component Proportions) of Liquid Phase and Gaseous Phase

In the compositions indicated in comparative examples, examples, and tables, the concentrations of organic substances and water were measured by gas chromatography, and the concentration of lithium iodide (LiI) was measured by atomic absorption spectrometry. The concentration of hydrogen iodide (HI) was calculated by subtracting the concentration of iodine ions ($I^-$) derived from iodides, from the total concentration of iodine ions. The totality of components in each of liquid phases and gaseous phases, including impurities and minor (or trace) components, is 100%. However, the total of the components indicated in the tables may be inconsistent with 100% in some cases, due to analysis error and rounding up or down to significant figures (or to number of significant digits).

For each of non-condensable gaseous components (hydrogen, carbon monoxide, carbon dioxide, methane, nitrogen, and oxygen) excluding methyl iodide, when a component had a concentration of less than 1 percent by mass and less than 1 percent by volume, the concentration of the component was rounded off to two significant digits; when a component had a concentration of 1 percent by mass or more and 1 percent by volume or more, the concentration of the component was rounded off to the nearest integer.

Comparative Examples 1 to 14 and Examples 1 to 22

Comparative Example 1

In a zirconium Zr autoclave (capacity: 500 ml), 39 g of MeI, 6.3 g of water, 0.003 g of HI, 8.4 g of MA, 207 g of acetic acid, 0.03 g of PA, and 46 g of LiI were placed. The test pieces (size: 36 mm by 25 mm by 2.5 mm) were placed in the autoclave, followed by closing of the autoclave with a lid. Oxygen dissolved in the liquid in the autoclave was replaced with nitrogen gas which was bubbled into the liquid, and then 0.003 g of DME and 0.06 g of AD were charged into the autoclave. An operation of increasing the pressure inside the autoclave from the atmospheric pressure up to 1 MPa with nitrogen gas and then releasing the pressure to the atmospheric pressure was performed three times. In addition, an operation of increasing the pressure up to 1 MPa with a gaseous mixture (93 percent by volume of CO and 7 percent by volume of $O_2$) and then releasing the pressure down to the atmospheric pressure was performed three times; and a gaseous mixture (93 percent by volume of CO and 7 percent by volume of $O_2$) was fed until the inside pressure of the autoclave reached 4 MPa, the pressure was then gradually released, and the oxygen concentration in the released gas was measured by an oxygen analyzer (galvanic oxygen analyzer Model 1000RS, supplied by TEKHNE Corporation) to check that the oxygen concentration reached 7 percent by volume. After releasing the pressure of the autoclave down to 1 MPa, the autoclave was heated up to 190° C. on an oil bath. The static pressure after the heating was maintained to 2.8 MPa. After elapse of 100 hours under the steady condition, the autoclave was cooled down to room temperature. A liquid mixture was sampled from a nozzle of the autoclave, analyzed on chemical composition, and subjected to a measurement of the degree of coloration (APHA color). In addition, the atmosphere in the autoclave was replaced with (purged with) nitrogen gas, and the autoclave was opened. The test pieces were retrieved and weighed (measured on mass) to determine a corrosion rate.

The concentration of oxygen in the gaseous phase was 7 percent by volume. The concentration of oxygen dissolved in the liquid phase at a total pressure of 1 MPa was calculated by Aspen Plus (manufactured by Aspen Technology, Inc.) and was found to be $7.0 \times 10^{-5}$ g/g.

Comparative Examples 2 to 11

Corrosion tests were performed by a procedure similar to that in Comparative Example 1, except for changing the feed composition, the pressure, and the heating temperature.

Comparative Example 12

A corrosion test was performed by a procedure similar to that in Comparative Example 1, except for changing the feed composition, the feed gas composition (to 93 percent by volume of $N_2$ and 7 percent by volume of $O_2$), the pressure, and the heating temperature.

Comparative Example 13

In the process for continuously producing acetic acid illustrated in FIG. 1, methanol was allowed to continuously react with carbon monoxide (carbon monoxide having an oxygen concentration of 10 percent by mass (9 percent by volume)) in the carbonylation reactor, and the reaction mixture from the reactor was continuously fed to the flasher for flash evaporation to be separated into a less-volatile phase and a volatile phase. The less-volatile phase was a bottom component containing a rhodium catalyst, lithium iodide, acetic acid, methyl acetate, methyl iodide, water, and hydrogen iodide. The volatile phase was a gaseous component that gave a liquefied product having a temperature of 140° C. The volatile phase was fed to the light ends column.

The volatile phase contained 26.8 percent by mass of methyl iodide (MeI), 4.5 percent by mass of methyl acetate (MA), 2.0 percent by mass of water ($H_2O$), 500 ppm by mass of hydrogen iodide (HI), 600 ppm by mass of acetaldehyde (AD), 62.8 percent by mass of acetic acid, 0.0070 percent by mass (70 ppm by mass) of hydrogen, 2 percent by mass of carbon monoxide, 0.060 percent by mass (600 ppm by mass) of carbon dioxide, 0.070 percent by mass (700 ppm by mass) of methane, 0.070 percent by mass (700 ppm by mass) of nitrogen, and oxygen and other minor components (100 percent by mass in total).

A vapor and/or a liquid of acetic acid, if entering a pressure sensor unit of a differential-pressure level gauge for measuring the liquid level of the bottom liquid in the light ends column, may cause malfunction (misoperation) of the level gauge. To eliminate or minimize this, 9 parts by mass of purge air, relative to 100 parts by mass of the volatile phase fed to the light ends column, was supplied to the gaseous phase side of the differential-pressure level gauge.

The volatile phase (100 parts by mass) was fed to the light ends column (actual number of plates: 20 plates, feed plate: the 2nd plate from the bottom) and was distilled at a gauge pressure of 150 kPa, a column bottom temperature of 143° C., a column top temperature of 115° C., and a lighter phase reflux ratio of 12. The resulting overhead was cooled in a condenser to form a condensate and a non-condensable gas. The condensate (temperature: 40° C.) was liquid-liquid separated in a decanter to form an aqueous phase (lighter phase) and an organic phase (heavier phase); and 1.3 parts by mass of the aqueous phase and 30 parts by mass of the organic phase were recycled to the reactor. From the condenser, 13 parts by mass of the non-condensable gas (offgas stream) were withdrawn.

The overhead from the light ends column had a composition (composition at the column top) as follows: 43.2 percent by mass of methyl iodide (MeI), 7.5 percent by mass of methyl acetate (MA), 21.1 percent by mass of water ($H_2O$), 100 ppm by mass of hydrogen iodide (HI), 5.9 percent by mass of acetic acid, 0.010 percent by mass (100 ppm by mass) of hydrogen, 4 percent by mass of carbon monoxide, 0.10 percent by mass (1000 ppm by mass) of carbon dioxide, 0.11 percent by mass (1100 ppm by mass) of methane, 12 percent by mass of nitrogen, 6 percent by mass (7 percent by volume) of oxygen, and other minor components (100 percent by mass in total). The non-condensable gas (offgas stream) from the condenser had a composition as follows: 3.6 percent by mass of methyl iodide (MeI), 0.2 percent by mass of methyl acetate (MA), 200 ppm by mass of water ($H_2O$), hydrogen iodide (HI) (not measured), 200 ppm by mass of acetic acid, 0.040 percent by mass (400 ppm by mass) of hydrogen, 17 percent by mass of carbon monoxide, 0.50 percent by mass of carbon dioxide, 0.50 percent by mass of methane, 53 percent by mass of nitrogen, 25 percent by mass (23 percent by volume) of oxygen, and other minor components (100 percent by mass in total). The aqueous phase (lighter phase) from the condenser had a composition as follows: 3.3 percent by mass of methyl iodide (MeI), 6.6 percent by mass of methyl acetate (MA), 73.0 percent by mass of water ($H_2O$), 100 ppm by mass of hydrogen iodide (HI), 17.0 percent by mass of acetic acid, 0.0080 percent by mass (80 ppm by mass) of oxygen, and other minor components (100 percent by mass in total). The organic phase (heavier phase) from the condenser had a composition as follows: 86 percent by mass of methyl iodide (MeI), 11.1 percent by mass of methyl acetate (MA), 0.5 percent by mass of water ($H_2O$), 100 ppm by mass of hydrogen iodide (HI), 2.0 percent by mass of acetic acid, 0.0090 percent by mass (90 ppm by mass) of oxygen, and other minor components (100 percent by mass in total).

A side-cut stream (62.8 parts by mass) from the light ends column was fed to the dehydration column for dehydration and purification. The side-cut stream had a composition as follows: 2.4 percent by mass of methyl iodide (MeI), 1.6 percent by mass of methyl acetate (MA), 1.3 percent by mass of water ($H_2O$), 45 ppm by mass of hydrogen iodide (HI), 94.6 percent by mass of acetic acid, 0.0090 percent by mass (90 pm by mass) of oxygen, and other minor components (100 percent by mass in total). The remainder of the feed (volatile phase) was recycled as a bottom stream to the reactor. The term "part by mass" for a fluid refers to a flow rate per unit time (1 hour) (hereinafter the same), where non-limiting examples of the fluid include volatile phases, aqueous phases (lighter phases), organic phases (heavier phases), offgas streams, side-cut streams, and bottom streams.

In the continuous reaction process as above, the test pieces were placed on the feed plate (the 2nd plate from the bottom, at a temperature of 140° C.) and the upper part (the 19th plate from the bottom) of light ends column. After the process was operated for 500 hours, each test piece was examined for a corrosion test. The mass of the test piece was measured before and after the corrosion test, on the basis of which a corrosion amount was determined.

In addition, a crude acetic acid (side-cut stream) from the light ends column was examined for the APHA color.

Comparative Example 14

In the process for continuously producing acetic acid illustrated in FIG. 1, methanol was allowed to continuously react with carbon monoxide (oxygen concentration: 10 ppm by mass) in the carbonylation reactor. A volatile phase from the evaporator was distilled in the light ends column; and 100 parts by mass of a side-cut stream from the light ends column is fed to the dehydration column for dehydration and purification, by a procedure similar to that in Comparative Example 13. A vapor and/or a liquid of acetic acid, if entering a pressure sensor unit of a differential-pressure level gauge for measuring the liquid level of the bottom liquid in the dehydration column, may cause malfunction (misoperation) of the level gauge. To eliminate or minimize this, 11 parts by mass of purge air, relative to 100 parts by mass of the side-cut stream fed to the differential-pressure level gauge, was supplied to the gaseous phase side of the differential-pressure level gauge.

In the dehydration column (actual number of plates: 50 plates, spacing between a feed plate and a plate from which an overhead vapor was withdrawn: 15 plates as actual plates), distillation was performed at a column top gauge pressure of 200 kPa, a column bottom temperature of 161° C., a column top temperature of 150° C., and a reflux ratio of 0.5, where the reflux ratio is the ratio of the reflux amount to the distillate amount.

From the column top of the dehydration column, 60 parts by mass of an overhead were withdrawn. The overhead had a composition as follows: 6.3 percent by mass of methyl iodide (MeI), 4.1 percent by mass of methyl acetate (MA), 3.3 percent by mass of water ($H_2O$), 10 ppm by mass of hydrogen iodide (HI), 0 ppm by mass of hydrogen, 0.00010 percent by mass (1.0 ppm by mass) of carbon monoxide, 0 ppm by mass of carbon dioxide, 0 ppm by mass of methane, 14 percent by mass of nitrogen, 4 percent by mass (7 percent by volume) of oxygen, and other minor components, with the remainder approximately being acetic acid.

The overhead from the dehydration column was cooled in a condenser to form a condensate and a non-condensable gas. The condensate was held in a reflux tank. Of the condensate in the tank, a portion (32 parts by mass) was withdrawn from the tank and recycled to the reactor; and another portion (16 parts by mass) was refluxed to the dehydration column at a reflux ratio of 0.5. The condensate had a composition as follows: 7.7 percent by mass of methyl iodide (MeI), 5.0 percent by mass of methyl acetate (MA), 4.1 percent by mass of water ($H_2O$), 9 ppm by mass of hydrogen iodide (HI), 0.0070 percent by mass (70 ppm by mass) of oxygen, and other minor components, with the remainder approximately being acetic acid. From the condenser, 11 parts by mass of the non-condensable gas were withdrawn. The non-condensable gas had a composition as follows: 22 percent by mass (20 percent by volume) of oxygen, 78 percent by mass (70 percent by volume) of nitrogen, and negligible amounts of other components.

A crude acetic acid resulting from the dehydration and purification was withdrawn as a bottom stream from the dehydration column. The bottom stream (crude acetic acid) had a composition as follows: 6 ppb by mass of methyl iodide (MeI), 0.05 percent by mass of water ($H_2O$), 4 ppb by mass of hydrogen iodide (HI), 6 ppm by mass of methyl acetate (MA), and other minor components (including oxygen), with the remainder approximately being acetic acid. The term "part by mass" for a fluid refers to a flow rate per unit time (1 hour) (hereinafter the same), where non-limiting examples of the fluid include feed liquids, overheads (distillates), offgas streams, and bottom streams.

In the continuous reaction process as above, the test pieces were placed on the 2nd plate from the bottom (on a plate above the air purge line) and the column top (the 50th plate from the bottom) of the dehydration column and were left for 500 hours, and each test piece was examined for a corrosion test. The mass of the test piece was measured before and after the test, on the basis of which a corrosion amount was determined.

The feed liquid to be fed to the dehydration column (the side-cut stream from the light ends column) and of the bottom stream (crude acetic acid) from the dehydration column were examined for the APHA color.

Examples 1 to 10

Corrosion tests were performed in Examples 1 to 10 by procedures similar to those respectively in Comparative Examples 1 to 10, except for changing the feed gas composition. The feed gas used herein was a gaseous mixture containing 0.010 percent by volume of oxygen, with the remainder approximately being carbon monoxide.

Example 11

A corrosion test was performed by a procedure similar to that in Comparative Example 12, except for changing the feed gas composition (to 95 percent by volume of CO and 5 percent by volume of O2). The gaseous phase had an oxygen concentration of 1 percent by volume. The concentration of oxygen dissolved in the liquid phase under a total pressure of 140 kPa was calculated to be $4.0 \times 10^{-6}$ g/g using Aspen Plus (supplied by Aspen Technology, Inc.).

Example 12

A corrosion test was performed by a procedure similar to that in Comparative Example 12, except for changing the feed gas composition (to 99 percent by volume of CO and 1 percent by volume of O2).

Example 13

A corrosion test was performed by a procedure similar to that in Comparative Example 12, except for changing the feed gas composition. The feed gas used herein was a gaseous mixture containing 0.00010 percent by volume (1.0 ppm by volume) of oxygen, with the remainder approximately being carbon monoxide. However, in the test, pressurization up to 1 MPaG with a gaseous mixture (a gaseous mixture containing 0.00010 percent by volume of oxygen, with the remainder approximately being carbon monoxide) and pressure release to the atmospheric pressure were further repeated four times, until the oxygen concentration in the released gas reached 1.0 ppm by volume. Specifically, the pressurization up to 1 MPaG and the pressure release to the atmospheric pressure were repeated seven times in total as a result, and thereafter, the pressure was increased to 4 MPa and was then released. After checking that the oxygen concentration in the released gas reached 1.0 ppm by volume by measurement with an oxygen analyzer, the corrosion test was performed by a procedure similar to that in Comparative Example 12.

Example 14

A corrosion test was performed by a procedure similar to that in Comparative Example 12, except for changing the feed gas composition. The feed gas used herein was a gaseous mixture containing 0.10 percent by volume of oxygen, with the remainder approximately being nitrogen.

Example 15

A corrosion test was performed by a procedure similar to that in Comparative Example 12, except for changing the feed gas composition. The feed gas used herein was a gaseous mixture containing 0.010 percent by volume of oxygen, with the remainder approximately being nitrogen.

Example 16

A corrosion test was performed by a procedure similar to that in Comparative Example 12, except for changing the feed gas composition. The feed gas used herein was a gaseous mixture containing 0.0010 percent by volume of oxygen, with the remainder approximately being nitrogen. However, in the test, pressurization up to 1 MPaG with a gaseous mixture (a gaseous mixture containing 0.0010 percent by volume of oxygen, with the remainder approximately being nitrogen) and pressure release down to the atmospheric pressure were further repeated three times, until the oxygen concentration in the released gas reached 0.0010 percent by volume. Specifically, the pressure release down to the atmospheric pressure and the pressurization up to 1 MPaG were repeated six times in total as a result, and thereafter, the pressure was increased up to 4 MPa and was then released. After checking that the oxygen concentration in the released gas reached 0.0010 percent by volume by measurement with an oxygen analyzer, the corrosion test was performed by a procedure similar to that in Comparative Example 12.

Example 17

A corrosion test was performed by a procedure similar to that in Comparative Example 12, except for changing the feed gas composition. The feed gas used herein was a gaseous mixture containing 2 percent by volume of $H_2$, 15 percent by volume of $CO_2$, 7 percent by volume of $CH_4$, 8 percent by volume of $N_2$, and 0.010 percent by volume of $O_2$, with the remainder approximately being carbon monoxide CO.

Example 18

A corrosion test was performed by a procedure similar to that in Comparative Example 11, except for changing the feed gas composition. The feed gas used herein was a gaseous mixture containing 0.00010 percent by volume (1.0 ppm by volume) of oxygen, with the remainder approximately being carbon monoxide. However, in the test, pressurization up to 1 MPaG with a gaseous mixture (a gaseous mixture containing 0.00010 percent by volume of oxygen, with the remainder approximately being carbon monoxide) and pressure release down to the atmospheric pressure was further repeated four times, until the oxygen concentration in the released gas reached 1.0 ppm by volume. Specifically, the pressure release down to the atmospheric pressure and the pressurization up to 1 MPaG were repeated seven times in total as a result, and thereafter, the pressure was increased up to 4 MPa and was then released. After checking that the oxygen concentration in the released gas reached 1.0 ppm by volume by measurement with an oxygen analyzer, the corrosion test was performed by a procedure similar to that in Comparative Example 11.

Example 19

A corrosion test was performed by a procedure similar to that in Comparative Example 11, except for changing the feed gas composition. The feed gas used herein was a gaseous mixture containing 0.000010 percent by volume (0.10 ppm by volume) of oxygen, with the remainder approximately being carbon monoxide. However, in the test, pressurization up to 1 MPaG with a gaseous mixture (a gaseous mixture containing 0.000010 percent by volume of oxygen, with the remainder approximately being carbon monoxide) and subsequent pressure release down to the atmospheric pressure were further performed four times, until the oxygen concentration in the released gas reached 0.10 ppm by volume. Specifically, the pressure release down to the atmospheric pressure and the pressurization up to 1 MPaG were repeated seven times in total as a result, and thereafter, the pressure was increased up to 4 MPa and then released. After checking that the oxygen concentration in the released gas reached 0.10 ppm by volume by measurement with an oxygen analyzer, the corrosion test was performed by a procedure similar to that in Comparative Example 11.

Example 20

A corrosion test was performed by a procedure similar to that in Comparative Example 13, except for regulating (lowering) the oxygen concentration in the carbon monoxide fed to the carbonylation reactor, and thereby causing the volatile phase from the evaporator to have an oxygen concentration of 0.1 percent by mass instead of 3 percent by mass. Lowering of the oxygen concentration in the carbon monoxide varied the composition of the volatile phase to be fed to the light ends column. Specifically, the volatile phase had a composition as follows: 27.6 percent by mass of methyl iodide (MeI), 4.6 percent by mass of methyl acetate (MA), 2.0 percent by mass of water ($H_2O$), 450 ppm by mass of hydrogen iodide (HI), 64.6 percent by mass of acetic acid, 0.0070 percent by mass (70 ppm by mass) of hydrogen, 0.60 percent by mass (6000 ppm by mass) of carbon monoxide, 0.070 percent by mass (700 ppm by mass) of carbon dioxide, 0.070 percent by mass (700 ppm by mass) of methane, 0.070 percent by mass (700 ppm by mass) of nitrogen, 0.30 percent by mass (0.60 percent by volume) of oxygen, and other minor components (100 percent by mass in total). The overhead from the light ends column had a composition (composition at the column top) as follows: 54.2 percent by mass of methyl iodide (MeI), 9.4 percent by mass of methyl acetate (MA), 26.5 percent by mass of water ($H_2O$), 100 ppm by mass of hydrogen iodide (HI), 7.3 percent by mass of acetic acid, 0.010 percent by mass (100 ppm by mass) of hydrogen, 1 percent by mass of carbon monoxide, 0.14 percent by mass (1400 ppm by mass) of carbon dioxide, 0.15 percent by mass (1500 ppm by mass) of methane, 0.15 percent by mass (1500 ppm by mass) of nitrogen, 0.20 percent by mass (2000 ppm by mass) (0.30 percent by volume) of oxygen, and other minor components (100 percent by mass in total). From the condenser for cooling the overhead, 1.4 parts by mass of a non-condensable gas (offgas stream) were withdrawn. The non-condensable gas had a composition as follows: 35 percent by mass of methyl iodide (MeI), 2.0 percent by mass of methyl acetate (MA), 1000 ppm by mass of water ($H_2O$), hydrogen iodide (HI) (not measured), 700 ppm by mass of acetic acid, 0.50 percent by mass (5000 ppm by mass) of hydrogen, 41 percent by mass of carbon monoxide, 5 percent by mass of carbon dioxide, 5 percent by mass of methane, 5 percent by mass of nitrogen, 6 percent by mass (6 percent by volume) of oxygen, and other minor components (100 percent by mass in total). The condensate derived from the overhead was liquid-liquid separated in a decanter to form an aqueous phase (lighter phase) and an organic phase (heavier phase), and 1.4 parts by mass of the aqueous phase and 30 parts by mass of the organic phase were recycled to the reactor. The bottom stream (3 parts by mass) from the light ends column was recycled to the reactor, and the remainder of the feed (volatile phase) was withdrawn as a side-cut stream from the light ends column. The compositions of these process streams (the aqueous phase, the organic phase, and the side-cut stream) were approximately identical to those in Comparative Example 13.

Example 21

A corrosion test was performed by a procedure similar to that in Comparative Example 14, except that 1 part by mass of purge nitrogen containing 6 percent by mass of oxygen, per 100 parts by mass of the feed amount of the side-cut stream of the light ends column, was supplied to the gaseous phase side of the differential-pressure level gauge for measuring the liquid level of the bottom liquid in the dehydration column.

An overhead (50 parts by mass) was withdrawn from the column top of the dehydration column. The overhead had a composition as follows: 7.5 percent by mass of methyl iodide (MeI), 4.9 percent by mass of methyl acetate (MA), 4.0 percent by mass of water ($H_2O$), 10 ppm by mass of hydrogen iodide (HI), 0 ppm by mass of hydrogen, 0.00010 percent by mass (1.0 ppm by mass) of carbon monoxide, 0 ppm by mass of carbon dioxide, 0 ppm by mass of methane, 2 percent by mass of nitrogen, 0.40 percent by mass (0.90 percent by volume) of oxygen, and other minor components, with the remainder approximately being acetic acid.

The overhead from the dehydration column was cooled in a condenser to form a condensate and a non-condensable gas and the condensate was held in a reflux tank. Of the condensate in the reflux tank, a portion (32 parts by mass) was withdrawn and recycled to the reactor; and another portion (16 parts by mass) was refluxed to the dehydration column at a reflux ratio of 0.5. The condensate had a composition as follows: 7.7 percent by mass of methyl iodide (MeI), 5.0 percent by mass of methyl acetate (MA), 4.1 percent by mass of water ($H_2O$), 9 ppm by mass of hydrogen iodide (HI), 0.00020 percent by mass (2.0 ppm by mass) of oxygen, and other minor components, with the remainder approximately being acetic acid. From the condenser, 1 part by mass of the non-condensable gas was withdrawn. The non-condensable gas had a composition as follows: 7 percent by mass (6 percent by volume) of oxygen, 93 percent by mass (94 percent by volume) of nitrogen, and negligible amounts of other components. A bottom stream (crude acetic acid) from the dehydration column had a composition as follows: 4 ppb by mass of methyl iodide (MeI), 0.05 percent by mass of water ($H_2O$), 5 ppb by mass of hydrogen iodide (HI), 5 ppm by mass of methyl acetate (MA), and other minor components (including oxygen), with the remainder approximately being acetic acid.

Example 22

In the process for continuously producing acetic acid illustrated in FIG. 1, methanol was allowed to continuously react with carbon monoxide (carbon monoxide containing 2 percent by mass (2 percent by volume) of oxygen) in the carbonylation reactor. The reaction mixture from the reactor was continuously fed to the evaporator for flash evaporation to form a less-volatile phase and a volatile phase. The less-volatile phase was a bottom component containing a rhodium catalyst, lithium iodide, acetic acid, methyl acetate, methyl iodide, water, and hydrogen iodide. The volatile phase contained a gaseous component which gave a liquefied product having a temperature of 140° C. The volatile phase contained 27.1 percent by mass of methyl iodide (MeI), 4.5 percent by mass of methyl acetate (MA), 2.0 percent by mass of water ($H_2O$), 500 ppm by mass of hydrogen iodide (HI), 63.5 percent by mass of acetic acid, 0.0070 percent by mass (70 ppm by mass) of hydrogen, 2 percent by mass of carbon monoxide, 0.060 percent by mass (600 ppm by mass) of carbon dioxide, 0.070 percent by mass (700 ppm by mass) of methane, 0.070 percent by mass (700 ppm by mass) of nitrogen, 0.30 percent by mass (0.70 percent by volume) of oxygen, and other minor components (100 percent by mass in total).

The volatile phase (100 parts by mass) was fed to a dehydration column (actual number of plates: 20 plates, feed plate: the 2nd plate from the bottom) and distilled at a gauge pressure of 150 kPa, a column bottom temperature of 143° C., a column top temperature of 115° C., and a lighter phase reflux ratio of 12. The resulting overhead from the column top was cooled in a condenser to form a condensate and a non-condensable gas. The condensate (temperature: 40° C.) was liquid-liquid separated in a decanter to form an aqueous phase (lighter phase) and an organic phase (heavier phase), from which 1.3 parts by mass of the aqueous phase and 30 parts by mass of the organic phase were recycled to the reactor. From the condenser, 4.1 parts by mass of the non-condensable gas (offgas stream) were withdrawn. The overhead from the light ends column had a composition (composition at the column top) as follows: 52.4 percent by mass of methyl iodide (MeI), 9.1 percent by mass of methyl acetate (MA), 25.6 percent by mass of water ($H_2O$), 100 ppm by mass of hydrogen iodide (HI), 7.1 percent by mass of acetic acid, 0.010 percent by mass (100 ppm by mass) of hydrogen, 5 percent by mass of carbon monoxide, 0.12 percent by mass (1200 ppm by mass) of carbon dioxide, 0.14 percent by mass (1400 ppm by mass) of methane, 0.14 percent by mass (1400 ppm by mass) of nitrogen, 0.50 percent by mass (0.70 percent by volume) of oxygen, and other minor components (100 percent by mass in total); and the non-condensable gas (offgas stream) from the condenser had a composition as follows: 15 percent by mass of methyl iodide (MeI), 1 percent by mass of methyl acetate (MA), 200 ppm by mass of water ($H_2O$), hydrogen iodide (HI) (not measured), 200 ppm by mass of acetic acid, 0.20 percent by mass (2000 ppm by mass) of hydrogen, 71 percent by mass of carbon monoxide, 2 percent by mass of carbon dioxide, 2 percent by mass of methane, 2 percent by mass of nitrogen, 6 percent by mass (6 percent by volume) of oxygen, and other minor components (100 percent by mass in total). The aqueous phase (lighter phase) had a composition as follows: 3.3 percent by mass of methyl iodide (MeI), 6.6 percent by mass of methyl acetate (MA), 73.0 percent by mass of water ($H_2O$), 100 ppm by mass of hydrogen iodide (HI), 17.0 percent by mass of acetic acid, 0.0014 percent by mass (14 ppm by mass) of oxygen, and other minor components (100 percent by mass in total); and the organic phase (heavier phase) had a composition as follows: 86 percent by mass of methyl iodide (MeI), 11.4 percent by mass of methyl acetate (MA), 0.6 percent by mass of water ($H_2O$), 100 ppm by mass of hydrogen iodide (HI), 1.9 percent by mass of acetic acid, 0.0016 percent by mass (16 ppm by mass) of oxygen, and other minor components (100 percent by mass in total).

A side-cut stream (62.8 parts by mass) from the light ends column was fed to the dehydration column for dehydration and purification. The side-cut stream had a composition as follows: 2.4 percent by mass of methyl iodide (MeI), 1.6 percent by mass of methyl acetate (MA), 1.3 percent by mass of water ($H_2O$), 48 ppm by mass of hydrogen iodide (HI), 94.6 percent by mass of acetic acid, 0.0010 percent by mass (10 ppm by mass) of oxygen, and other minor components (100 percent by mass in total). The remainder of the feed (volatile phase) was recycled as a bottom stream to the reactor.

In the continuous reaction process as above, the test pieces were placed on the feed plate (the 2nd plate from the bottom, temperature: 140° C.) and the column top (the 19th plate from the bottom) of the light ends column. After the process was operated for 500 hours, each test piece was subjected to a corrosion test, was examined for mass before and after the test, on the basis of which a corrosion amount was determined.

The crude acetic acid (side-cut stream) from the light ends column was examined for the APHA color.

Tables 62 to 66 present the compositions (component proportions) and the results of the corrosion tests. Table 62 presents the compositions of the liquid phases in Comparative Examples 1 to 12; Table 63 presents the compositions of the liquid phases in Examples 1 to 19; Table 64 presents the compositions of the gas phases in Comparative Examples 1 to 12 and Examples 1 to 19; and Tables 65 and 66 present the results of the corrosion tests. In Tables 62 to 64, "wt %" represents percent by mass, "vol %" represents percent by volume, "MeI" represents methyl iodide, "HI" represents hydrogen iodide, "MA" represents methyl acetate, "MeOH" represents methanol, "Ac" represents acetic acid, "AD" represents acetaldehyde, "PA" represents propionic acid, "LiI" represents lithium iodide, and "FrOH" represents formic acid.

In comparative examples and examples performed at an oxygen concentration in a gaseous phase of 1 to 7 percent by volume, the oxygen concentration after the corrosion test decreased by about 0 to about 2 percent by volume; whereas examples performed at an oxygen concentration in a gaseous phase of less than 1 percent by volume, the oxygen concentration after the corrosion test decreased by about 2 to about 10 percent by volume.

Since it is difficult to measure the concentration of DME as having a low boiling point, a calculated concentration of fed DME was defined as the concentration of DME herein.

When oxygen in a liquid is replaced with nitrogen gas by bubbling after feeding of the liquid, a portion of components in the liquid mixture was discharged to the outside of the system in accompanying with the nitrogen gaseous phase. This causes a difference between the feed composition and the composition after the test, particularly in methyl iodide concentration.

For all the comparative examples and examples excluding Comparative Examples 8 and 9 and Examples 8 and 9, a peak derived from DME was detected by gas chromatography in a liquid after the completion of the test. The concentration of DME calculated from the area percentage of the peak was found to be about 10 to about 1000 ppm by mass.

TABLE 62

| | MeI wt % | Water wt % | HI wt % | MA wt % | MeOH wt % | DME wt % | Ac wt % | Others wt % | AD wt % | PA wt % | LiI wt % | FrOH ppm | Temperature ° C. | Pressure KPG |
|---|---|---|---|---|---|---|---|---|---|---|---|---|---|---|
| Comp. Ex. 1 | 10.9 | 2.1 | 0.1 | 2.8 | 0.3 | 0.01 | 70 | 1.1 | 0.02 | 0.01 | 15.3 | 211 | 190 | 2800 |
| Comp. Ex. 2 | 0.8 | 3.2 | 0.01 | 1.1 | 0.2 | 0.01 | remainder | 0.5 | 0.005 | 0.01 | 19.7 | 75 | 140 | 140 |
| Comp. Ex. 3 | 32.1 | 2.2 | 0.1 | 5.5 | 0.8 | 0.01 | remainder | 0.9 | 0.08 | 0.01 | 0.01 | 456 | 140 | 130 |
| Comp. Ex. 4 | 60.5 | 23.1 | 0.1 | 10.5 | 1.5 | 0.01 | remainder | 1.0 | 0.19 | 0.01 | less than detection limit (less than 1 ppb) | 957 | 116 | 130 |
| Comp. Ex. 5 | 0.9 | 1.1 | 0.01 | 0.8 | 95 ppm | 0.01 | remainder | 0.3 | 0 | 0.01 | 0.4 | 57 | 140 | 130 |
| Comp. Ex. 6 | 2.9 | 1.5 | 0.01 | 2.2 | 0.3 | 0.01 | remainder | 0.4 | 0.01 | 0.01 | 0.0003 | 151 | 136 | 140 |

TABLE 62-continued

|  | MeI wt % | Water wt % | HI wt % | MA wt % | MeOH wt % | DME wt % | Ac wt % | Others wt % | AD wt % | PA wt % | LiI wt % | FrOH ppm | Temperature ° C. | Pressure KPG |
|---|---|---|---|---|---|---|---|---|---|---|---|---|---|---|
| Comp. Ex. 7 | 8.4 | 4.9 | 0.01 | 6.5 | 0.9 | 0.01 | remainder | 0.6 | 0.0003 | 0.01 | less than detection limit (less than 1 ppb) | 549 | 150 | 200 |
| Comp. Ex. 8 | 95 ppb | 0.2 | 23 ppb | 18 ppm | less than detection limit (less than 1 ppm) | less than detection limit (less than 1 ppm) | remainder | 0.01 | 0 | 0 | less than detection limit (less than 1 ppb) | 0 | 137 | 80 |
| Comp. Ex. 9 | 6 ppb | 0.05 | 4 ppb | 5 ppm | less than detection limit (less than 1 ppm) | less than detection limit (less than 1 ppm) | remainder | 0.01 | 0 | 0.01 | 0.0002 | 0 | 160 | 230 |
| Comp. Ex. 10 | remainder | 1.1 | 0.01 | 9.7 | 0.5 | 0.01 | 2.1 | 0.01 | 0.05 | 0 | less than detection limit (less than 1 ppb) | 643 | 80 | 250 |
| Comp. Ex. 11 | 1 ppb | 0.05 | 0.7 ppb | 7 ppm | less than detection limit (less than 1 ppm) | less than detection limit (less than 1 ppm) | remainder | 0.01 | 0.8 ppm | 0.01 | less than detection limit (less than 1 ppb) | 433 | 138 | 80 |
| Comp. Ex. 12 | 3 | 1.5 | 0.01 | 2 | 0.2 | 0.01 | remainder | 0.20 | 0.01 | 0.01 | 0.0003 | 148 | 136 | 140 |

TABLE 63

|  | MeI wt % | Water wt % | HI wt % | MA wt % | MeOH wt % | DME wt % | Ac wt % | Others wt % | AD wt % | PA wt % | LiI wt % | FrOH ppm | Temperature ° C. | Pressure KPG |
|---|---|---|---|---|---|---|---|---|---|---|---|---|---|---|
| Example 1 | 10.5 | 2.2 | 0.1 | 3 | 0.4 | 0.01 | remainder | 1.1 | 0.02 | 0.01 | 14.9 | 0 | 190 | 2800 |
| Example 2 | 0.9 | 3 | 0.01 | 1.2 | 0.2 | 0.01 | remainder | 0.5 | 0.004 | 0.01 | 20.1 | 0 | 140 | 140 |
| Example 3 | 32.8 | 1.9 | 0.1 | 6.1 | 1.1 | 0.01 | remainder | 0.9 | 0.09 | 0.01 | 0.01 | 0 | 140 | 130 |
| Example 4 | 59.9 | 22.8 | 0.1 | 11 | 1.8 | 0.01 | remainder | 1.0 | 0.2 | 0.01 | less than detection limit (less than 1 ppb) | 1 | 116 | 130 |
| Example 5 | 1.1 | 0.9 | 0.01 | 1.1 | 102 ppm | 0.01 | remainder | 0.3 | 0 | 0.01 | 0.4 | 0 | 140 | 130 |
| Example 6 | 3.2 | 1.8 | 0.01 | 2 | 0.3 | 0.01 | remainder | 0.4 | 0.008 | 0.01 | 0.0003 | 0 | 136 | 140 |
| Example 7 | 7.9 | 4.7 | 0.01 | 6 | 0.8 | 0.01 | remainder | 0.6 | 0.0003 | 0.01 | less than detection limit (less than 1 ppb) | 0 | 150 | 200 |
| Example 8 | 102 ppb | 0.18 | 19 ppb | 23 ppm | less than detection limit (less than 1 ppm) | less than detection limit (less than 1 ppm) | remainder | 0.01 | 0 | 0 | less than detection limit (less than 1 ppb) | 0 | 137 | 80 |
| Example 9 | 5 ppb | 0.04 | 6 ppb | 5 ppm | less than detection limit (less than 1 ppm) | less than detection limit (less than 1 ppm) | remainder | 0.01 | 0 | 0.01 | 0.0002 | 0 | 160 | 230 |
| Example 10 | remainder | 0.8 | 0.01 | 10.1 | 1.1 | 0.01 | 1.9 | 0.01 | 0.08 | 0 | less than detection limit | 1 | 80 | 250 |

TABLE 63-continued

|  | MeI wt % | Water wt % | HI wt % | MA wt % | MeOH wt % | DME wt % | Ac wt % | Others wt % | AD wt % | PA wt % | LiI wt % | FrOH ppm | Temperature ° C. | Pressure KPG |
|---|---|---|---|---|---|---|---|---|---|---|---|---|---|---|
| Example 11 | 2.9 | 1.3 | 0.01 | 1.8 | 0.2 | 0.01 | remainder | 0.2 | 0.009 | 0.01 | (less than 1 ppb) 0.0003 | 68 | 136 | 140 |
| Example 12 | 3.2 | 1.6 | 0.01 | 1.9 | 0.1 | 0.01 | remainder | 0.2 | 0.01 | 0.01 | 0.0003 | 12 | 136 | 140 |
| Example 13 | 3.1 | 1.4 | 0.01 | 2.1 | 0.2 | 0.01 | remainder | 0.2 | 0.011 | 0.01 | 0.0003 | 0 | 136 | 140 |
| Example 14 | 2.8 | 1.5 | 0.01 | 2 | 0.2 | 0.01 | remainder | 0.2 | 0.008 | 0.01 | 0.0003 | 1 | 136 | 140 |
| Example 15 | 3.3 | 1.6 | 0.01 | 2 | 0.2 | 0.01 | remainder | 0.2 | 0.011 | 0.01 | 0.0003 | 0 | 136 | 140 |
| Example 16 | 3 | 1.2 | 0.01 | 2.1 | 0.2 | 0.01 | remainder | 0.2 | 0.008 | 0.01 | 0.0003 | 0 | 136 | 140 |
| Example 17 | 3.3 | 1.5 | 0.01 | 1.9 | 0.2 | 0.01 | remainder | 0.2 | 0.012 | 0.01 | 0.0003 | 0 | 136 | 140 |
| Example 18 | 0.9 ppb | 0.05 | 0.8 ppb | 8 ppm | less than detection limit (less than 1 ppm) | less than detection limit (less than 1 ppm) | remainder | 0.001 | 1 ppm | 0.01 | less than detection limit (less than 1 ppb) | 0 | 138 | 80 |
| Example 19 | 1.1 ppb | 0.05 | 0.9 ppb | 7 ppm | less than detection limit (less than 1 ppm) | less than detection limit (less than 1 ppm) | remainder | 0.001 | 1.1 ppm | 0.01 | less than detection limit (less than 1 ppb) | 0 | 138 | 80 |

TABLE 64

|  | $H_2$ vol % | CO vol % | $CO_2$ vol % | $CH_4$ vol % | $N_2$ vol % | $O_2$ vol % | $H_2$ kPa | CO kPa | $CO_2$ kPa | $CH_4$ kPa | $N_2$ kPa | $O_2$ kPa |
|---|---|---|---|---|---|---|---|---|---|---|---|---|
| Comp. Ex. 1 | 0 | 93 | 0 | 0 | 0 | 7 | 0 | 94 | 0 | 0 | 0 | 7.09 |
| Comp. Ex. 2 | 0 | 93 | 0 | 0 | 0 | 7 | 0 | 94 | 0 | 0 | 0 | 7.09 |
| Comp. Ex. 3 | 0 | 93 | 0 | 0 | 0 | 7 | 0 | 94 | 0 | 0 | 0 | 7.09 |
| Comp. Ex. 4 | 0 | 93 | 0 | 0 | 0 | 7 | 0 | 94 | 0 | 0 | 0 | 7.09 |
| Comp. Ex. 5 | 0 | 93 | 0 | 0 | 0 | 7 | 0 | 94 | 0 | 0 | 0 | 7.09 |
| Comp. Ex. 6 | 0 | 93 | 0 | 0 | 0 | 7 | 0 | 94 | 0 | 0 | 0 | 7.09 |
| Comp. Ex. 7 | 0 | 93 | 0 | 0 | 0 | 7 | 0 | 94 | 0 | 0 | 0 | 7.09 |
| Comp. Ex. 8 | 0 | 93 | 0 | 0 | 0 | 7 | 0 | 94 | 0 | 0 | 0 | 7.09 |
| Comp. Ex. 9 | 0 | 93 | 0 | 0 | 0 | 7 | 0 | 94 | 0 | 0 | 0 | 7.09 |
| Comp. Ex. 10 | 0 | 93 | 0 | 0 | 0 | 7 | 0 | 94 | 0 | 0 | 0 | 7.09 |
| Comp. Ex. 11 | 0 | 93 | 0 | 0 | 0 | 7 | 0 | 94 | 0 | 0 | 0 | 7.09 |
| Comp. Ex. 12 | 0 | 0 | 0 | 0 | 93 | 7 | 0 | 0 | 0 | 0 | 94 | 7.09 |
| Example 1 | 0 | remainder | 0 | 0 | 0 | 0.010 | 0 | 101 | 0 | 0 | 0 | 0.01 |
| Example 2 | 0 | remainder | 0 | 0 | 0 | 0.010 | 0 | 101 | 0 | 0 | 0 | 0.01 |
| Example 3 | 0 | remainder | 0 | 0 | 0 | 0.010 | 0 | 101 | 0 | 0 | 0 | 0.01 |
| Example 4 | 0 | remainder | 0 | 0 | 0 | 0.010 | 0 | 101 | 0 | 0 | 0 | 0.01 |
| Example 5 | 0 | remainder | 0 | 0 | 0 | 0.010 | 0 | 101 | 0 | 0 | 0 | 0.01 |
| Example 6 | 0 | remainder | 0 | 0 | 0 | 0.010 | 0 | 101 | 0 | 0 | 0 | 0.01 |
| Example 7 | 0 | remainder | 0 | 0 | 0 | 0.010 | 0 | 101 | 0 | 0 | 0 | 0.01 |
| Example 8 | 0 | remainder | 0 | 0 | 0 | 0.010 | 0 | 101 | 0 | 0 | 0 | 0.01 |
| Example 9 | 0 | remainder | 0 | 0 | 0 | 0.010 | 0 | 101 | 0 | 0 | 0 | 0.01 |
| Example 10 | 0 | remainder | 0 | 0 | 0 | 0.010 | 0 | 101 | 0 | 0 | 0 | 0.01 |
| Example 11 | 0 | 95 | 0 | 0 | 0 | 5 | 0 | 96 | 0 | 0 | 0 | 5.07 |
| Example 12 | 0 | 99 | 0 | 0 | 0 | 1 | 0 | 100 | 0 | 0 | 0 | 1.01 |
| Example 13 | 0 | remainder | 0 | 0 | 0 | 0.00010 | 0 | 101 | 0 | 0 | 0 | 0.00 |
| Example 14 | 0 | 0 | 0 | 0 | remainder | 0.10 | 0 | 0 | 0 | 0 | 101 | 0.10 |
| Example 15 | 0 | 0 | 0 | 0 | remainder | 0.010 | 0 | 0 | 0 | 0 | 101 | 0.01 |
| Example 16 | 0 | 0 | 0 | 0 | remainder | 0.0010 | 0 | 0 | 0 | 0 | 101 | 0.001 |
| Example 17 | 2 | remainder | 15 | 7 | 8 | 0.010 | 2 | 69 | 15 | 7 | 8 | 0.00 |
| Example 18 | 0 | remainder | 0 | 0 | 0 | 0.00010 | 0 | 101 | 0 | 0 | 0 | 0.00 |
| Example 19 | 0 | remainder | 0 | 0 | 0 | 0.000010 | 0 | 101 | 0 | 0 | 0 | 0.00 |

TABLE 65

| | | Corrosion test results | | | | | | | |
|---|---|---|---|---|---|---|---|---|---|
| | | Zr | | HB2 | | HC276 | | SUS316 | |
| | | mm/Y | Partial corrosion | mm/Y | Partial corrosion | mm/Y | Partial corrosion | mm/Y | Partial corrosion | APHA |
| Comp. Ex. 1 | | 0.000 | absent | 0.1 | present | — | — | — | — | >500 |
| Comp. Ex. 2 | | 0.000 | absent | 0.1 | present | — | — | — | — | >500 |
| Comp. Ex. 3 | | 0.000 | absent | 0.05 | present | 0.02 | present | 0.06 | absent | >500 |
| Comp. Ex. 4 | | 0.000 | absent | 0.12 | present | 0.02 | present | 0.11 | absent | >500 |
| Comp. Ex. 6 | | 0.000 | absent | 0.15 | present | 0.12 | present | — | — | >500 |
| Comp. Ex. 7 | | 0.000 | absent | 0.19 | present | 0.28 | present | — | — | >500 |
| Comp. Ex. 8 | | 0.000 | absent | 0.05 | present | 0.03 | absent | 0.19 | absent | 80 |
| Comp. Ex. 9 | | 0.000 | absent | 0.09 | present | 0.02 | present | 0.08 | present | 90 |
| Comp. Ex. 10 | | 0.000 | absent | 0.04 | present | 0.03 | present | 0.01 | present | >500 |
| Comp. Ex. 11 | | 0.000 | absent | 0.08 | present | 0.03 | present | 0.02 | — | 70 |
| Comp. Ex. 12 | | 0.000 | absent | 0.29 | present | 0.3 | present | — | — | >500 |
| Comp. Ex. 13 | Feed plate | 0.000 | absent | 0.05 | present | 0.02 | present | 0.09 | absent | >500 |
| | Upper part of column | 0.000 | absent | 0.06 | present | 0.01 | present | 0.06 | absent | |
| Comp. Ex. 14 | 2nd plate from bottom | 0.000 | absent | 0.17 | present | 0.21 | present | — | — | >500 |
| | Upper part of column | 0.000 | absent | 0.09 | present | 0.2 | present | — | — | |

TABLE 66

| | | Corrosion test results | | | | | | | |
|---|---|---|---|---|---|---|---|---|---|
| | | Zr | | HB2 | | HC276 | | SUS316 | |
| | | mm/Y | Partial corrosion | mm/Y | Partial corrosion | mm/Y | Partial corrosion | mm/Y | Partial corrosion | APHA |
| Example 1 | | 0.000 | absent | 0.01 | absent | — | — | — | — | 60 |
| Example 2 | | 0.000 | absent | 0.001 | absent | — | — | — | — | 50 |
| Example 3 | | 0.000 | absent | 0.005 | absent | 0.01 | absent | 0.06 | absent | 50 |
| Example 4 | | 0.000 | absent | 0.015 | absent | 0.025 | absent | 0.10 | absent | 25 |
| Example 5 | | 0.000 | absent | 0.01 | absent | 0.02 | absent | 0.10 | absent | 25 |
| Example 6 | | 0.000 | absent | 0.03 | absent | 0.09 | absent | — | — | 25 |
| Example 7 | | 0.000 | absent | 0.07 | absent | 0.25 | — | — | — | 35 |
| Example 8 | | 0.000 | absent | 0.001 | absent | 0.01 | absent | 0.05 | absent | 10 |
| Example 9 | | 0.000 | absent | 0.000 | absent | 0.005 | absent | 0.03 | absent | 10 |
| Example 10 | | 0.000 | absent | 0.001 | absent | 0.02 | absent | 0.13 | absent | 40 |
| Example 11 | | 0.000 | absent | 0.08 | absent | 0.19 | absent | — | — | 50 |
| Example 12 | | 0.000 | absent | 0.05 | absent | 0.11 | absent | — | — | 40 |
| Example 13 | | 0.000 | absent | 0.03 | absent | 0.09 | absent | — | — | 20 |
| Example 14 | | 0.000 | absent | 0.06 | absent | 0.1 | absent | — | — | 40 |
| Example 15 | | 0.000 | absent | 0.04 | absent | 0.09 | absent | — | — | 30 |
| Example 16 | | 0.000 | absent | 0.03 | absent | 0.10 | absent | — | — | 25 |
| Example 17 | | 0.000 | absent | 0.03 | absent | 0.11 | absent | — | — | 35 |
| Example 18 | | 0.000 | absent | 0.000 | absent | 0.000 | absent | 0.05 | — | 5 |
| Example 19 | | 0.000 | absent | 0.000 | absent | 0.000 | absent | 0.04 | — | 5 |
| Example 20 | Feed plate | 0.000 | absent | 0.005 | absent | 0.02 | absent | — | — | 40 |
| | Upper part of column | 0.000 | absent | 0.002 | absent | 0.01 | absent | — | — | |
| Example 21 | 2nd plate from bottom | 0.000 | absent | 0.01 | absent | 0.19 | absent | — | — | 10 |
| | Upper part of column | 0.000 | absent | 0.009 | absent | 0.18 | absent | — | — | |
| Example 22 | 2nd plate from bottom | 0.000 | absent | 0.02 | absent | 0.02 | absent | 0.07 | — | 80 |
| | Upper part of column | 0.000 | absent | 0.03 | absent | 0.01 | absent | 0.06 | — | |

The results given in Tables 62 to 66 demonstrate as follows.

Carbon monoxide lowers the oxygen concentration by a reductive reaction: $CO + \frac{1}{2}O_2 \rightarrow CO_2$ to form a so-called reducing atmosphere, but may fail to form such a reducing atmosphere at a high oxygen concentration. Comparisons of Comparative Examples 1 to 11 respectively with corresponding Examples 1 to 11, which are different in liquid compositions, demonstrate as follows. The comparative examples performed at an oxygen concentration of 7 percent by volume had higher corrosion rates of the test piece HB2 and higher formic acid concentrations as compared with the corresponding examples, where the test piece HB2 is approximately devoid of Cr and is weak under an oxidizing atmosphere. In comparison between Comparative Example 11 and Examples 18 and 19, the Comparative Example 11 had a somewhat lower corrosion rate of the test piece SUS316, as compared with Examples 18 and 19. This is probably because of a tendency that the corrosion rate increases contrarily in an excessively high reducing atmosphere, where this tendency is one of characteristic properties of stainless steels. Thus, it was verified that the presence of a small amount of oxygen in the process may lower the corrosivity under some conditions.

In the comparative examples, the test pieces such as HB2 often suffered from pitting corrosion and/or spot corrosion, which seems to occur by the action of iodine formed typically by the reaction: $2HI + \frac{1}{2}O_2 \rightarrow I_2 + H_2O$. At not-so-high oxygen concentrations, the test pieces SUS316 and HC276, which contain Cr, were corroded at somewhat higher corrosion rates, but were not extremely corroded.

The solution after the corrosion test had an apparently higher APHA color index as compared with the solution before the corrosion test, and became dark to reddish brown, which color is peculiar to iodine. Thus, coloring due to iodine formation probably occurred. The APHA color indices are indicated up to 500 in the tables. In test samples in which the oxygen concentration was high and iodine $I_2$ was formed at a high concentration, the solution had little or no transparency and highly colored to a degree not expressed by the APHA color index. This indicates that iodine effluxes to a succeeding (downstream) step in a process flow at a high oxygen concentration. Such efflux of iodine may lead to the acceleration of corrosion in the succeeding step, and to the coloring or the increase in a total iodine concentration of a product due to contamination with iodine.

Comparative Example 12 is an experimental sample performed in a nitrogen atmosphere which offers no activity of lowering the oxygen concentration, unlike carbon monoxide. Thus, this comparative example had significantly higher corrosion rates of the test pieces (in particular, the test piece HB2) and had a higher formic acid concentration, as compared with Example 6.

Example 11 was performed at an oxygen concentration (1 percent by volume) half the oxygen concentration in Comparative Example 12. Although there are still adverse influences of oxygen on the corrosion test, the coloring and, the formic acid concentration, these influences are considerably small as compared with Comparative Example 12. Thus, the above oxygen concentration is not an unacceptable concentration.

Example 12 was performed at an oxygen concentration (0.5 percent by volume) one-fourth the oxygen concentration in Comparative Example 12. Although there are still adverse influences of oxygen on the corrosion test, the coloring, and the formic acid concentration, these influences are considerably small as compared with Comparative Example 12. Thus, the above oxygen concentration is not an unacceptable concentration.

Example 13 is a sample in which the oxygen concentration was lowered as low as possible, but as long as measurable. The results of Example 13 are substantially equivalent to those of Example 6, in which the oxygen concentration was 0.01 percent by volume. This demonstrates that oxygen, when present in concentrations lowered to some extent, has little or approximately no adverse influence and behaves similarly in such lowered concentrations.

Examples 18 and 19 had somewhat higher corrosion rates of the test piece SUS316, as compared with Comparative Example 11. This is probably because SUS316 may be corroded at a higher corrosion rate in a highly reducing atmosphere, and is corroded acceleratedly under conditions being approximately devoid of oxygen, as under the conditions of these examples. Since this tendency seems to be observed more markedly under a lower oxygen concentration, it is not advisable to minimize the oxygen concentration to next to zero (for example, 1 ppt by volume, 1 ppb by volume) under a reducing condition in the presence of carbon monoxide, particularly for stainless steel (SUS) materials. However, such a degree of corrosion was not an unusable level. Under these conditions, impurities are present at such a level as to contain little or approximately no iodine, and the oxygen concentration is extremely low. This gives an acetic acid product with little or approximately no coloring.

Example 14 is a sample performed in a nitrogen gas atmosphere at a lower oxygen concentration of 0.1 percent by volume. As compared with Example 11, Example 14 had lower corrosion (corrosion rate) of the test piece HB2 and had a significantly lower formic acid concentration, where the corrosion proceeded to some extend to cause coloring, but the corrosion at the oxygen concentration was not unacceptable.

Examples 15 and 16 are samples performed in a nitrogen gas atmosphere at further lower oxygen concentrations. In Examples 15 and 16, as well as Example 13, the degree of corrosion is not so different from that in the samples performed in a carbon monoxide atmosphere. At a lower oxygen concentration, the corrosion rate and the coloring were approximately the same as those in the carbon monoxide atmosphere; but the formic acid concentration was significantly lower.

Example 17 is an experimental sample employing a different feed gas. A comparison with Example 6 demonstrates that even different feed gases give approximately the same corrosion rate and APHA color index, when the feed gases contain carbon monoxide gas in a sufficient amount and have an identical oxygen concentration.

A comparison between Comparative Example 13 and Example 20 demonstrates that the test pieces, in particular the test piece HB2 which is susceptible to oxygen, are more corroded, and the side-cut liquids have higher degrees of coloring (greater APHA color indices) at a higher oxygen concentration in carbon monoxide fed to the reactor. In Comparative Example 13, the test piece HB2 placed at the upper part of the first distillation column was corroded at a higher corrosion rate, even though performed at a lower temperature, as compared with the test piece HB2 placed at the feed plate. This is because of considerably high oxygen concentration at the upper part of the column. The test piece HB2 generally offers good corrosion resistance at a low oxygen concentration. Thus, the test piece HB2 is corroded at a lower corrosion rate under a low oxygen concentration condition as in Example 20, as compared with a sample under an overall high oxygen concentration, while the test piece HB2 is corroded at a higher corrosion rate when placed at the feed plate having a higher temperature, as compared with the case when placed at the upper part of the column having a lower temperature.

A comparison between Comparative Example 14 and Example 21 offered a similar tendency to the comparison between Comparative Example 13 and Example 20, although employing different feed compositions.

In general, the material cost decreases in the descending sequence of Zr, HB2, HC, and SUS (stainless steel).

In consideration of the cost (price), the material can be selected on the basis of the corrosion rate according to the following criteria, although the selection may be affected typically by the thickness of the material and the frequency of renewal.

Corrosion rate of 0.05 mm/Y or less: suitable for use

Corrosion rate of greater than 0.05 mm/Y to 0.1 mm/Y: usable level

Corrosion rate of greater than 0.1 mm/Y to 0.2 mm/Y: usable under some conditions Corrosion rate of greater than 0.2 mm/Y: unsuitable for use

INDUSTRIAL APPLICABILITY

The present invention can effectively eliminate or minimize the corrosion of a process unit and/or line and is extremely useful as a process for stably producing high-quality acetic acid.

REFERENCE SIGNS LIST (1) reactor
(2) evaporator
(3) light ends column (first distillation column)
(5) dehydration column (second distillation column)
(6) heavy ends column (third distillation column)
(7) rectifying column (fourth distillation column)
(8) ion exchange tank
(10) decanter
(11) first aldehyde-removing column (fifth distillation column)
(12) aqueous extraction-distillation column (sixth distillation column)
(13) second aldehyde-removing column (seventh distillation column)
(14) alkane-removing column (eighth distillation column)
(16) high-pressure absorber
(17) low-pressure absorber
(18) stripper

The invention claimed is:

1. A method for producing acetic acid by a process, the process comprising:
   (1) carbonylating methanol with carbon monoxide in the presence of a catalytic system, acetic acid, methyl acetate, and water, the catalytic system comprising a metal catalyst and methyl iodide, wherein the metal catalyst comprises a cobalt catalyst, a rhodium catalyst, or an iridium catalyst, alone or in combination; and
   (A) separating a reaction mixture resulting from the reaction step into:
      a stream containing the catalyst;
      an acetic acid stream rich in acetic acid; and
      a stream rich in a lower-boiling component or components as compared with the acetic acid stream,
   the step (A) being performed using at least one selected from the group consisting of evaporators and distillation columns,
   the method comprising:
   controlling an oxygen concentration by procedure (a) controlling the oxygen concentration in a gaseous phase in the process to less than 7 percent by volume; and optionally procedure (b) controlling the oxygen concentration in a liquid phase in the process to less than $7\times10^{-5}$ g/g; and
   controlling a formic acid concentration in the liquid phase in the process to 500 ppm by mass or less,
   wherein the gaseous phase is in at least one step selected from the group consisting of the reaction step (1) and steps included in the separation step (A), and wherein the liquid phase is in at least one step selected from the group consisting of the reaction step (1) and steps included in the separation step (A); and
   wherein the oxygen concentration is controlled before or simultaneously with controlling the formic acid concentration.

2. The method according to claim 1,
   wherein the gaseous phase in the process comprises at least one selected from methyl iodide and hydrogen iodide.

3. The method according to claim 1,
   wherein the gaseous phase in the process comprises at least one selected from the group consisting of:
   acetic acid;
   methyl acetate;
   methanol;
   water;
   acetaldehyde;
   an acetaldehyde-derived by-product; and
   a dialkyl ether,
   wherein the by-product comprises at least one selected from the group consisting of:
      alkyl iodides containing 2 or more carbon atoms;
      alkanals containing 4 or more carbon atoms;
      alkanecarboxylic acids containing 3 or more carbon atoms;
      alkanes; and
      ketones, and
   wherein the dialkyl ether comprises
      dimethyl ether.

4. The method according to claim 1,
   wherein the step of controlling the oxygen concentration is controlled by at least one procedure selected from:
   (a-1) controlling the oxygen concentration in the gaseous phase to 5 percent by volume or less; and
   (b-1) controlling the oxygen concentration in the liquid phase to $2\times10^{-5}$ g/g or less.

5. The method according to claim 1,
   wherein oxygen is present in a proportion to carbon monoxide of 2 percent by volume or less in each of the gaseous phase and the liquid phase in at least one process stream.

6. The method according to claim 1,
   wherein oxygen is present in a proportion to carbon monoxide of 1 percent by volume or less in each of the gaseous phase and the liquid phase in at least one process stream.

7. The method according to claim 1,
   wherein the method comprises:
   introducing at least one component selected from the group consisting of oxygen-containing gases, oxygen-containing compounds, and oxygen generators to the process; and
   whereby, in at least one process stream, performing at least one procedure selected from:
   (c) controlling the oxygen concentration in the gaseous phase to 1 ppt by volume or more and less than 7 percent by volume; and
   (d) controlling the oxygen concentration in the liquid phase to $0.1\times10^{-9}$ g/g and less than $7\times10^{-5}$ g/g.

8. The method according to claim 1,
   wherein the oxygen concentration in the gaseous phase in the process is controlled to 1 ppb by volume or more and less than 7 percent by volume.

9. The method according to claim 1,
wherein the oxygen concentration in at least one process stream, comprising hydrogen iodide and methyl iodide, selected from the gaseous phase and the liquid phase is controlled to 0.25 mole or less per mole of the totality of hydrogen iodide and methyl iodide.

10. The method according to claim 1,
wherein the method comprises
(4) a purification step group that yields purified acetic acid from the acetic acid stream, and
wherein the purification step group (4) comprises at least (5) a dehydrating step among the steps of:
(5) dehydrating the acetic acid stream;
(6) removing a higher-boiling component or components from the acetic acid stream;
(7) further rectifying the acetic acid stream; and
(8) separating an iodine compound or compounds from the acetic acid stream by ion exchange.

11. The method according to claim 1,
wherein the method comprises
(9) a separation step group that separates at least acetaldehyde from the stream rich in lower-boiling components, and
wherein the separation step group (9) comprises at least steps (10) to (13) among the steps of:
(10) condensing the stream rich in lower-boiling components to separate the stream into an upper phase and a lower phase;
(11) forming an overhead from a portion of at least one of the upper phase and the lower phase, the overhead being rich in acetaldehyde and methyl iodide;
(12) extracting acetaldehyde from the overhead to give an extract and a raffinate, where the extract is rich in acetaldehyde, and the raffinate is rich in methyl iodide;
(13) separating acetaldehyde from a portion of at least one of the extract and the raffinate; and
(14) separating an alkane or alkanes from at least one of the upper phase and the lower phase.

12. The method according to claim 1,
wherein the method produces an offgas and comprises
(15) an offgas treatment step group that allows an absorbing solvent to absorb the offgas from the process,
wherein the offgas treatment step group (15) comprises
(16) allowing the absorbing solvent to absorb the offgas; and
optionally (18) stripping a gaseous component absorbed in the step (16).

13. The method according to claim 1,
wherein the gaseous phase from at least one step selected from the group consisting of the reaction step (1) and steps included in the separation step (A) in the process is an offgas from the process.

14. A method for restraining formation of at least one of iodine and formic acid in a process, the process comprising:
(1) carbonylating methanol with carbon monoxide in the presence of a catalytic system, acetic acid, methyl acetate, and water, the catalytic system comprising a metal catalyst and methyl iodide, wherein the metal catalyst comprises a cobalt catalyst, a rhodium catalyst, or an iridium catalyst, alone or in combination; and
(A) separating a reaction mixture resulting from the reaction step into:
a stream containing the catalyst;
an acetic acid stream rich in acetic acid; and
a stream rich in a lower-boiling component or components as compared with the acetic acid stream,
the step (A) being performed using at least one selected from the group consisting of evaporators and distillation columns,
the method comprising:
controlling an oxygen concentration by procedure (a) controlling the oxygen concentration in a gaseous phase in the process to less than 7 percent by volume; and optionally procedure (b) controlling the oxygen concentration in a liquid phase in the process to less than $7 \times 10^{-5}$ g/g; and
controlling a formic acid concentration in the liquid phase in the process to 500 ppm by mass or less,
wherein the gaseous phase is in at least one step selected from the group consisting of the reaction step (1) and steps included in the separation step (A), and wherein the liquid phase is in at least one step selected from the group consisting of the reaction step (1) and steps included in the separation step (A); and
wherein the oxygen concentration is controlled before or simultaneously with controlling the formic acid concentration.

* * * * *